United States Patent
Rubin et al.

(10) Patent No.: US 7,488,710 B2
(45) Date of Patent: Feb. 10, 2009

(54) SFRP AND PEPTIDE MOTIFS THAT INTERACT WITH SFRP AND METHODS OF THEIR USE

(75) Inventors: Jeffrey S. Rubin, Potomac, MD (US); Aykut Üren, Rockville, MD (US); Matthew Todd Gillespie, Mount Waverly (AU); Nicole Joy Horwood, Ashwood (AU)

(73) Assignees: The United States of America as represented by the Department of Health and Human Services, Washington, DC (US); St. Vincent's Institute of Medical Research, Fitzroy, Victoria (AU)

( * ) Notice: Subject to any disclaimer, the term of this patent is extended or adjusted under 35 U.S.C. 154(b) by 634 days.

(21) Appl. No.: 10/466,136

(22) PCT Filed: Jan. 10, 2002

(86) PCT No.: PCT/US02/00869

§ 371 (c)(1), (2), (4) Date: Jul. 10, 2003

(87) PCT Pub. No.: WO02/055547

PCT Pub. Date: Jul. 18, 2002

(65) Prior Publication Data

US 2004/0077828 A1      Apr. 22, 2004

Related U.S. Application Data

(60) Provisional application No. 60/260,908, filed on Jan. 10, 2001.

(51) Int. Cl.
*A61K 38/00*   (2006.01)
(52) U.S. Cl. .................. 514/2; 514/7; 514/8; 514/12
(58) Field of Classification Search .................. None
See application file for complete search history.

(56) References Cited

U.S. PATENT DOCUMENTS

| | | | |
|---|---|---|---|
| 5,204,328 A | 4/1993 | Nutt et al. |
| 5,238,839 A | 8/1993 | Cantor et al. |
| 5,352,667 A | 10/1994 | Lider et al. |
| 5,519,005 A | 5/1996 | Lider et al. |
| 5,536,814 A | 7/1996 | Ruoslahti et al. |
| 5,578,569 A | 11/1996 | Tam |
| 5,846,932 A | 12/1998 | Lowe et al. |
| 5,851,984 A | 12/1998 | Matthews et al. |
| 5,912,234 A | 6/1999 | Ruoslahti et al. |
| 5,939,271 A | 8/1999 | Tessier-Lavigne et al. |
| 6,043,053 A | 3/2000 | Barnes et al. |
| 6,110,718 A | 8/2000 | Shisheva |
| 6,479,255 B1 | 11/2002 | Rubin et al. |
| 6,589,528 B2 | 7/2003 | Ito et al. |
| 6,600,018 B1 * | 7/2003 | Rubin et al. .............. 530/350 |

FOREIGN PATENT DOCUMENTS

| WO | WO 97/39357 | 10/1997 |
|---|---|---|
| WO | WO 98/13493 | 4/1998 |
| WO | WO98/46751 | 10/1998 |
| WO | WO 98/54325 | 12/1998 |
| WO | WO 99/09152 | 2/1999 |
| WO | WO 99/26960 | 6/1999 |
| WO | WO 99/29865 | 6/1999 |
| WO | WO 01/19855 | 3/2001 |
| WO | WO 01/57188 | 8/2001 |

OTHER PUBLICATIONS

Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Garcia-Hoyos et al. Mol Vision 224; 10: 426-431.*
EMBL Database, Jan. 25, 2000, Accession No. AF218056.
EMBL Database, Nov. 5, 1999, Accession No. AV354083.
EMBL Database, Nov. 3, 1999, Accession No. AV304328.
EMBL Database, Oct. 18, 1996, Accession No. U24163.
EMBL Database, Apr. 9, 1999, Accession No. AI587049.
Abu-Jawdeh, et al., "Differential expression of frpHE: a novel human stromal protein of the secreted frizzled gene family, during the endometrial cycle and malignancy," *Lab Invest.* 79:439-447, 1999.
Ackerman and Knowles, "Cloning and mapping of the *UNC5C* gene to human chromosome 4q21-123," *Genomics* 52:205-208, 1998.
Bafico, et al., "Interaction of frizzled related protein (FRP) with Wnt ligands and the frizzled receptor suggests alternative mechanisms for FRP inhibition of Wnt signaling," *J. Biol. Chem.* 274:16180-16187, 1999.

(Continued)

*Primary Examiner*—Elizabeth C. Kemmerer
*Assistant Examiner*—Christina Borgeest
(74) *Attorney, Agent, or Firm*—Klarquist Sparkman, LLP

(57) ABSTRACT

This disclosure relates to a peptide motif and proteins containing the motif that are capable of binding to secreted Frizzled-related protein family members. Accordingly, the disclosure also includes methods of regulating the interaction of sFRP-1 with proteins containing the motif.

33 Claims, 16 Drawing Sheets

OTHER PUBLICATIONS

Banyai, et al., "The NTR module: domains of netrins, secreted frizzled related proteins, and type 1 procollagen C-proteinase enhancer protein are homologous with tissue inhibitors of metalloproteases," *Protein Science* 8:1636-1642, 1999.

Baranski, et al., "The dynamic expression pattern of *frzb-1* suggests multiple roles in chick development," *Developmental Biology* 217:25-41, 2000.

Bhanot, et al., "A New Member of the Frizzled Family from Drosophila Functions as a Wingless Receptor," *Nature*, 382(6588):225-230, Jul. 18, 1996.

Bradley and Brown, "The proto-oncogene *int*-1 encodes a secreted protein associated with the extracellular matrix," *The EMBO Journal* 9(5):1569-1575, 1990.

Cadigan, et al., "Wnt Signaling: A Common Theme in Animal Development," *Genes & Development*, 11(24):3286-3305, Dec. 15, 1997.

Chakrabarti, et al., "Secretory and inductive properties of *Drosophila wingless* protein in *Xenopus* oocytes and embryos," *Development* 115(1):355-369, 1992.

Chan, et al., "Two homologs of the *Drosophila* polarity gene frizzled (fz) are widely expressed in mammalian tissues," *The Journal of Biological Chemistry* 267(35):25202-25207, 1992.

Chang, et al., "Cloning and characterization of a secreted frizzled-related protein that is expressed by the retinal pigment epithelium," *Hum. Mol. Genet.* 8:575-583, 1999.

Cole, et al., "Deciphering the biology of mycobacterium tuberculosis from the complete genome sequences," *Nature* 393:537-544, 1998.

Dale, "Signal transduction by the Wnt family of ligands," *Biochem. J.* 329:209-223, 1998.

De Bellis, et al., "The *tbf*-1 gene from the white truffle *tuber borchii* codes for a structural cell wall protein specifically expressed in fruitbody," *Fungal Genetics and Biology* 25:87-99, 1998.

Finch, et al., "Human KGF is FGF-related with properties of a paracrine effector of epithelial cell growth," *Science* 245:752-755, 1989.

Finch, et al., "Purification and Molecular Cloning of a Secreted, Frizzled-Related Antagonist of Wnt Action," *Proc. Natl. Acad. Sci.*, 94(13):6770-6775, Jun. 24, 1997.

Forcier, et al., "Characteristics of ANP-binding sites in the adrenal capsules of term-pregnant rats," *Molecular and Cellular Endocrinology* 117:189-194, 1996.

Fujiwara, et al., Otsuka cDNA Project, EMBL Database, Sep. 29, 1996, Accession No. C15983.

Gammelin, et al., "Two Subtypes of Nucleoproteins (NP) of Influenza A Viruses," *Virology* 170:71-80, 1989.

Gaynor, et al., "Peptide inhibition of glomerular deposition of an anti-DNA antibody," *Proc. Natl. Acad. Sci. USA* 94:1955-1960, 1997.

Hausler, et al., "Secreted frizzled-related proteins are expressed by osteoblasts," *Bone* (New York) 27, p. 33S, 2000.

Hautanen, et al., "Effects of modifications of the RGD sequence and its context on recognition by the fibronectin receptor," *The Journal of Biological Chemistry* 264:1437-1442, 1989.

He, et al., "Glycogen synthase kinase-3 and dorsoventral patterning in *Xenopus* embryos," *Nature* 374:617-622, 1995.

He, et al., "A Member of the Frizzled Protein Family Mediating Axis Induction by Wnt-5A," *Science*, 275:1652-1654, Mar. 14, 1997.

Hedgecock, et al., "Netrins evoke mixed reactions in motile cells," *TIG* 13:251-253, 1997.

Hillier, "Soares-NhHMPu-S1 Homosapiens cDNA clone IMAGE:767205 SmRNA sequence," Washu-Merck EST Project, Database EST, May 15, 1997, GenBank Accession No. AA424647.

Hillier, et al., Washu-Merck EST Project, EMBL Database, Apr. 5, 1996, Accession No. N75803, XP-00207764.

Hoang, et al., "Primary Structure and Tissue Distribution of FRZB, a Novel Protein Related to Drosphila Frizzled, Suggest a Role in Skeletal Morphogenesis," *The Journal of Biological Chemistry*, 271(42):26131-26137, Oct. 18, 1996.

Hsieh, et al., "Biochemical characterization of Wnt-frizzled interactions using a soluble, biologically active vertebrate Wnt protein," *Proc. Natl. Acad. Sci. USA* 96:3546-3551, 1999.

Karavanova, et al., "Conditioned medium from a rat ureteric bud cell line in combination with bFGF induces complete differentiation of isolated metanephric mesenchyme," *Development* 122:4159-4167, 1996.

Kelley, et al., "Emergence of the keratinocyte growth factor multigene family during the great ape radiation," *Proc. Natl. Acad. Sci. USA* 89:9287-9291, 1992.

Korinek, et al., "Constitutive transcriptional activation by a β-catenin-Tcf complex in APC$^{-/-}$ colon carcinoma," *Science* 275:1784-1787, 1997.

Lalau, et al., "Natriuretic and Vasoactive Hormones and Glomerular Hyperfiltration in Hyperglycaemic Type 2 Diabetic Patients: Effect of Insulin Treatment," *Nephron* 63:296-302, 1993.

Leyns, et al., "Frzb-1 is a Secreted Antagonist of wnt Signaling Expressed in the Spemann Organizer," *Cell* 88(6):747-756, Mar. 21, 1997.

Lin, et al., "The cysteine-rich frizzled domain of Frzb-1 is required and sufficient for modulation of Wnt signaling," *Proc. Natl. Acad. Sci USA* 94:11196-11200, 1997.

Lowman, et al., "Molecular mimics of insulin-like growth factor 1 (IGF-1) for inhibiting IGF-1: IGF-binding protein interactions," *Biochemistry* 37:8870-8878, 1998.

Mayr, et al., "Fritz: a secreted frizzled-related protein that inhibits Wnt activity," *Mech. Dev.* 63:109-125, 1997.

McMahon, "The Wnt family of developmental regulators," *TIG* 8:236-242, 1992.

McMahon and Moon, "*int*-1—a proto-oncogene involved in cell signaling," *Development 1989 Supplement*, pp. 161-167, 1989.

McNicoll, et al., "Localization by photoaffinity labeling of natriuretic peptide receptor-A binding domain," *Biochemistry* 35:12950-12956, 1996.

Melkonyan, et al., "SARPs: A Family of Secreted Apoptosis-Related Proteins," *Proc. Natl. Acad. Sci.*, 94(25):13636-13641, Dec. 9, 1997.

Miller and Moon, "Signal transduction through β-catenin and specification of cell fate during embryogenesis," *Genes & Development* 10:2527-2539, 1996.

Miller, et al., "Differential expression patterns of Wnt genes in the murine female reproductive tract during development and the estrous cycle," *Mech. Dev.* 76:91-99, 1998.

Mitelman, et al., "A breakpoint map of recurrent chromosomal rearrangements in human neoplasia," *Nature Genetics Special Issue* 15:417-419, 1997.

Molenaar, et al., "XTcf-3 transcription factor mediates β-catenin-induced axis formation in xenopus embryos," *Cell* 86:391-399, 1996.

Morse, et al., "The glycoprotein of thogoto virus (a tick-borne orthomyxo-like virus) is related to the baculovirus glycoprotein GP64," *Virology* 186:640-646, 1992.

Nusse, et al., "Wnt Genes," *Cell* 69:1073-1087, 1992.

Nusse, et al., "Mode of proviral activation of a putative mammary oncogene (*int*-1) on mouse chromosome 15," *Nature* 307:131-136, 1984.

Papkoff, et al., "Wnt-1 regulates free pools of catenins and stabilizes APC-catenin complexes," *Mol. Cell Biol.* 16:2128-2134, 1996.

Parkin, et al., "Activity of Wnt-1 as a transmembrane protein," *Genes & Development* 7:2181-2193, 1993.

Parr and McMahon, "Dorsalizing signal *Wnt*-7a required for normal polarity of D-V and A-P axes of mouse limb," *Nature* 374:350-353, 1995.

Parr and McMahon, "*Wnt* genes and vertebrate development," *Current Opinion in Genetics and Development* 4:523-528, 1994.

Perrimon, "Serpentine proteins slither into the wingless and hedgehog fields," *Cell* 86:513-516, 1996.

Pfeffer, et al., "Crescent, a novel chick gene encoding a Frizzled-like cysteine-rich domain, is expressed in anterior regions during early embryogenesis," *Int. J. Dev. Biol.* 41:449-458, 1997.

Plow, et al., "The effect of ARG-GLY-ASP-containing peptides on fibrinogen and von Willebrand Factor binding to platelets," *Proc. Natl. Acad. Sci. USA* 82:8057-8061, 1985.

Presta, et al., "Biologically active synthetic fragments of human basic fibroblast growth factor (bFGF): identification of two ASP-GLY-ARG-containing domains involved in the mitogenic activity of bFGF in endothelial cells," *Journal of Cellular Physiology* 149:512-524, 1991.

Quinn, et al., "A combination of osteoclast differentiation factor and macrophase-colony stimulating factor is sufficient for both human and mouse osteoclast formation in vitro," *Endocrinology* 130:4424-4427, 1998.

Rattner, et al., "A Family of Secreted Proteins Contains Homology to the Cystein-Rich Ligand-Binding Domain of Frizzled Receptors," *Proc. Natl. Acad. Sci.*, 94(7):2859-2863, 1997.

Rattner, et al., "Mus musculus secreted frizzled related protein SFRP-1 (Sfrp 1) mRNA," GenBank Database, Apr. 23, 1997, Accession No. MMU88566.

Reichsman, et al., "Glycosaminoglycans can modulate extracellular localization of the wingless protein and promote signal transduction," *J. Cell Biol.* 135:819-827, 1996.

Rehn and Pihlajaniemi, "Identification of three N-terminal ends of type XVIII collagen chains and tissue-specific differences in the expression of the corresponding transcripts," *The Journal of Biological Chemistry* 270(9):4705-4711, 1995.

Rijsewijk, et al., "The drosophila homolog of the mouse mammary oncogene *int*-1 is identical to the segment polarity gene wingless," *Cell* 50:649-657, 1987.

Rubin, et al., "A broad-spectrum human lung fibroblast-derived mitogen is a variant of hepatocyte growth factor," *Proc. Natl. Acad. Sci. USA* 88:415-419, 1991.

Rubin, et al., "Purification and characterization of a newly identified growth factor specific for epithelial cells," *Proc. Natl. Acad. Sci. USA* 86:802-806, 1989.

Salic, et al., "Sizzled: A Secreted Xwnt8 Antagonist Expressed in the Ventral Marginal Zone of Xenopus Embryos," *Development*, 124(23):4739-4748, Dec. 1997.

Schaefer and Kahn, "Cyanobacterial transposons Tn*5469* and Tn*5541* represent a novel noncomposite transposon family," *Journal of Bacteriology* 180:6059-6063, 1998.

Seither and Grummt, "Molecular cloning of RPA2, the gene encoding the second largest subunit of mouse RNA polymerase I," *Genomics* 37:135-139, 1996.

Shimizu, et al., "Transformation by Wnt family proteins correlates with regulation of beta-catenin," *Cell Growth and Differ.* 8:1349-1358, 1997.

Shisheva, et al., "Cloning, characterization, and expression of a novel $Zn^{2+}$-binding FYVE finger-containing phosphoinositide kinase in insulin-sensitive cells," *Molecular and Cellular Biology* 19:623-634, 1999.

Shirozu, et al., "Characterization of novel secreted and membrane proteins isolated by the signal sequence trap method," *Genomics* 37:273-280, 1996.

Smith and Harland, "Injected Xwnt-8 RNA acts early in Xenopus embryos to promote formation of a vegetal dorsalizing center," *Cell* 67:753-765, 1991.

Stark, et al., "Epithelial transformation of metanephric mesenchyme in the developing kidney regulated by Wnt-4," *Nature* 372:679-683, 1994.

Suda, et al., "Modulation of osteoclast differentiation and function by the new members of the tumor necrosis factor receptor and ligand families," *Endocrine Reviews* 20:345-357, 1999.

Thomas, et al., "Swaying is a mutant allele of the proto-oncogene Wnt-1," *Cell* 67:969-976, 1991.

Tsukamoto, et al., "Expression of the *int*-1 gene in transgenic mice is associated with mammary gland hyperplasia and adenocarcinomas in male and female mice," *Cell* 55:619-625, 1988.

Ugolini, "Differential expression assay of chromosome arm 8p genes identifies Frizzled-related (FRP1/FRZB) and Fibroblast Growth Factor Receptor 1 (FGFR1) as candidate breast cancer genes," *Oncogene* 18:1903-1910, 1999.

Uren, et al., "Secreted frizzled-related protein-1 binds directly to wingless and is a biphasic modulator of wnt signaling," *J. Biol. Chem.* 275: 4374-4382, 2000.

Vainio, et al., "Female development in mammals is regulated by Wnt-4 signalling," *Nature* 397:405-409, 1999.

Van Leeuwen, et al., "Biological activity of soluble wingless protein in cultured *Drosophila* imaginal disc cells," *Nature* 368:342-344, 1994.

Vinson and Adler, "Directional non-cell autonomy and the transmission of polarity information by the frizzled gene of *Drosophila*," *Nature* 329:549-551, 1987.

Vinson, et al., "A *Drosophila* tissue polarity locus encodes a protein containing seven potential transmembrane domains," *Nature* 338:263-264, 1989.

Wang, et al., "Frzb, a secreted protein expressed in the Spemann organizer, binds and inhibits Wnt-8," *Cell* 88:757-766, 1997.

Wang, et al., "A large family of putative transmembrane receptors homologous to the product of the *Drosophila* tissue polarity gene frizzled," *The Journal of Biological Chemistry* 271(8):4468-4476, 1996.

Wodarz, et al., "Mechanism of Wnt signaling in development," *Annu. Rev. Cell Dev. Biol.* 14:59-88, 1998.

Wolda, et al., "Overlapping expression of Xwnt-3A and Xwnt-1 in neural tissue of *Xenopus laevis* embryos," *Developmental Biology* 155:46-57, 1993.

Wolf, et al., "DDC-4, an apoptosis-associated gene, is a secreted frizzled relative," *FEBS* lett. 417:385-389, 1997.

Xu, et al., "Functional and biochemical interactions of Wnts with FrzA, a secreted Wnt antagonist," *Development* 125:4767-4776, 1998.

Yang, et al., "Identification of a common hyaluronan binding motif in the hyaluronan binding proteins RHAMM, CD44 and link protein," *The EMBO Journal* 13(2):286-296, 1994.

Yang-Snyder, et al., "A frizzled homolog functions in a vertebrate Wnt signaling pathway," *Curr. Biol.* 6(10):1302-1306, 1996.

Zhao, et al., "A human homologue of the *Drosophila* polarity gene frizzled has been identified and mapped to 17q21.1," *Genomics* 27:370-373, 1995.

Zhou, "Up-regulation of human secreted frizzled homolog in apoptosis and its down-regulation in breast tumors," *Int. J. Cancer* 78:95-99, 1998.

Zhou and Wang, "Upregulation of human secreted Frizzled homologue in apoptosis and its down regulation in breast tumors," EMBL Database, Apr. 9, 1998, Accession No. AF056087.

Chuman et al., "Identification of a peptide binding motif for secreted frizzled-related protein-1," *Peptides* 25:1831-1838, 2004.

Han et al., "Secreted Frizzled-related Protein 1 (SFRP1) Protects Fibroblasts from Ceramide-induced Apoptosis," *J. Biol. Chem.* 279(4):2832-2840, 2004.

Häusler et al., "Secreted Frizzled-Related Protein-1 Inhibits RNKL-Dependent Osteoclast Formation," *J. Bone and Mineral Res.*, 19(11):1873-1881:2004.

Hijikata, et al., "Induction of apoptosis of monocyte-macrophage lineage cells by 5-S-GAD," *FEBS*, 1999, 457: 405-408.

Van Der Bluijm, et al., "Integrins and Osteoclastic Resorption in Three Bone Organ Cultures: Differential Sensitivity to Synthetic Arg-Gly-Asp Peptides During Osteoclast Formation," *Journal of Bone and Mineral Research*, 1994, 9(7):1021-1028.

* cited by examiner

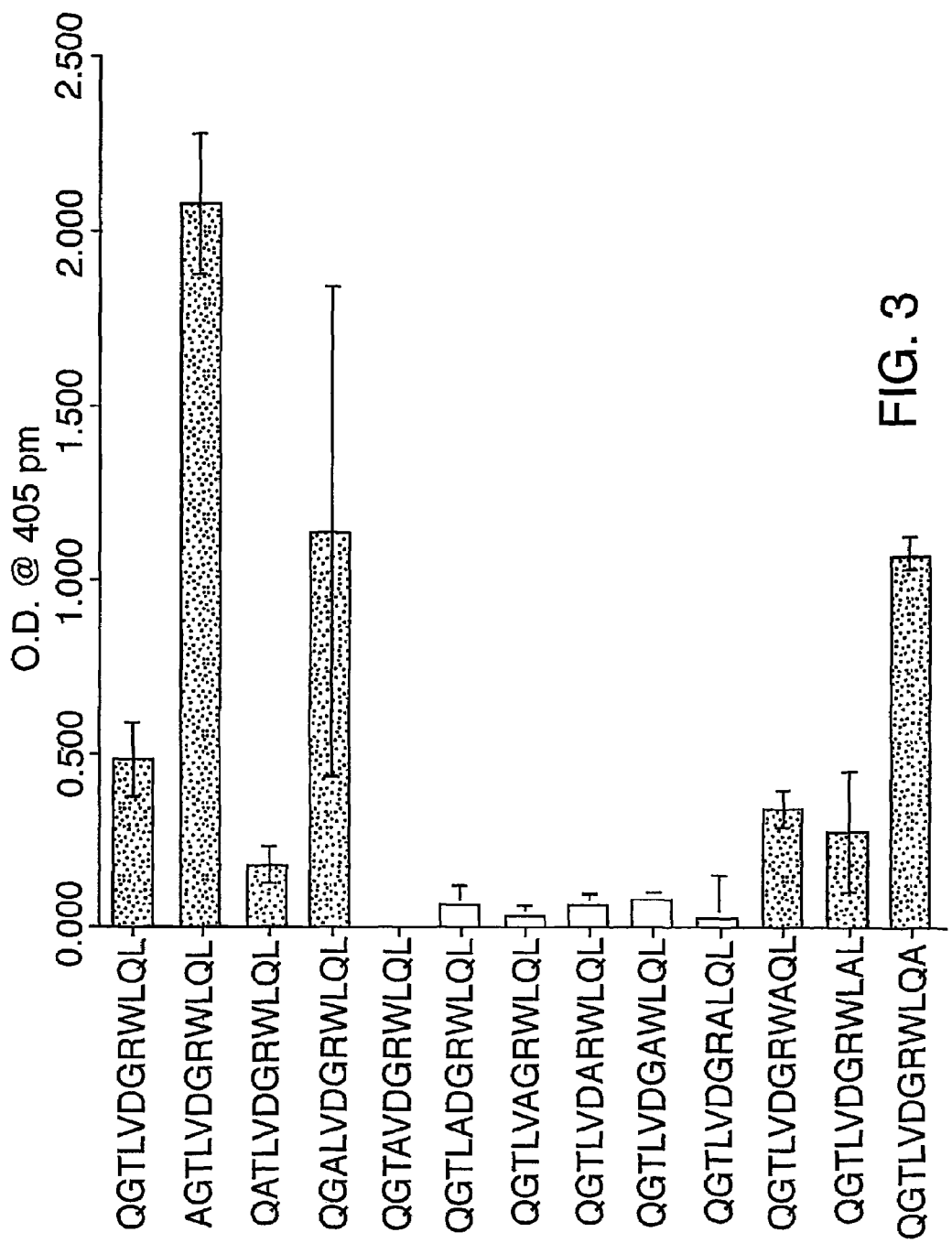

RANKL BINDING TO sFRP1 DERIVATIVES

FIG. 12

RANKL BINDING TO BACTERIAL CRD AND SCATCHARD PLOT ANALYSIS

SEQUENCE LISTING

<160> NUMBER OF SEQ ID NOS: 40

<210> SEQ ID NO 1
<211> LENGTH: 2075
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 1

```
cctgcagcct ccggagtcag tgccgcgcgc ccgccgcccc gcgccttcct gctcgccgca        60
cctccgggag ccggggcgca cccagcccgc agcgccgcct ccccgcccgc gccgcctccg       120
accgcaggcc gagggccgcc actggccggg gggaccgggc agcagcttgc ggccgcggag       180
ccgggcaacg ctggggactg cgccttttgt ccccggaggt ccctggaagt ttgcggcagg       240
acgcgcgcgg ggaggcggcg gaggcagccc cgacgtcgcg gagaacaggg cgcagagccg       300
gcatgggcat cgggcgcagc gagggggggcc gccgcgggggc cctgggcgtg ctgctggcgc       360
tgggcgcggc gcttctggcc gtgggctcgg ccagcgagta cgactacgtg agcttccagt       420
cggacatcgg cccgtaccag agcgggcgct tctacaccaa gccacctcag tgcgtggaca       480
```

```
tccccgcgga cctgcggctg tgccacaacg tgggctacaa gaagatggtg ctgcccaacc      540
tgctggagca cgagaccatg gcggaggtga agcagcaggc cagcagctgg gtgcccctgc      600
tcaacaagaa ctgccacgcc gggacccagg tcttcctctg ctcgctcttc gcgcccgtct      660
gcctggaccg gcccatctac ccgtgtcgct ggctctgcga ggccgtgcgc gactcgtgcg      720
agccggtcat gcagttcttc ggcttctact ggcccgagat gcttaagtgt gacaagttcc      780
cggaggggga cgtctgcatc gccatgacgc cgcccaatgc caccgaagcc tccaagcccc      840
aaggcacaac ggtgtgtcct ccctgtgaca acgagttgaa atctgaggcc atcattgaac      900
atctctgtgc cagcgagttt gcactgagga tgaaaataaa agaagtgaaa aagaaaatg      960 gcgacaagaa gattgtcccc aagaagaaga agcccctgaa gttggggccc atcaagaaga      1020
aggacctgaa gaagcttgtg ctgtacctga agaatgggc tgactgtccc tgccaccagc      1080
tggacaacct cagccaccac ttcctcatca tgggccgcaa ggtgaagagc cagtacttgc      1140
tgacggccat ccacaagtgg gacaagaaaa acaaggagtt caaaaacttc atgaagaaaa      1200
tgaaaaacca tgagtgcccc acctttcagt ccgtgtttaa gtgattctcc cggggcagg      1260 gtggggaggg agcctcgggt ggggtgggag cggggggac agtgcccggg aacccgtggt      1320
cacacacacg cactgccctg tcagtagtgg acattgtaat ccagtcggct tgttcttgca      1380
gcattcccgc tccctttccc tccatagcca cgctccaaac cccagggtag ccatggccgg      1440
gtaaagcaag ggccatttag attaggaagg tttttaagat ccgcaatgtg gagcagcagc      1500
cactgcacag gaggaggtga caaaccattt ccaacagcaa cacagccact aaaaacacaaa      1560 aaggggatt gggcggaaag tgagagccag cagcaaaaac tacattttgc aacttgttgg      1620
tgtggatcta ttggctgatc tatgccttc aactagaaaa ttctaatgat tggcaagtca      1680
cgttgttttc aggtccagag tagtttcttt ctgtctgctt taaatggaaa cagactcata      1740
ccacacttac aattaaggtc aagcccagaa agtgataagt gcaggagga aaagtgcaag      1800 tccattatct aatagtgaca gcaaagggac caggggagag gcattgcctt ctctgcccac      1860
agtctttccg tgtgattgtc tttgaatctg aatcagccag tctcagatgc cccaaagttt      1920
cggttcctat gagcccgggg catgatctga tccccaagac atgtggaggg gcagcctgtg      1980
cctgcctttg tgtcagaaaa aggaaaccac agtgagcctg agagagacgg cgattttcgg      2040
gctgagaagg cagtagtttt caaaacacat agtta                                2075
```

<210> SEQ ID NO 2
<211> LENGTH: 942
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 2

```
atgggcatcg ggcgcacgga ggggggccgc cgcggggcag ccctgggcgt gctgctggcg      60
ctgggcggcg cttctggccg tgggctcggc agcgagtacg actacgtgag cttccagtcg      120
gacatcggcc cgtaccagag cgggcgcttc tacaccaagc cacctcagtg cgtggacatc      180
cccgcggacc tgcggctgtg ccacaacgtg ggctacaaga gatggtgct gcccaacctg      240 ctggagcacg agaccatggc ggaggtgaag cagcaggcca gcagctgggt gcccctgctc      300
aacaagaact gccacgccgg gacccaggtc ttcctctgct cgctcttcgc gcccgtctgc      360
ctggaccggc ccatctaccc gtgtcgctgg ctctgcgagg ccgtgcgcga ctcgtgcgag      420
```

```
ccggtcatgc agttcttcgg cttctactgg cccgagatgc ttaagtgtga caagttcccg    480 gaggggggacg tctgcatcgc catgacgccg cccaatgcca ccgaagcctc caagccccaa    540
ggcacaacgg tgtgtcctcc ctgtgacaac gagttgaaat ctgaggccat cattgaacat    600
ctctgtgcca gcgagtttgc actgaggatg aaaataaaag aagtgaaaaa agaaaatggc    660
gacaagaaga ttgtcccccaa gaagaagaag cccctgaagt tggggcccat caagaagaag    720
gacctgaaga agcttgtgct gtacctgaag aatggggctg actgtccctg ccaccagctg    780
gacaacctca gccaccactt cctcatcatg ggccgcaagg tgaagagcca gtacttgctg    840
acggccatcc acaagtggga caagaaaaac aaggagttca aaacttcat gaagaaaatg    900 aaaaaccatg agtgccccac ctttcagtcc gtgtttaagt ga                       942
```

<210> SEQ ID NO 3
<211> LENGTH: 313
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 3

```
Met Gly Ile Gly Arg Thr Glu Gly Gly Arg Gly Ala Ala Leu Gly
  1               5                  10                  15

Val Leu Leu Ala Leu Gly Gly Ala Ser Gly Arg Gly Leu Gly Ser Glu
                 20                  25                  30

Tyr Asp Tyr Val Ser Phe Gln Ser Asp Ile Gly Pro Tyr Gln Ser Gly
             35                  40                  45

Arg Phe Tyr Thr Lys Pro Pro Gln Cys Val Asp Ile Pro Ala Asp Leu
         50                  55                  60

Arg Leu Cys His Asn Val Gly Tyr Lys Lys Met Val Leu Pro Asn Leu
 65                  70                  75                  80

Leu Glu His Glu Thr Met Ala Glu Val Lys Gln Gln Ala Ser Ser Trp
                 85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
    210                 215                 220

Val Pro Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270
```

Lys Val Lys Ser Gln Tyr Leu Leu Thr Ala Ile His Lys Trp Asp Lys
            275                 280                 285

Lys Asn Lys Glu Phe Lys Asn Phe Met Lys Lys Met Lys Asn His Glu
            290                 295                 300

Cys Pro Thr Phe Gln Ser Val Phe Lys
305                 310

<210> SEQ ID NO 4
<211> LENGTH: 338
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 4

Met Gly Ile Gly Arg Thr Glu Gly Gly Arg Gly Ala Ala Leu Gly
1               5                   10                  15

Val Leu Leu Ala Leu Gly Gly Ala Ser Gly Arg Gly Leu Gly Ser Glu
                20                  25                  30

Tyr Asp Tyr Val Ser Phe Gln Ser Asp Ile Gly Pro Tyr Gln Ser Gly
            35                  40                  45

Arg Phe Tyr Thr Lys Pro Pro Gln Cys Val Asp Ile Pro Ala Asp Leu
    50                  55                  60

Arg Leu Cys His Asn Val Gly Tyr Lys Lys Met Val Leu Pro Asn Leu
65                  70                  75                  80

Leu Glu His Glu Thr Met Ala Glu Val Lys Gln Ala Ser Ser Trp
                85                  90                  95

Val Pro Leu Leu Asn Lys Asn Cys His Ala Gly Thr Gln Val Phe Leu
                100                 105                 110

Cys Ser Leu Phe Ala Pro Val Cys Leu Asp Arg Pro Ile Tyr Pro Cys
            115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
    195                 200                 205

Arg Met Lys Ile Lys Glu Val Lys Lys Glu Asn Gly Asp Lys Lys Ile
210                 215                 220

Val Pro Lys Lys Lys Pro Leu Lys Leu Gly Pro Ile Lys Lys Lys
225                 230                 235                 240

Asp Leu Lys Lys Leu Val Leu Tyr Leu Lys Asn Gly Ala Asp Cys Pro
                245                 250                 255

Cys His Gln Leu Asp Asn Leu Ser His His Phe Leu Ile Met Gly Arg
            260                 265                 270

Lys Val Lys Ser Gln Tyr Leu Leu Thr Ala Ile His Lys Trp Asp Lys
    275                 280                 285

Lys Asn Lys Glu Phe Lys Asn Phe Met Lys Lys Met Lys Asn His Glu
290                 295                 300

Cys Pro Thr Phe Gln Ser Val Phe Lys Gln Ala Tyr Val Glu Gln Lys

```
                305                 310                 315                 320
Leu Ile Ser Glu Glu Asp Leu Asn Ser Ala Val Asp His His His
                    325                 330                 335

His His

<210> SEQ ID NO 5
<211> LENGTH: 195
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 5

Met Gly Ile Gly Arg Thr Glu Gly Gly Arg Gly Ala Ala Leu Gly
  1               5                  10                  15

Val Leu Ala Leu Gly Gly Ala Ser Gly Arg Gly Leu Gly Ser Glu
                 20                  25                  30

Tyr Asp Tyr Val Ser Phe Gln Ser Asp Ile Gly Pro Tyr Gln Ser Gly
             35                  40                  45

Arg Phe Tyr Thr Lys Pro Pro Gln Cys Val Asp Ile Pro Ala Asp Leu
 50                  55                  60

Arg Leu Cys His Asn Val Gly Tyr Lys Lys Met Val Leu Pro Asn Leu
 65                  70                  75                  80

Leu Glu His Glu Thr Met Ala Glu Val Lys Gln Gln Ala Ser Ser Trp
                 85                  90                  95

Val Pro Leu Leu Asn Lys Asn Cys His Ala Gly Thr Gln Val Phe Leu
                100                 105                 110

Cys Ser Leu Phe Ala Pro Val Cys Leu Asp Arg Pro Ile Tyr Pro Cys
            115                 120                 125

Arg Trp Leu Cys Glu Ala Val Arg Asp Ser Cys Glu Pro Val Met Gln
130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Gln Ala Tyr Val Glu Gln
                165                 170                 175

Lys Leu Ile Ser Glu Glu Asp Leu Asn Ser Ala Val Asp His His His
            180                 185                 190

His His His
        195

<210> SEQ ID NO 6
<211> LENGTH: 246
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 6

Met Gly Ile Gly Arg Thr Glu Gly Gly Arg Gly Ala Ala Leu Gly
  1               5                  10                  15

Val Leu Ala Leu Gly Gly Ala Ser Gly Arg Gly Leu Gly Ser Glu
                 20                  25                  30

Tyr Asp Tyr Val Ser Phe Gln Ser Asp Ile Gly Pro Tyr Gln Ser Gly
             35                  40                  45

Arg Phe Tyr Thr Lys Pro Pro Gln Cys Val Asp Ile Pro Ala Asp Leu
 50                  55                  60
```

```
Arg Leu Cys His Asn Val Gly Tyr Lys Lys Met Val Leu Pro Asn Leu
 65                  70                  75                  80

Leu Glu His Glu Thr Met Ala Glu Val Lys Gln Gln Ala Ser Ser Trp
                 85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175

Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Gln Ala Tyr
    210                 215                 220

Val Glu Gln Lys Leu Ile Ser Glu Glu Asp Leu Asn Ser Ala Val Asp
225                 230                 235                 240

His His His His His His
            245

<210> SEQ ID NO 7
<211> LENGTH: 267
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 7

Met Gly Ile Gly Arg Thr Glu Gly Gly Arg Gly Ala Ala Leu Gly
  1               5                  10                  15

Val Leu Leu Ala Leu Gly Gly Ala Ser Gly Arg Gly Leu Gly Ser Glu
                 20                  25                  30

Tyr Asp Tyr Val Ser Phe Gln Ser Asp Ile Gly Pro Tyr Gln Ser Gly
             35                  40                  45

Arg Phe Tyr Thr Lys Pro Pro Gln Cys Val Asp Ile Pro Ala Asp Leu
     50                  55                  60

Arg Leu Cys His Asn Val Gly Tyr Lys Lys Met Val Leu Pro Asn Leu
 65                  70                  75                  80

Leu Glu His Glu Thr Met Ala Glu Val Lys Gln Gln Ala Ser Ser Trp
                 85                  90                  95

Val Pro Leu Leu Asn Lys Asn Cys His Ala Gly Thr Gln Val Phe Leu
            100                 105                 110

Cys Ser Leu Phe Ala Pro Val Cys Leu Asp Arg Pro Ile Tyr Pro Cys
        115                 120                 125

Arg Trp Leu Cys Glu Ala Val Arg Asp Ser Cys Glu Pro Val Met Gln
    130                 135                 140

Phe Phe Gly Phe Tyr Trp Pro Glu Met Leu Lys Cys Asp Lys Phe Pro
145                 150                 155                 160

Glu Gly Asp Val Cys Ile Ala Met Thr Pro Pro Asn Ala Thr Glu Ala
                165                 170                 175
```

```
                165                 170                 175
Ser Lys Pro Gln Gly Thr Thr Val Cys Pro Pro Cys Asp Asn Glu Leu
            180                 185                 190

Lys Ser Glu Ala Ile Ile Glu His Leu Cys Ala Ser Glu Phe Ala Leu
        195                 200                 205

Arg Met Lys Ile Lys Glu Val Lys Lys Glu Asn Gly Asp Lys Lys Ile
    210                 215                 220

Val Pro Lys Lys Lys Pro Leu Lys Leu Gly Pro Ile Lys Lys Lys
225                 230                 235                 240

Asp Leu Gln Ala Tyr Val Glu Gln Lys Leu Ile Ser Glu Glu Asp Leu
            245                 250                 255

Asn Ser Ala Val Asp His His His His His His
            260                 265

<210> SEQ ID NO 8
<211> LENGTH: 229
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 8

Met Gly Ile Gly Arg Thr Glu Gly Gly Arg Gly Ala Ala Leu Gly
1               5                   10                  15

Val Leu Ala Leu Gly Gly Ala Ser Gly Arg Gly Leu Gly Ser Glu
            20                  25                  30

Tyr Asp Tyr Val Ser Phe Gln Ser Asp Ile Gly Pro Tyr Gln Ser Gly
        35                  40                  45

Arg Phe Tyr Thr Lys Pro Pro Gln Ile Ala Met Thr Pro Pro Asn Ala
    50                  55                  60

Thr Glu Ala Ser Lys Pro Gln Gly Thr Thr Val Cys Pro Pro Cys Asp
65                  70                  75                  80

Asn Glu Leu Lys Ser Glu Ala Ile Ile Glu His Leu Cys Ala Ser Glu
                85                  90                  95

Phe Ala Leu Arg Met Lys Ile Lys Glu Val Lys Lys Glu Asn Gly Asp
            100                 105                 110

Lys Lys Ile Val Pro Lys Lys Lys Pro Leu Lys Leu Gly Pro Ile
        115                 120                 125

Lys Lys Lys Asp Leu Lys Lys Leu Val Leu Tyr Leu Lys Asn Gly Ala
    130                 135                 140

Asp Cys Pro Cys His Gln Leu Asp Asn Leu Ser His Phe Leu Ile
145                 150                 155                 160

Met Gly Arg Lys Val Lys Ser Gln Tyr Leu Leu Thr Ala Ile His Lys
                165                 170                 175

Trp Asp Lys Lys Asn Lys Glu Phe Lys Asn Phe Met Lys Lys Met Lys
            180                 185                 190

Asn His Glu Cys Pro Thr Phe Gln Ser Val Phe Lys Gln Ala Tyr Val
        195                 200                 205

Glu Gln Lys Leu Ile Ser Glu Glu Asp Leu Asn Ser Ala Val Asp His
    210                 215                 220

His His His His
225

<210> SEQ ID NO 9
<211> LENGTH: 7
```

```
<212> TYPE: PRT
<213> ORGANISM: Artificial Sequence
<220> FEATURE:
<223> OTHER INFORMATION: Primer/Probe sequence
<220> FEATURE:
<221> NAME/KEY: MISC_FEATURE
<222> LOCATION: (1)..(1)
<223> OTHER INFORMATION: Xaa = Val or Leu
<220> FEATURE:
<221> NAME/KEY: MISC_FEATURE
<222> LOCATION: (7)..(7)
<223> OTHER INFORMATION: Xaa = Val or Leu

<400> SEQUENCE: 9

Xaa Val Asp Gly Arg Trp Xaa
  1               5

<210> SEQ ID NO 10
<211> LENGTH: 12
<212> TYPE: PRT
<213> ORGANISM: Homo sapiens

<400> SEQUENCE: 10

Val Val Asp Gly Arg Phe Val Leu Lys Ile Thr Asp
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 11

Val Val Asp Gly Arg Trp Val Gln Gly Leu Glu Asp
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 12

Asn Gln Gly Arg Asp Val Pro Glu Arg Trp Ser Lys
  1               5                  10

<210> SEQ ID NO 13
<211> LENGTH: 141
<212> TYPE: PRT
<213> ORGANISM: Homo sapiens

<400> SEQUENCE: 13

Cys Ile Ala Met Thr Pro Pro Asn Ala Thr Glu Ala Ser Lys Pro Gln
  1               5                  10                  15

Gly Thr Thr Val Cys Pro Pro Cys Asp Asn Glu Leu Lys Ser Glu Ala
             20                  25                  30

Ile Ile Glu His Leu Cys Ala Ser Glu Phe Ala Leu Arg Met Lys Ile
         35                  40                  45

Lys Glu Val Lys Lys Glu Asn Gly Asp Lys Lys Ile Val Pro Lys Lys
     50                  55                  60

Lys Lys Pro Leu Lys Leu Gly Pro Ile Lys Lys Lys Asp Leu Lys Lys
 65                  70                  75                  80
```

```
Leu Val Leu Tyr Leu Lys Asn Gly Ala Asp Cys Pro Cys His Gln Leu
                85                  90                  95

Asp Asn Leu Ser His His Phe Leu Ile Met Gly Arg Lys Val Lys Ser
            100                 105                 110

Gln Tyr Leu Leu Thr Ala Ile His Lys Trp Asp Lys Lys Asn Lys Glu
            115                 120                 125

Phe Lys Asn Phe Met Lys Met Lys Asn His Glu Cys
        130                 135                 140

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 14

Gln Gly Thr Leu Val Asp Gly Arg Trp Leu Gln Leu
  1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 15

Ala Gly Thr Leu Val Asp Gly Arg Trp Leu Gln Leu
  1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 16

Gln Ala Thr Leu Val Asp Gly Arg Trp Leu Gln Leu
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 17

Gln Gly Ala Leu Val Asp Gly Arg Trp Leu Gln Leu
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 18
```

Gln Gly Thr Ala Val Asp Gly Arg Trp Leu Gln Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 19

Gln Gly Thr Leu Ala Asp Gly Arg Trp Leu Gln Leu
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 20

Gln Gly Thr Leu Val Ala Gly Arg Trp Leu Gln Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 21

Gln Gly Thr Leu Val Asp Ala Arg Trp Leu Gln Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 22

Gln Gly Thr Leu Val Asp Gly Ala Trp Leu Gln Leu
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 23

Gln Gly Thr Leu Val Asp Gly Arg Ala Leu Gln Leu
1               5                   10

<210> SEQ ID NO 24
<211> LENGTH: 12
<212> TYPE: PRT
<213> ORGANISM: Artificial Sequence -continued

```
<220> FEATURE:
<223> OTHER INFORMATION: Description of Artificial Sequence: Primer/
      Probe sequence

<400> SEQUENCE: 24

Gln Gly Thr Leu Val Asp Gly Arg Trp Ala Gln Leu
  1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 25

Gln Gly Thr Leu Val Asp Gly Arg Trp Leu Ala Leu
  1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 26

Gln Gly Thr Leu Val Asp Gly Arg Trp Leu Gln Ala
  1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 27

Leu Val Asp Gly Arg Trp Leu Tyr Asn Pro His His
  1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 28

Met Val Asp Gly Ser Trp Leu Asp Leu
  1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 29

Thr Leu Cys Pro Val Asp Gly Arg Trp
  1               5
```

```
<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 30
agccttggca gtcaacgacg                                              20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 31
gttgtggctt ttgcattgca c                                            21

<210> SEQ ID NO 32
<211> LENGTH: 14
<212> TYPE: DNA
<213> ORGANISM: Artificial Sequence
<220> FEATURE:
<223> OTHER INFORMATION: Primer/Probe sequence
<220> FEATURE:
<221> NAME/KEY: misc_feature
<222> LOCATION: (13)..(13)
<223> OTHER INFORMATION: n = any residue

<400> SEQUENCE: 32
tttttttttt ttna                                                    14

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 33
atgaggtcca ccaccctgtt                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 34
catggagaag gctggggctc                                              20

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 35
```

```
tgttgaaaac tagtagctg                                                    19

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 36
gctgtgggca aggtcatccc                                                   20

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 37
cttgattgcc                                                              10

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 38
ttaaaattgc tgcctgcctg ag                                                22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Primer/
      Probe sequence

<400> SEQUENCE: 39
tccgaactac agggacaaca gg                                                22

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Primer/
      Probe sequence

<400> SEQUENCE: 40

Trp Glu Cys Ala Met Tyr Asp Gly Arg Cys Leu Thr
 1               5                  10
```

SFRP AND PEPTIDE MOTIFS THAT INTERACT WITH SFRP AND METHODS OF THEIR USE

CROSS REFERENCE TO RELATED APPLICATIONS

This is the U.S. National Stage of International Application No. PCT/US02/00869, filed Jan. 10, 2002, which was published in English under PCT Article 21(2), which in turn claims the benefit of U.S. Provisional Application No. 60/260,908, filed Jan. 10, 2001. Both applications are incorporated herein in their entirety.

FIELD OF THE DISCLOSURE

This disclosure relates to osteoclast differentiation, specifically to a peptide motif and proteins containing the motif that are capable of binding to secreted Frizzled-related protein family members.

BACKGROUND

Bone remodeling, a process responsible for the continuous renewal of the adult human skeleton, is carried out by osteoclasts and osteoblasts, two specialized cell types that originate from hematopoietic and mesenchymal progenitors of the bone marrow, respectively. A continuous and orderly supply of these cells is essential for skeletal homeostasis, as increased or decreased production of osteoclasts or osteoblasts and/or changes in the rate of their apoptosis are largely responsible for the imbalance between bone resorption and formation that underlies several systemic or localized bone diseases.

Enhanced osteoclast activity plays a major role in the pathogenesis of postmenopausal osteoporosis, Paget's disease, lytic bone metastases, multiple myeloma, hyperparathyroidisn, rheumatoid arthritis, periodontitis, and hypercalcemia of malignancy. These clinical problems are associated with significant morbidity or mortality, and affect more than 10 million patients in the United States. However, only a limited number of agents that inhibit osteoclast formation or bone resorption are available and for most their mechanisms of action are unknown. Furthermore, many of these agents have significant side effects that limit their utility. Thus, there exists a need for the identification and characterization of inhibitors of osteoclast formation and bone resorption as part of the continuing search to provide therapeutic benefits for these patients.

Conversely, decreased osteoclast activity plays a major role in the pathogenesis of osteopetrosis, Albright's osteodystrophy, and achondroplasia, for which there is no specific therapy. Thus, there also exists a need for the identification and characterization of treatments that enhance osteoclast formation and bone resorption in order to provide successful therapies for these patients.

Identification of the mechanisms involved in bone disorders is crucial for the understanding of bone physiology. While numerous genes and gene families (and the polypeptides encoded by them) that participate in the regulation of bone cells have been identified and cloned, their functions have not been clearly delineated due to the complexities of the bone formation pathways. A great need exists for the definitive identification of targets for the treatment of bone disorders, including bone resorption disorders such as postmenopausal osteopor sis, Paget's disease, lytic bone metastases, multiple myeloma, rheumatoid arthritis, hypercalcemia of malignancy, osteopetrosis, Albright's osteodystrophy, and achondroplasia.

SUMMARY OF TIRE DISCLOSURE

Disclosed herein are proteins that bind to secreted Frizzled-related protein-1 (-sFRP-1). In one embodiment, the sFRP-1 binding peptide is a purified peptide. In particular examples, the peptide is selected from the group consisting of: (a) the amino acid sequence shown in SEQ ID NO: 9; (b) at least one conservative amino acid substitution of the amino acid sequence shown in (a); and (c) an amino acid sequence that shares at least 80% sequence identity with the sequence shown in (a), wherein the protein retains the ability to bind to sFRP. In another embodiment, the peptide has a sequence as shown in the formula:

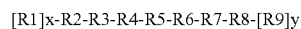

wherein x and y are integers independently selected from the group 0 or 1; R3 is selected from the group Val (V), Ala (A) or conservative substitutions therefor; R4 is selected from the group consisting of Asp (D), Ala (A) or conservative substitutions therefor; R5 is selected from the group consisting of Gly (G), Ala (A) or conservative substitutions therefor; R6 is selected from the group consisting of Arg (R) Ala (A) or conservative substitutions therefor; R7 is selected from the group consisting of Trp (W), Ala (A) or conservative substitutions therefor. Nucleic acids encoding these peptides are provided, as are vectors containing the nucleic acids and host cells transformed with these vectors. Methods for screening for agents that interfere with or mimic the interaction of these peptides and sFRP are also disclosed.

In another embodiment, a method is disclosed for enhancing osteoclast differentiation. In one specific, non-limiting example the method includes administering a therapeutically effective amount of the purified peptides disclosed herein (or effective fragments, fusions or mimetics) to a subject in order to enhance osteoclast differentiation.

In a further embodiment, a method is provided for inhibiting osteoclast formation in a subject. The method includes administering to the subject a therapeutically effective amount of sFRP-1 (SEQ ID NO: 3), fragments of SEQ ID NO: 3, or fusions or variants of SEQ ID NO: 3, to a subject, wherein the polypeptide binds to a RANKL molecule as set forth as GenBank Accession No. AF013171, GenBank Accession No. AF019047, or GenBank Accession No. AF053712, or another TNF family member.

In yet another embodiment, a method is provided for modulating T cell activity. In one specific, non-limiting example, the method includes administering a therapeutically effective amount of the purified sFRP-1-binding peptides disclosed herein to a subject in order to modulate T cell activity.

BRIEF DESCRIPTION OF THE FIGURES

FIG. 3 is a graph showing the results from binding assays of alanine substituted A-C2 (SEQ ID NO: 14)/alkaline phosphatase fusion proteins to sFRP-1 (SEQ ID NO: 3) in an ELISA. The bar graph indicates the mean +/−S.D. of triplicate measurements from a single representative experiment. A parallel analysis of these samples in wells coated with monoclonal antibody to the FLAG epitope indicated that the concentration of chimera in the different broths was similar.

FIG. 4 is a set of diagrams showing a calorimetric analysis of the interaction between AC2 peptide and sFRP-1.

FIG. 6 is a set of graphs showing that sFRP-1 inhibits osteoclast formation in two different experimental models.

FIG. 7 is a pair of graphs showing that sFRP-1 antiserum stimulates osteoclast formation in co-cultures of primary osteoblasts and adult spleen cells.

µg/mL, 1 µg/mL, and 0.5 µg/mL of A-C2 (SEQ ID NO: 14) respectively. Stimulation was observed when T cells were added to the cultures (FIG. 15A) as compared to when T cells were not added to the cultures (FIG. 15B).

Figure 12:
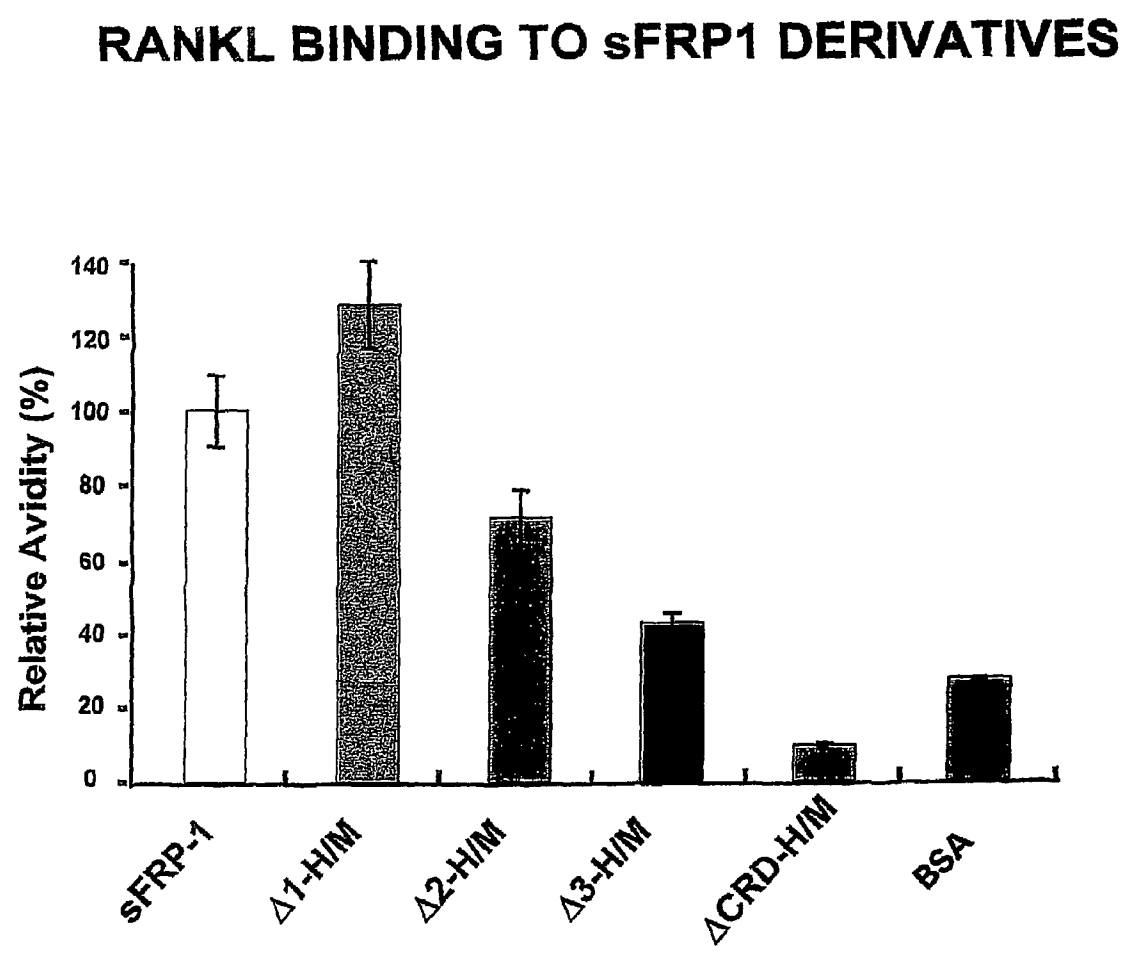

FIG. 12 is a graph of the binding avidity of several sFRP-1 deletion mutants for RANKL in ELISA experiments. Wells were coated either with full-length sFRP-1 or with any one of a set of epitope-tagged sFRP-1 deletion mutants (Uren et al., *J Biol Chem* 275:4374-4382, 2000) or BSA control, and then sequentially incubated with soluble RANKL and reagents to detect RANKL bound to the wells. The results shown are the mean +/−S.D. of triplicate measurements from a representative experiment.

FIG. 13 is a set of four graphs showing that binding of RANKL to bacterially expressed CRD in ELISA experiments is strong and may have two affinities. FIG. 13A is a graph showing the binding of RANKL to wells coated with the CRD. Optical density in the wells is a measure of the amount of RANKL retained in the wells and is plotted as a function of the soluble RANKL concentration incubated in the wells. FIG. 13B is a Scatchard plot of the RANKL binding data shown in FIG. 13A. The binding appears to be characterized by more than one affinity. FIG. 13C is a reformatting of the Scatchard analysis of FIG. 13B, pertaining to a putative higher-affinity binding site. FIG. 13D is a reformatting of the Scatchard analysis of FIG. 13B, pertaining to a putative lower-affinity binding site.

Figure 14A:
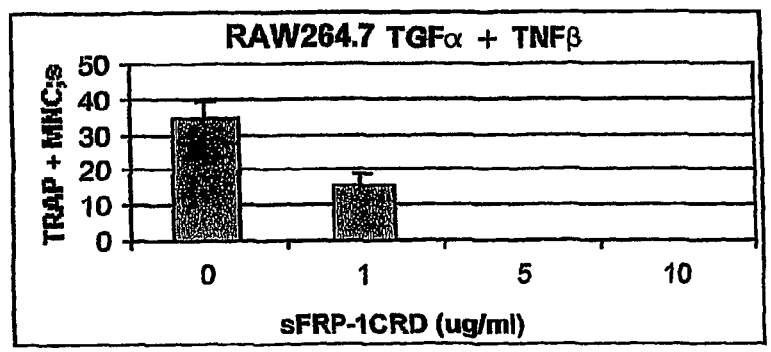
Figure 14B:
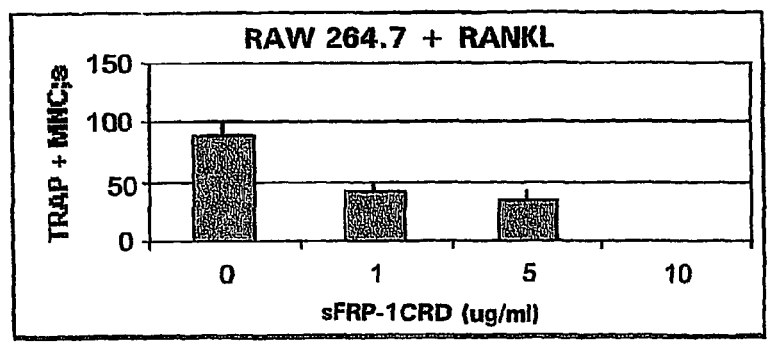
Figure 14C:
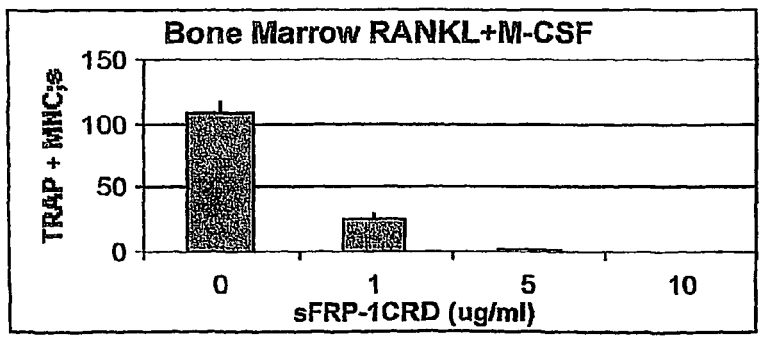

FIG. 14 is a set of three graphs showing that the bacterially expressed CRD of sFRP-1 inhibits osteoclast formation in a variety of experimental models, including one that is not dependent on RANKL. These were: (1) RAW264.7+TNFα+ TGFβ (FIG. 14A; Horwood et al., *Journal of Immunology* 166:4915-4921, 2001; Quinn et al., *Journal of Bone and Mineral Research*. 16, 1787-1794, 2001 (2) the macrophage/monocyte cell line RAW264.7+ RANKL (FIG. 14B), and (3) bone marrow cells+RANKL+M-CSF (FIG. 14C). In each system, both RANKL-dependent (FIG. 14B and FIG. 14C) and RANKL-independent (FIG. 14A, TNFα-dependent osteoclast formation), the bacterially expressed CRD mimicked the action of full-length sFRP-1 and with similar potency.

Figure 15:
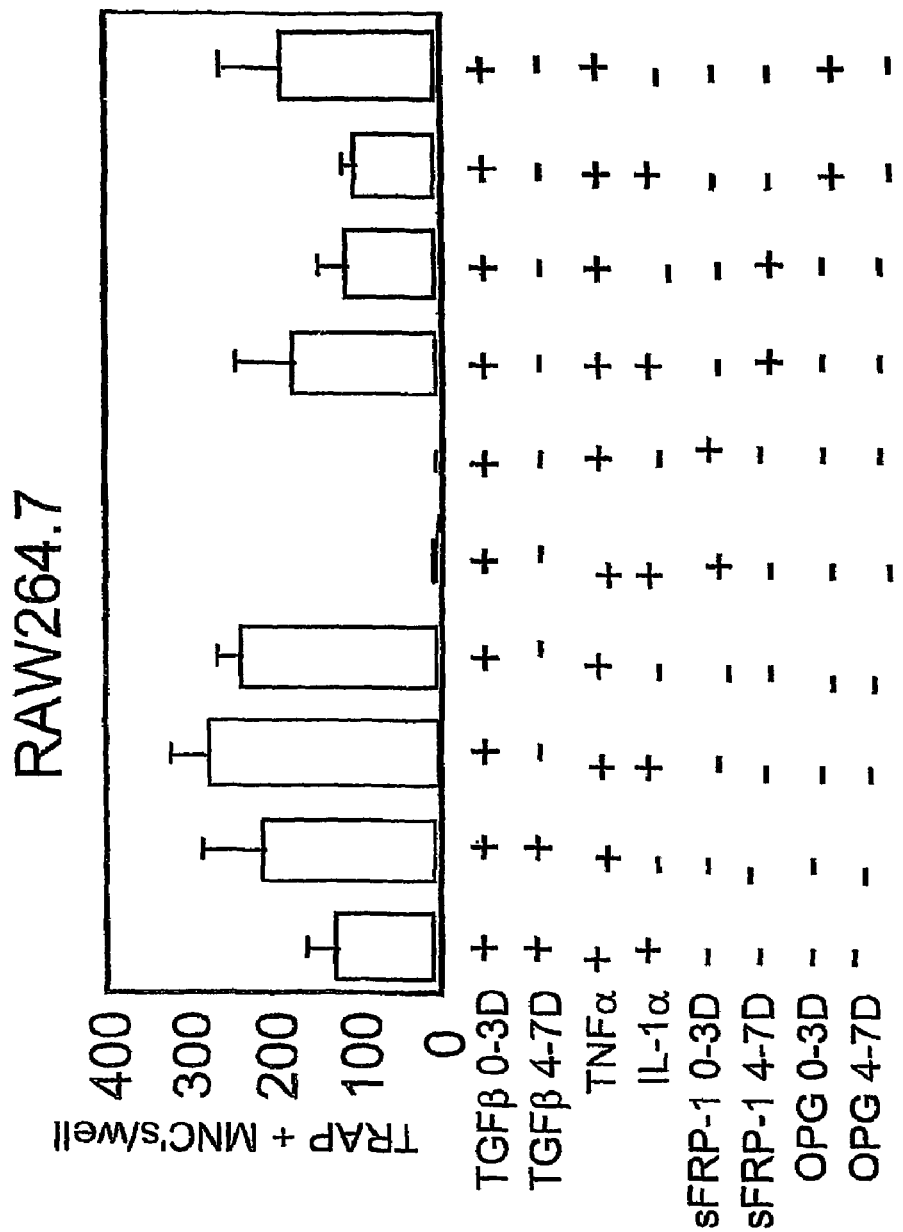

FIG. 15 is a graph showing that sFRP-1 can inhibit osteoclast formation in RAW264.7 cells treated with a combination of cytokines that includes TNFα, but not RANKL. The effect of sFRP-1 was assessed upon a RANKL-independent method of osteoclast formation using the monocyte/macrophage cell line RAW264.7 (Quinn et al., *Journal of Bone and Mineral Research*. 16, 1787-1794, 2001) and was compared with that of osteoprotegerin. TGFα was added during the first three days of culture to increase osteoclast numbers. sFRP-1 inhibited TNFα-dependent osteoclast formation when present during the first three days of culture, whilst OPG had no effect suggesting that sFRP-1 was acting independently of RANKL, through binding to TNFα or through WNT signaling.

Figure 16:
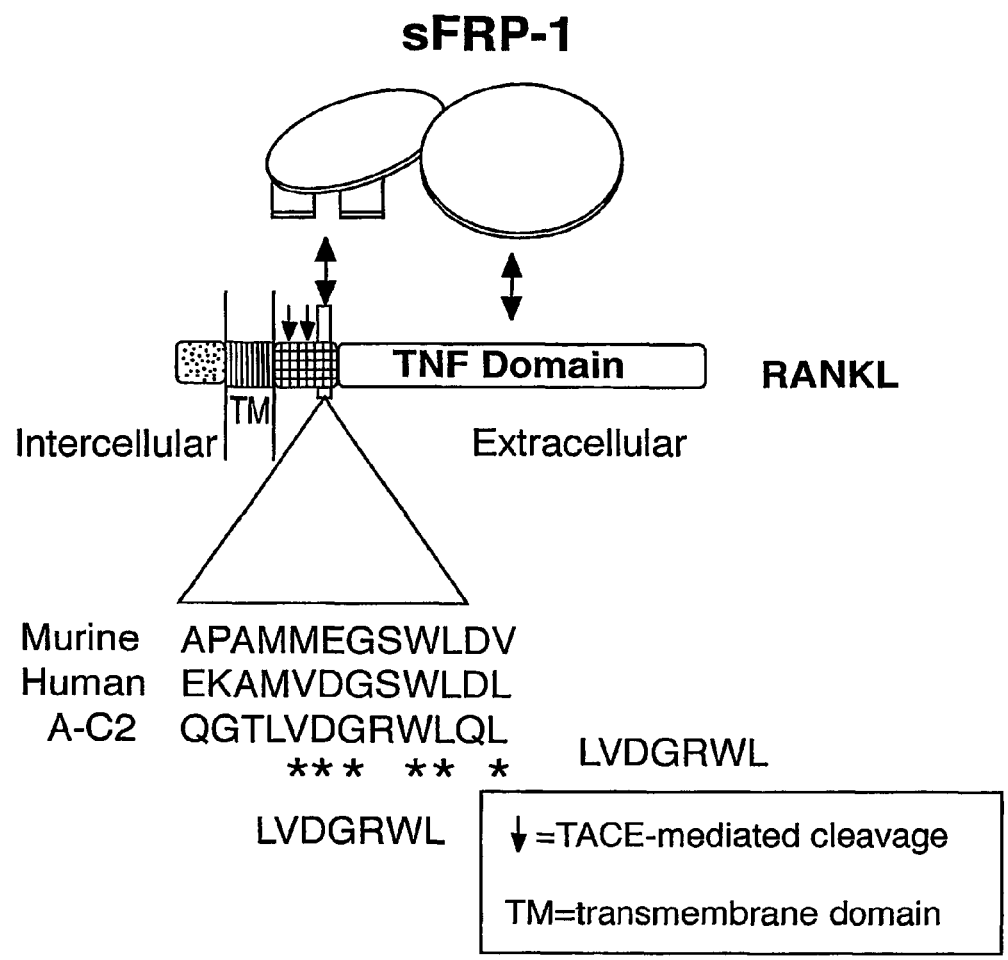

FIG. 16 is a schematic diagram of one possible mechanism of sFRP-1 (SEQ ID NO: 3)/RANKL binding. Note that the sFRP-1 binding motif in the RANKL sequence is located just downstream from TACE cleavage sites (arrows). TACE is the TNFα converting enzyme, which is known to process RANKL (L. Lum et al., *J. Biol. Chem*. 274:13613-13618, 1999). sFRP-1 binding to RANKL could alter the processing of RANKL by TACE, which in turn could alter RANKL activity.

Figure 17:
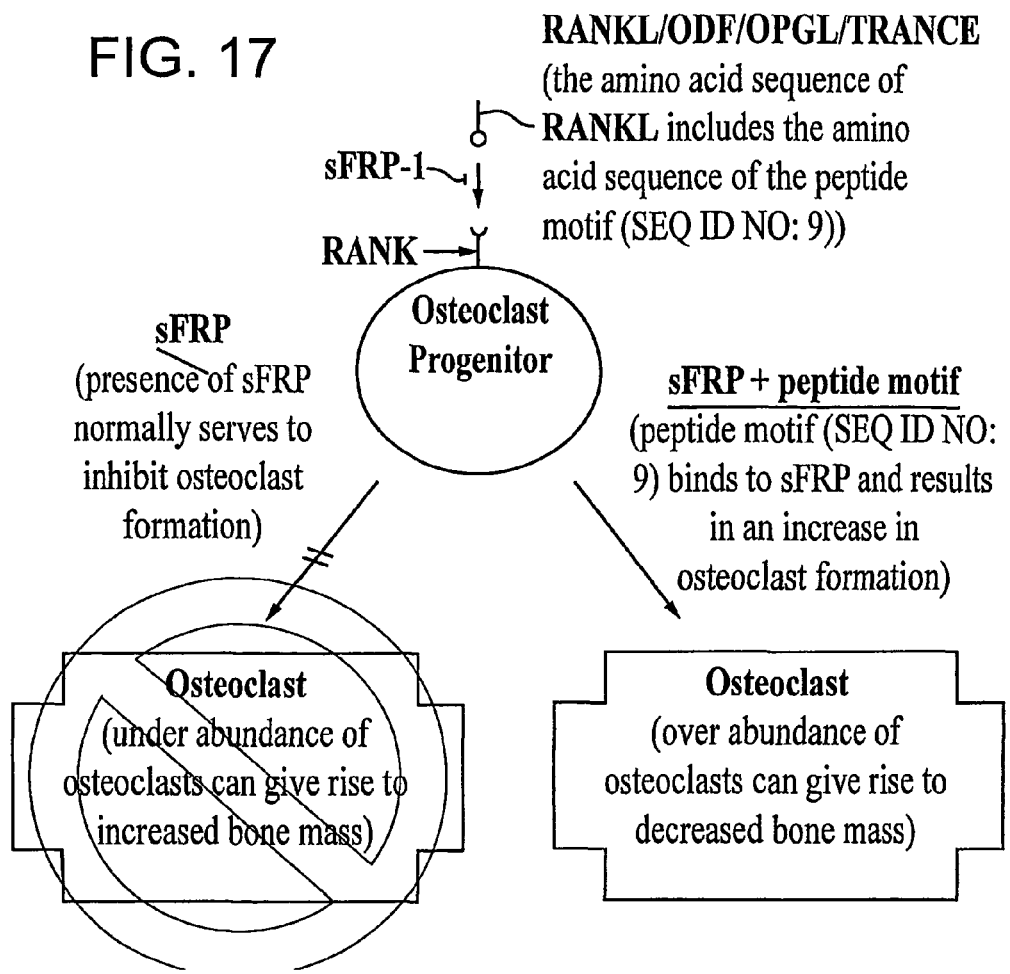

FIG. 17 is a diagram showing one possible model of sFRP-1's role in osteoclast formation. An osteoclast-supporting cell expressing RANKL interacts with sFRP-1 (SEQ ID NO: 3) resulting in the inhibition of osteoclast formation. When the peptide motif (SEQ ID NO: 9) is added to the solution it binds to sFRP-1 (SEQ ID NO: 3) and promotes osteoclast differentiation.

SEQUENCE LISTING

The nucleic and amino acid sequences listed in the accompanying sequence listing are shown using standard letter abbreviations for nucleotide bases, and three-letter code for amino acids. Only one strand of each nucleic acid sequence is shown, but the complementary strand is understood as included by any reference to the displayed strand.

SEQ ID NO: 1 shows the cDNA sequence of human sFRP-1.

SEQ ID NO: 2 shows the nucleic acid sequence of the human sFRP-1 open reading frame.

SEQ ID NO: 3 shows the amino acid sequence of human sFRP-1.

SEQ ID NO: 4 shows the amino acid sequence of human sFRP-1-M/H.

SEQ ID NO: 5 shows the amino acid sequence of human sFRP-Δ1-M/H.

SEQ ID NO: 6 shows the amino acid sequence of human sFRP-Δ2-M/H.

SEQ ID NO: 7 shows the amino acid sequence of human sFRP-Δ3-M/H.

SEQ ID NO: 8 shows the amino acid sequence of human sFRP-ΔCRD-M/H.

SEQ ID NO: 9 shows the amino acid sequence of the peptide motif.

SEQ ID NO: 10 shows the peptide motif from ANP receptor A (human).

SEQ ID NO: 11 shows the amino acid sequence of the A-E4 peptide.

SEQ ID NO: 12 shows the amino acid sequence of the A-F7 peptide.

SEQ ID NO: 13 shows the amino acid sequence of the netrin homology domain of sFRP-1.

SEQ ID NO: 14 shows the amino acid sequence of the A-C2 peptide.

SEQ ID NO: 15-26 show peptides generated for use in alanine scanning experiments.

SEQ ID NO: 27 shows the amino acid sequence of B-B9.

SEQ ID NO: 28 shows an amino acid sequence found in RANKL that contains a sequence similar to that of SEQ ID NO: 9.

SEQ ID NO: 29 shows an amino acid sequence found in a netrin receptor that contains a sequence similar to that of SEQ ID NO: 9.

SEQ ID NOS: 30-39 show the nucleic acid sequences of various primers and probes used in PCR and hybridization experiments.

SEQ ID NO: 40 shows the amino acid sequence of the A-D9 peptide.

DETAILED DESCRIPTION

I. Abbreviations
BSA: bovine serum albumin
CRD: cysteine-rich domain
ELISA: enzyme-linked immunosorbent assay
HSPG: heparin-sulfate proteoglycan
mAb: monoclonal antibody
MDCK: Madin-Darby canine kidney
M/H: Myc-His epitope tags
PAGE: polyacrylamide gel electrophoresis PBS: phosphate-buffered saline
sFRP: secreted Frizzled-related protein
Wnt: Wnt proteins II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terns are provided:

Abnormal: Deviation from normal characteristics. Normal characteristics can be found in a control, a standard for a population, etc. For instance, where the abnormal condition is a disease condition, such as osteoporosis (characterized by a decrease in bone mass), a few appropriate sources of normal characteristics might include an individual who is not suffering from the disease (e.g. osteoporosis), a population standard of individuals believed not to be suffering from the disease, etc.

Likewise, abnormal can refer to a condition that is associated with a disease. The term "associated with" includes an increased risk of developing the disease as well as the disease itself. For instance, a certain abnormality (such as a decrease in the expression of sFRP, which in turn upregulates osteoclast formation) can be described as being associated with the biological condition of osteoporosis (decrease in bone mass); thus, the abnormality is predictive both of an increased risk of developing osteoporosis and of the presence of osteoporosis.

Abnormal protein expression, such as abnormal sFRP protein expression, refers to expression of a protein that is in some manner different from expression of the protein in a normal (wildtype) situation. This includes but is not necessarily limited to: (1) a mutation in the protein such that one or more of the amino acid residues is different, (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of a decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in post translational processing; and (9) alteration of the localized (e.g. organ or tissue specific) expression of the protein (such that the protein is not expressed where it would normally be expressed or is expressed where it normally would not be expressed), each compared to a control or standard.

Controls or standards appropriate for comparison to a sample, for the determination of abnormality, include samples believed to be normal as well as laboratory values, even though possibly arbitrarily set, keeping in mind that such values can vary from laboratory to laboratory. Laboratory standards and values can be set based on a known or determined population value and can be supplied in the format of a graph or table that permits easy comparison of measured, experimentally determined values.

cDNA (complementary DNA): A piece of DNA lacking internal, non-coding segments (introns) and regulatory sequences that determine transcription. cDNA is synthesized in the laboratory by reverse transcription from messenger RNA extracted from cells.

CRD: A cysteine rich domain that typically is about 120 amino acids in length and found on the amino terminal half of Fz proteins. In the prototypical sFRP described herein, the CRD comprises sFRP-1 residues 38-166. Met (ATG) was added at the N-terminus to facilitate protein expression. Typically the Met is cleaved in the bacteria as the protein is processed. The CRD sequence is shown below:

MFQSDIGPYQ SGRFYTKPPQ CVDIPADLRL CHNVGYKKMV
LPNLLEHETM AEVKQQASSW.VPLLNKNCHA GTQVFLCSLF
APVCLDRPIY PCRWLCEAVRDSCEPVMQFF
GFYWPEMLKC.DKFPEGDVCI (amino acids 38-166 of SEQ ID NO:3)

Detectable marker or label: A "detectable marker" or "label" is any molecule or composition that is detectable by, for instance, spectroscopic, photochemical, biochemical, immunochemical, electrical, optical, or chemical means. Examples of labels, including radioactive isotopes, enzyme substrates, co-factors, ligands, chemiluminescent or fluorescent agents, haptens, enzymes, colloidal gold particles, colored latex particles, and epitope tags, have been disclosed previously and are known to those of ordinary skill (see, for instance, U.S. Pat. Nos. 4,275,149; 4,313,734; 4,373,932; and 4,954,452).

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("western"), and affinity chromatography. Examples of useful epitope tags include FLAG, T7, HA (hemagglutinin) and myc.

Fluorophore: A chemical compound, which when excited by exposure to a particular wavelength of light, emits light (i.e. fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366, and include for instance: 4-acetamido4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylamninophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include GFP (green fluorescent protein), Lissamine™, diethylaminocoumarin, fluorescein chlorotriazinyl, naphthofluorescein, 4,7-dichlororhodamine and xanthene and derivatives thereof Other fluorophores known to those skilled in the art may also be used.

Fusion protein: A protein comprising two amino acid sequences that are not found joined together in nature. The term "sFRP peptide motif fusion protein" refers to a protein that comprises a first amino acid sequence that binds sFRP and a second amino acid sequence. The sFRP binding motif and the second amino acid sequence may alternatively be referred to as domains of the fusion protein. Thus, for example, the present disclosure provides fusion proteins comprising first and second domains, wherein the first domain includes a peptide motif that binds sFRP. The link between the first and second domains of the fusion protein is typically, but not necessarily, a peptide linkage.

Isolated: An "isolated" biological component (such as a nucleic acid or protein or organelle) has been substantially separated or purified away from other biological components in the cell of the organism in which the component naturally occurs (i.e. other chromosomal and extra-chromosomal DNA and RNA, proteins and organelles). Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Linker group or linking group: A linking group is a "chemical arm" between a protein or peptide and a detectable marker. As one of skill in the art will recognize, to form a chemical arm linker, each of the reactants must contain the necessary groups to link the peptide to the detectable marker. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkylhalides to form thioethers. Hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to attach the protein or peptide to the detectable marker r label. In some cases the linking group may be designed to be either hydrophilic or hydrophobic in order to enhance the desired binding characteristics of the ligand and the receptor. The covalent linkages should be stable relative to the solution conditions under which the ligand and liking group are subjected. Generally preferred linking groups will be from 1-20 carbons and 0-10 heteroatoms (NH, O, S) and may be branched or straight chain. Without limiting the foregoing, it should be obvious to one skilled in the art that only combinations of atoms that are chemically compatible comprise the linking group. For example, amide, ester, thioether, thiol ester, keto, hydroxyl, carboxyl, ether groups in combinations with carbon-carbon bonds are acceptable examples of chemically compatible linking groups.

Mimetic: A molecule (such as an organic chemical compound) that mimics the activity of a protein, such as sFRP or its fragments, the peptide motif (such as SEQ ID NO: 9 or SEQ ID NO: 40), or variants or fusions thereof Peptidomimetic and organomimetic embodiments are within the scope of this term, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides having substantial specific inhibitory activity or agonist activity. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., *Pharmaceutical Biotechnology*, Interpharm Press: Buffalo Grove, Ill., pp. 165-174, 1993 and *Principles of Pharmacology* (ed. Munson), chapter 102, 1995, for a description of techniques used in computer assisted drug design.

Oligonucleotide: A linear polynucleotide sequence of up to about 100 nucleotide bases in length. In several embodiments an oligonucleotide is at least 10, 20, 30, 40, or 50 nucleotides in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Osteoclast: Osteoclasts are large, multinucleate cells that actively reabsorb bone. Osteoclasts are derived from hematopoietic stem cells and share phenotypic characteristics with circulating monocytes and tissue macrophages. They are formed from a population of the circulating mononuclear cells that are recruited from the blood to the bone surface where they undergo differentiation and fusion to form multinucleated cells.

Osteopetrosis is a family of diseases characterized by the failure of the long bones to be remodeled. The resulting long bones have cartilagenous infiltration towards the center of the bone from the growth plate and a poorly remodeled center. While osteoporosis can be caused by too many osteoclasts, osteopetrosis can be caused by not having sufficient numbers of these cells.

Loss of ovarian function following menopause often results in a progressive loss of trabecular bone mass and eventually to osteoporosis. This bone loss is in part due to the increased production of osteoclasts. This increased production of osteoclasts appears to be due to the increased elaboration by support cells of osteoclastogenic cytokines such as IL-1, tumor necrosis factor, and IL6, all of which are negatively regulated by estrogens.

Osteoclasts are commonly found in degenerative bone diseases at sites of osteolysis. Osteoclast overproduction is associated with diseases such as hyperparathyroidism and Paget's disease. Osteoclasts are also seen at sites of inflammatory reactions associated with aseptic loosening of total hip prosthesis, rheumatoid arthritis, and periodontitis. Two cytokines produced by inflammatory cells that may have direct effects on osteoclast formation and function are interleukin-1 (IL-1) and tumor necrosis factor (TNF-α).

Peptide motif: An amino acid sequence that binds sFRP-1. Generally, a peptide motif is sequence of two or more peptide-linked amino acids that provides a characteristic structure and or function. In one embodiment, a peptide motif can be found in more than one protein or more than once in a single protein. For example, the peptide motif shown in SEQ ID NO: 9 is characterized by its ability to bind to sFRP and modulate sFRP activity. Without being bound by theory, the three core residues of SEQ ID NO: 9 (D-G-R) are believed to be important for sFRP-1 binding. Thus, in one embodiment, a peptide motif includes these three amino acids. In another embodiment a peptide motif includes the five core amino acids of SEQ ID NO: 9 (V-D-G-R-W). In addition to the prototypical peptide motif there are several other examples of motifs (SEQ ID NOS: 9-11, 14-17, and 24-26) that bind to sFRP and can be capable of modulating sFRP activity.

While the amino acid sequence of one embodiment of the peptide motif that binds sFRP-1 is shown in SEQ ID NO: 9, one of skill in the art will appreciate that variations in this amino acid sequence, such as 1, 2, or 3 deletions, additions, or substitutions, can be made without substantially affecting the activities of the peptide motif. Thus, the term "peptide motif" encompasses both the motif provided in SEQ ID NO: 9, and the additional peptide motifs provided in SEQ ID NOS: 10 and 11 and 14-26, as well as amino acid sequences that are based on these sequences but which include one or more sequence variants and fragments of these sequences that contain at least 3, 4, 5, or 6 contiguous amino acids of the peptide motif. Such sequence variants or fragments can also be defined in the degree of amino acid sequence identity that they share with the amino acid sequence shown in SEQ ID NO: 9. Typically, peptide motif sequence variants will share at least 80% sequence identity with the sequences shown in SEQ ID NOS: 9-12 and 14-26. More highly conserved variants will share at least 90%, at least 95%, or at least 98% sequence identity with the sequences shown in SEQ ID NOS: 9-12, 14-17, and 24-26.

The peptide motif is characterized by its ability to bind to sFRP. This activity can be tested using the ELISA assay described below in the methods section. The peptide motifs ability to bind to sFRP and modulate sFRP activity is beneficial in a number of applications, including clinical applications such as in the treatment of diseases associated with abnormal bone remodeling, and more specifically when increased osteoclast activity is desired.

Peptide tag: A peptide sequence that is attached (for instance through genetic engineering) to another peptide or a protein, to provide a function to the resultant fusion. Peptide tags are usually relatively short in comparison to a protein to which they are fused; by way of example, peptide tags are four or more amino acids in length, such as 5, 6, 7, 8, 9, 10, 15, 20, or 25 or more amino acids. Usually a peptide tag will be no more than about 100 amino acids in length, and may be no more than about 75, no more than about 50, no more than about 40, or no more than about 30.

Peptide tags confer one or more different functions to a fusion protein (thereby "functionalizing" that protein), and such functions can include antibody binding (an epitope tag), purification, and differentiation (e.g., from a native protein). In addition, a recognition site for a protease, for which a binding antibody is known, can be used as a specifically cleavable epitope tag. The use of such a cleavable tag can provide selective cleavage and activation of a protein (e.g., by replacing the cleavage site in TGF-β1 with that for procaspase 3.

Detection of the tagged molecule can be achieved using a number of different techniques. These include: immunohistochemistry, immunoprecipitation, flow cytometry, immunofluorescence microscopy, ELISA, immunoblotting ("western"), and affinity chromatography.

Epitope tags add a known epitope (antibody binding site) on the subject protein, providing binding of a known and often high-affinity antibody, and thereby allowing one to specifically identify and track the tagged protein that has been added to a living organism or to cultured cells. Examples of epitope tags include the myc, T7, GST, GFP, HA (hemagglutinin) and FLAG tags. The first four examples are epitopes derived from existing molecules. In contrast, FLAG is a synthetic epitope tag designed for high antigenicity (see, e.g., U.S. Pat. Nos. 4,703,004 and 4,851,341).

Purification tags are used to permit easy purification of the tagged protein, such as by affinity chromatography. A well-known purification tag is the hexa-histidine (6× His) tag, literally a sequence of six histidine residues. The 6× His protein purification system is available commercially from QIAGEN (Valencia, Calif.), under the name of QIAexpress®.

A single tag peptide can serve more than one purpose; any attached tag, for instance, will increase the molecular weight of the fusion protein and thereby permit differentiation between the tagged and native proteins. Antibodies specific for an "epitope tag" can be used to construct an immunoaffinity column, thus permitting an epitope tag to be used for purification of the tagged protein. Likewise, in some instances monoclonal antibodies specific for a purification tag are available (e.g. anti-6× His peptide monoclonal antibodies, which are available through QIAGEN or CLONTECH, Palo Alto, Calif.).

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: A nucleic acid sequence including at least two nucleic acid residues.

Polypeptide: A protein fragment including at least two amino acid residues.

Protein Fragment: An amino acid sequence that contains fewer amino acid residues than are found in a naturally occurring protein and including at least two amino acid residues. For example, if a naturally occurring protein, i.e. a protein expressed from a gene, is 300 amino acid residues long, a polypeptide derived from the protein could have 299 amino acid residues or less. In particular examples, the polypeptide could have less than 200, 175, 150, 125, 100, 75, 50, or 25 amino acid residues.

Purified: The term purified does not require absolute purity; rather, it is intended as a relative term, Thus, for example, a purified protein or peptide preparation is one in which the protein or peptide is more pure than the protein or peptide in its natural environment within a cell. Such proteins or peptides may be produced, for example, by standard purification techniques, or by recombinant expression. In some embodiments, a preparation of a protein or peptide is purified such that the protein or peptide represents at least 50%, for example, or at least 70%, of the total protein content of the preparation.

RANK and RANKL: The receptor activator of NF-κB (RANK) is a member of the tumor necrosis factor (TNF) receptor superfamily. The ligand, receptor activator of NF-KB ligand (RANKL), is a member of the TNF superfamily, and has been characterized in multiple settings and variously termed Osteoclast Differentiation Factor (ODF), Tumor Necrosis Factor-Related Activation-Induced Cytokine (TRANCE) and Osteoprotegerin Ligand (OPGL). RANK is a Type I transmembrane protein having 616 amino acid residues that interacts with TNF-receptor associated factor 3 (TRAF3). Triggering of RANK by over-expression, co-expression of RANK and membrane bound RANK ligand (RANKL), or the addition of soluble RANKL or agonistic antibodies to RANK, results in the upregulation of the transcription factor NF-κβ, a ubiquitous transcription factor that is most extensively utilized in cells of the immune system (U.S. Pat. No. 6,017,729).

RANK is expressed on osteoclast precursors and mature osteoclasts. RANKL produced by osteoblasts stimulates the formation and activity of osteoclasts, which facilitates normal bone development and remodeling. Gene targeting of either RANKL or RANK results in osteopetrosis (increased bone mass), as well as severe defects in lymph node formation. Osteoprotegerin (OPG) is a soluble factor that also belongs to the TNF receptor family. OPG binds to RANKL, and inhibits the formation of functional multinucleate osteoclasts in vitro. Overexpression of OPG in transgenic mice causes severe osteopetrosis, with a loss of marrow cavities and profound depletion of osteoclasts. The same effects were observed upon administration of OPG in normal mice. These effects were all attributable to OPG's binding to RANKL, which prevented ligand binding and activation of RANK. Alternatively, expression of RANKL by T cells in the joints of subjects afflicted with rheumatoid arthritis is thought to contribute to the heightened osteoclast activity and bone loss characteristic of this disorder.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of sFRP (the prototypical member of which is shown in SEQ ID NO: 1), or the peptide motif that binds sFRP (for example SEQ ID NO:9), disclosed herein, will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of sFRP, sFRP fragments, or the peptide motif that binds sFRP, are typically characterized by possession of at least 50% sequence identity counted over the full length alignment with the amino acid sequence of sFRP, sFRP fragments or the peptide motif (for example SEQ ID NO: 9) using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 60%, at least 65%, at least 70%, at least 75%, at least 80%, at least 90%, or at least 95%, or 98% sequence identity. When less than the entire sequence is being compared for sequence identity, homologs and variants will typically possess at least 75% sequence identity over short windows of 10-20 amino acids, and can possess sequence identities of at least 85% or at least 90%, 95%, or 98% depending on their similarity to the reference sequence. Methods for determining sequence identity over such short windows are described at the website that is maintained by the National Center for Biotechnology Information in Bethesda, Md. One of skill in the art will appreciate that these sequence identity ranges are provided for guidance only; it is entirely possible that strongly significant homologs could be obtained that fall outside of the ranges provided.

sFRP: Secreted Fizzled-related protein (sFRP) is a secreted protein that consists of approximately 300 amino acids, including a CRD that is typically between 30% and 50% identical to the (cysteine-rich domain) CRD of the Fz protein family members. There are several different sFRP proteins and the nucleic acid sequence of the prototypical member, sFRP-1, is provided in SEQ ID NO: 1. The nucleic acid and amino acid sequences of other members of the sFRP family can be found at the National Center for Biotechnology Website, for example GenBank Accession No. AF218056 (Gallus gallus FRP-2), GenBank Accession No AV354083 (Mus musculus-FRP-1), GenBank Accession No AV304328 (Mus musculus s-FRP-2), GenBank Accession No U24163 (homo sapiens sFRP-3/FrzB) and GenBank Accession No AI587049 (Homo sapiens sFRP-1). The open reading frame of the prototypical sFRP is shown in SEQ ID NO: 2, while the sequence of the protein is shown in SEQ ID NO: 3. As disclosed herein, sFRP binds to RANKL and inhibits osteoclast formation.

sFRP-1 binding activity and its ability to modulate osteoclast formation can be assayed using the ELISA and osteoclastogenesis bioassay methods described herein. The ability of sFRP-1 protein, or a fragment thereof, to perform these activities is beneficial in a number of applications, including clinical applications such as in the treatment of diseases associated with abnormal bone remodeling.

While the amino acid sequence of the prototypical sFRP is shown in SEQ ID NO: 3, one of skill in the art will appreciate that variations in this amino acid sequence, such as 1, 2, 5, 10, 20, 30, 40, or 50, deletions, additions, or substitutions (including conservative amino acid substitutions), can be made without substantially affecting the activities of the protein (or fragments of the protein) discussed above. Thus, the, term "sFRP" fragments encompasses both the proteins having the amino acid sequences shown in SEQ ID NOs: 4-8, as well as amino acid sequences that are based on these sequences but which include one or more sequence variants. Such sequence variants can also be defined in the degree of amino acid sequence identity that they share with the amino acid sequence shown in SEQ ID NOs: 4-8. Typically, sFRP sequence variants will share at least 80% sequence identity with the sequences shown in SEQ ID NOs: 4-8. More highly conserved variants will share at least 90%, at least 95%, or at least 98% sequence identity with the sequences shown in SEQ ID NOs: 4-8. In addition to sharing sequence identity with the prototypical sFRP protein sequence, such sequence variants possess the ability to bind to TNF family members such as RANKL.

Subject: Living multi-cellular vertebrate organisms, a category that includes both human and non-human mammals.

Therapeutically effective dose: A dose sufficient to prevent advancement, or to cause regression of the disease, or which is capable of relieving symptoms caused by the disease.

TNF family of proteins: The Tumor Necrosis (TNF) family of proteins contains both membrane bound ligands and soluble proteins. Some family members, such as TNF and RANKL, are active in both membrane-anchored and soluble forms, the latter being enzymatically released into solution, notably by TACE (TNF alpha converting enzyme) (J. Hardy, *Proc. Natl. Acad. Sci. U.S.A.* 94:2095-2097, 1997; J. D. Buxbaum et al., *Proc. Natl. Acad Sci. U.S.A.* 89: 10075-10078, 1992). The primary area of homology among TNF family members is a stretch of 150 amino acid residues in the carboxy-terminus that is situated in the extracellular space. This domain is responsible for binding to cognate members of the TNF receptor family. This family of receptor proteins is characterized by four domains with regularly spaced cysteine residues: each has a single transmembrane domain and binds either TNFα or TNFβ. Members of the family include, for example, TNFRI, TNFRII, Fas, CD30, and CD30.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector can include nucleic acid sequences that permit it to replicate in a host cell, such as an origin of replication. A vector can also include one or more selectable marker genes and other genetic elements known in the art. A vector can also include a sequence encoding an amino acid motif that facilitates the isolation of the desired protein product such as a sequence encoding maltose binding protein, c-myc, or GST.

WNT: One group of genes and the proteins encoded by them that play an important role in regulating cellular development is the Wnt family of glycoproteins. Wnt proteins are a family of growth factors consisting of more than a dozen structurally related molecules and are involved in the regulation of fundamental biological processes, like apoptosis, embryogenesis, organogenesis, morphogenesis and tumorigenesis. These polypeptides are multipotent factors and have similar biological activities to other secretory proteins like transforming growth factor (TGF)-β, fibroblast growth factors (FGFs), nerve growth factor (NGF), and bone morphogenetic proteins (BMPs).

A member of the Wnt growth factor family is preferentially expressed in bone tissue and in bone-derived cells, and appears to be involved in maintaining the mature osteoblast (bone-forming cell) phenotype.

Unless otherwise explained, all technical and scientific terms used herein have the same meaning as commonly understood by one of ordinary skill in the art to which this disclosure belongs. "Comprising" means "including." The singular terms "a", "an", and "the" include plural referents unless context clearly indicates otherwise. Hence, "comprising A and B" means "including A and B" without excluding other elements. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

As disclosed herein, a peptide motif has been demonstrated to bind to sFRP-1 (SEQ ID NO: 3) and inhibit the ability of sFRP-1 to down regulate the formation of osteoclasts. In one embodiment, the peptide motif has the formula:

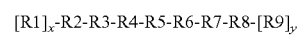

$[R1]_x$-R2-R3-R4-R5-R6-R7-R8-$[R9]_y$ wherein x and y are integers independently selected from the group 0 or 1; R1, R2, R8, and R9 are any amino acid residue; R3 is selected from the group Val (V), Ala (A) or conservative substitutions therefore; R4 is selected from the group consisting of Asp (D), Ala (A) or conservative substitutions therefore; R5 is selected from the group consisting of Gly (G), Ala (A) or conservative substitutions therefore; R6 is selected from the group consisting of Arg (R) Ala (A) or conservative substitutions therefore; R7 is selected from the group consisting of Trp (W), Ala (A) or conservative substitutions therefore; and wherein the peptide retains the ability to bind to a sFRP.

In one embodiment, R1 is selected from the group consisting of (a) Gln-Gly-Thr (QGT), (b) Ala-Gly-Thr (AGT), (c) Gln-Ala-Thr (QAT), and (d) Gln-Gly-Ala (QGA). In another embodiment, R2 is selected from the group Leu, Val, Ala (L, V, A) or a conservative substitution therefor. In a further embodiment, R8 is selected from the group consisting of Leu or Val (L or V) or a conservative substitution therefor. In yet another embodiment, R9 is selected from the group consisting of (a) Gln (Q), (b) Gln-Gly-Glu (QGE), (c) Gln-Leu (QL), (d) Ala-Leu (AL), (e) Gln-Ala (QA) and (f) Thr-Asn-Pro-His-His (TNPHH).

In a specific, non-limiting example, R3 is V, R4 is D, R5 is R, R6 is G, and R7 is W. In another specific, non-limiting example, R1 is selected from the group consisting of (a) Gln-Gly-Thr (QGT), (b) Ala-Gly-Thr (AGT), (c) Gln-Ala-Thr (QAT), and (d) Gln-Gly-Ala (QGA); R2 is selected from the group Leu, Val, Ala (L, V, A) or a conservative substitution therefor; R8 is selected from the group consisting of Leu or Val (L or V) or a conservative substitution therefor; R9 is selected from the group consisting of (a)Gln (Q), (b) Gln-Gly-Glu (QGE), (c)Gln-Leu (QL), (d) Ala-Leu (AL), (e) Gln-Ala (QA) and (f) Thr-Asn-Pro- His-His (TNPHH); and R3 is V, R4 is D, R5 is R, R6 is G, and R7 is W. In yet another non-limiting example R3 is V, R4 is D, R5 is R, R6 is G, and R7 is W and R1 is selected from the group consisting of (a) Gln-Gly-Thr (QGT), (b) Ala-Gly-Thr (AGT), (c) Gln-Ala-Thr (QAT), and (d) Gln-Gly-Ala (QGA). In a further non-limiting example R3 is V, R4 is D, R5 is R, R6 is G, and R7 is W R2 is selected from the group Leu, Val, Ala (L, V, A) or conservative substitutions therefor. In another specific, non-limiting example, R3 is V, R4 is D, R5 is R, R6 is G, and R7 is W and R8 is selected from the group consisting of Leu, Val, Ala (L, V, A) and conservative substitutions therefor. In another specific, non-limiting example, R3 is V, R4 is D, R5 is R, R6 is G, and R7 is W and R9 is selected from the group consisting of (a)Gln (Q), (b)Gln-Gly-Glu (QGE), (c)Gln-Leu (QL), (d) Ala-Leu (AL), (e) Gln-Ala (QA) and (f) Thr-Asn-Pro- His-His (TNPHH). One specific, non-limiting example of a peptide motif is SEQ ID NO: 9.

In one embodiment, the sFRP binding peptide is less than 30 amino acids in length. In another embodiment, the peptide is less than 20 amino acids in length. In a further embodiment, the peptide is less than 10 amino acids in length.

The identification of a peptide motif that binds sFRP (for example, SEQ ID NO: 9) has also allowed other proteins to be identified, which are characterized by the presence of a sequence resembling the peptide motif in their amino acid sequences, and by their ability to bind to sFRP family members. These peptides interfere with sFRP activity, for example binding RANKL or a TNF family member, or osteoclastogenesis stimulating activity. Accordingly, the disclosure provides methods of controlling bone remodeling. The peptide motif disclosed herein (for example, SEQ ID NO:9) can be used to bind to sFRP-1 and effectively upregulate osteoclast differentiation. Increased osteoclast production is desirable for the treatment of disorders where there is too much bone formation (for example, achondroplasia, Albright's osteodystrophy, and osteopetrosis). Conversely, the disclosure also provides methods of providing sFRP to increase bone mass (see FIG. 17). An increase in bone mass is desirable for the treatment of disorders such as postmenopausal osteoporosis, Paget's disease, lytic bone metastases, multiple myeloma, hyperparathyroidism, rheumatoid arthritis, periodontitis, and hypercalcemia of malignancy.

Some embodiments of the disclosure provide isolated polypeptides, including the amino acid sequence shown in SEQ ID NO: 9; conservative amino acid substitutions of the amino acid sequence shown in SEQ ID NO: 9; and amino acid sequences that share at least 80% sequence identity with the sequence shown in SEQ ID NO: 9. These polypeptides are capable of binding sFRP-1 (SEQ ID NO: 3) and interfering with sFRP activity, for example osteoclastogenesis activity. Examples of such polypeptides are provided in SEQ ID NOS: 10-12 and 14-29.

The disclosure also provides nucleic acid sequences that encode the peptide motif that binds sFRP and the variants of the peptide motif that binds sFRP that are described in the paragraph above. These nucleic acid sequences can be placed in vectors, and the vectors can be used to transform host cells. The transformed host cells are subsequently useful for, among other things, producing the above-described polypeptides.

As mentioned above, the disclosure provides methods of enhancing osteoclast differentiation in a subject. These methods include providing an effective amount of a peptide that includes the motif (such as SEQ ID NO: 9), or variants, or fragments thereof to increase osteoclast differentiation Such methods are useful for treating subjects suspected of having abnormal bone remodeling (e.g. achondroplasia, Albright's osteodystrophy, or osteopetrosis).

The disclosure also provides methods of inhibiting osteoclast formation in a subject These methods include administering sFRP-1 (SEQ ID NO: 3), variants of sFRP-1 (SEQ ID NO: 3), or fusions, or fragments of sFRP-1 (SEQ ID NO: 3). Administering these peptides includes administration and expression of nucleic acids that encode the peptides. The administered proteins or peptides are characterized by their ability to bind t RANKL, for example, human RANKL termed "TRANCE" (AF013171), human RANKL (AF019047), and human RANKL termed "OPGL" (AF053712) and inhibit osteoclast formation. The inhibition of osteoclast formation will be useful for treating osteopathic disorders such as postmenopausal osteoporosis, Paget's disease, lytic bone metastases, multiple myeloma, hyperparathyroidism, rheumatoid arthritis, periodontitis, and hypercalcemia of malignancy.

The peptide motif that binds sFRP, and fragments and variants thereof, are also useful for modulating T-cell activity. Accordingly, the disclosure provides methods of modulating T-cell activity. These methods include providing an effective amount of the peptide motif that binds sFRP (such as SEQ ID NO:9), or fragments and variants thereof, sufficient to change T-cell interaction with dendritic cells or osteoclast progenitor cells. Examples of changes in the interaction between the T-cell and the dendritic cell include an increase in dendritic cell survival, and T cell proliferation, in a mixed lymphocyte reaction, as described for RANKL/RANK signaling (D. M. Anderson et al., *Nature* 390:175-179, 1997; and B. R. Wong et al., *J. Exp. Med.* 186:2075-2080, 1997). Modulating T-cell activity is desirable in subjects suspected of having, for example, toxic shock, sepsis, graft-versus-host reactions, or acute inflammatory reactions.

The disclosure also provides methods of screening for sFRP proteins, and fragments, and variants thereof, that bind to members of the TNF family of proteins. These methods include contacting an sFRP protein with at least one TNF family member, and detecting TNF family member binding to the sFRP protein. Members of the TNF family that are of particular interest include RANKL, Apo2/TRAIL, FasL, CD40L, CD27L, CD30L, Apo3L/TWEAK, TNF and LT-alpha (S. J. Baker and E. P. Reddy, *Oncogene* 17: 3261-3270, 1998). Members of the sFRP family that are of particular interest include sFRP-1 (SEQ ID NO: 3), sFRP-2 (GenBank Accession No. MMU88567, incorporated herein by reference), sFRP-3 (GenBank Accession No. MMU88568, incorporated herein by reference), sFRP-4 (GenBank Accession No. AF012891, incorporated herein by reference), and sFRP-5 (GenBank Accession No. AF117758, incorporated herein by reference).

The disclosure also provides the purified peptide shown in SEQ ID NO: 14. This peptide is useful for stimulating osteoclast differentiation in vitro and in vivo. When the peptide is used in vivo it can be administered to subjects to increase osteoclast differentiation.

IV. Expression and Purification of sFRP, Fragments, Fusions, and Variants Thereof, as Well as the Peptide Motif sFRP fragments and variants thereof can be purified from MDCK cells (ATCC NO. CCL-34) transfected with sFRP encoding vectors as described below. sFRP fragments and variants thereof can also be purified from a tissue source using conventional biochemical techniques, or produced recombinantly in either prokaryotic or eukaryotic cells using methods well-known in the art (for example, those described in Sambrook et al, *Molecular Cloning. A Laboratory Manual*, Cold Spring Harbor, N.Y., 1989). The recombinant expression of sFRP fragments is described in (Uren et al., *J. Biol. Chem.* 275:4374-4382, 2000). Furthermore, the nucleic acid sequences encoding sFRP family members are available on GenBank, and include the cDNA sequence shown in SEQ ID NO: 1.

Recombinant sFRP fragments, fusions, and variants thereof, as well as the binding motif (SEQ ID NO: 9) and variants thereof, can be obtained using commercial systems designed for optimal expression and purification of fusion proteins. Such fusion proteins typically include a protein tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). For example, the pMAL expression system utilizes a vector that adds a maltose binding protein to the expressed protein. The fusion protein is expressed in *E. coli.*, and the fusion protein is purified from a crude cell extract using an amylose column. If necessary, the maltose binding protein domain can be cleaved from the fusion protein by treatment with a suitable protease, such as Factor Xa. The maltose-binding fragment can then be removed from the preparation by passage over a second amylose column. Eukaryotic expression systems can also be employed, including Pichia, tobacco and Baculovirus expression systems, such as those available commercially from Invitrogen.

For each of these systems, the entire sFRP protein, variants and fragments thereof or the peptide binding motif can be produced by ligating the open reading frame (ORF) of the desired sequence into the vector. To ensure effective expression, the ORF must be operably linked to the vector, i.e. must be joined such that the reading frame of the ORF is aligned with the reading frame of the protein tag. Where fragments of sFRP are to be expressed, an ORF encoding the desired fragment can be amplified by polymerase chain reaction (PCR) from the sFRP cDNA, cloned, purified and then ligated into the expression vector. Alternatively, the amplified fragment can be ligated directly into the expression vector. It can also be possible, depending on the availability of suitable restriction sites in the sFRP cDNA, to obtain the desired fragment by appropriate restriction endonuclease digestion, such that it can be directly cloned into the expression vector.

Purification of the expressed protein can be achieved either using the purification regimen appropriate for the expression tag (if a commercial expression/purification system is used), or conventional affinity chromatography using antibodies, preferably monoclonal antibodies, that recognize the appropriate regions of sFRP can be employed or chromatography procedures established for sFRPs.

Where sFRP fragments or protein fragments containing the peptide motif (for example, SEQ ID NO: 9) are to be used, such fragments alternatively can be generated through digestion of a full-length protein with various proteases. The fragments can then be separated based on their unique size, charge or other characteristics. Such fragments can also be synthetically generated through the use of known peptide synthesis methods.

V. Methods of Enhancing or Inhibiting Osteoclast Formation

The peptide motif that binds sFRP can be used to enhance osteoclast differentiation. Osteoclasts are large, multinucleate cells that actively reabsorb bone, are derived from hematopoietic stem cells, and share phenotypic characteristics with circulating monocytes and tissue macrophages. They are formed from a population of the circulating mononuclear cells that are recruited from the blood to the bone surface, where they undergo differentiation and fusion to form multinucleated cells.

Osteopetrosis is a family of diseases characterized by the failure of the long bones to be remodeled. The resulting long bones have cartilagenous infiltration towards the center of the bone from the growth plate and a poorly remodeled center. While osteoporosis can be caused by osteoclasts that are too numerous or too active, osteopetrosis can be caused by not having sufficient numbers of these cells, or by their inadequate activity. Thus, enhancement of osteoclast differentiation is desirable in subjects with abnormal bone remodeling, such as achondroplasia and osteopetrosis. Methods of administration of these FRP-1 to inhibit osteoclast differentiation in a subject are described below.

Conversely, sFRP-1 can be used to inhibit osteoclast formation. Loss of ovarian function following menopause often results in a progressive loss of trabecular bone mass and eventually to osteoporosis. This bone loss is in part due to the increased production of osteoclasts. This increased production of osteoclasts appears to be due to the increased elaboration by support cells of osteoclastogenic cytokines such as IL-1, tumor necrosis factor, and IL-6, all of which are negatively regulated by estrogens.

Osteoclasts are also implicated in degenerative bone diseases at sites of osteolysis. Likewise, osteoclast overproduction is associated with diseases such as hyperparathyroidism and Paget's disease. Osteoclasts are also seen at sites of inflammatory reactions associated with aseptic loosening of total hip prosthesis, rheumatoid arthritis, and periodontitis. Two cytokines produced by inflammatory cells that may have direct effects on osteoclast formation and function are interleukin-1 (IL-1) and tumor necrosis factor (TNF-$\alpha$). Thus, inhibition of osteoclast formation is desirable in subjects with bone disorders characterized by unwanted bone resorption.

In view of sFRP-1's ability to inhibit osteoclastogenesis, sFRP-1 can have clinical utility in conditions where excessive osteoclast activity has pathological consequences. Osteoporosis and rheumatoid arthritis are examples of conditions that are particularly good targets for sFRP-1 therapy because soluble RANKL from T cells is thought to have an important role in the bone loss associated with these diseases. Methods of administration of sFRP-1 to inhibit osteoclast formation in a subject are disclosed herein.

Disorders of calcium homeostasis can also be affected by osteoclast activity. For example, osteoclasts are able to mobilize calcium from bone to affect hypocalcemic states. Alternatively, inhibition of osteoclasts can help minimize mobilization of in hypercalcemic states. Hence, modulation of osteoclast activity can be used as a therapeutic intervention to treat hypocalcemia and hypercalcemia.

VI. Methods of Modulating T-cell Activity in a Subject

The sFRP-binding peptides described herein are effective for treatment of conditions or diseases that involve the immune system, for instance conditions (including clinical treatments) that inhibit (or suppress) the immune system. General information about the therapeutic use of immunomodulatory compounds is well known, and can be found for instance in U.S. Pat. Nos. 5,632,983; 5,726,156; and 5,861,483.

The peptide motif disclosed herein is of use in modulating antigen presentation. T-cells produce RANKL, and dendritic cells express RANK. Thus, in order to increase an immune response, T cells can be exposed to a polypeptide including the peptide motif, for example administration of the polypeptide to a subject. The administration of the polypeptide results in an increase in RANKL, and subsequently the binding of RANK to RANKL on T cells. Thus, in the presence of an antigen, administration of a polypeptide including the sFRP binding peptide disclosed herein results in increased antigen presentation, and a corresponding upregulation of an immune response against the antigen. Immune deficiencies (e.g., deficiencies of one or more type of immune cells, or of one or more immunological factors) associated with immune deficiency diseases, immune suppressive medical treatment, acute and/or chronic infection, and aging can be treated using the methods and compositions described herein. A general overview of immunosuppressive conditions and diseases can be found in Harrisons "Principles of Internal Medicine," 14$^{th}$ Edition, McGraw-Hill, 1998, and particularly in chapter 86 (Principles of Cancer Therapy), chapter 88 (Melanoma and other Skin Cancers), chapter 307 (Primary Immune Deficiency Diseases), and chapter 308 (Human Immunodeficiency Virus Diseases). In one embodiment a polypeptide including the sFRP binding peptide motif is administered to an immunosuppressed subject, such as a subject receiving immunosuppressive medical treatment, a subject with an age-linked immunodeficiency, or a subject that is infected with a human immunodeficiency virus. In another embodiment, the peptides disclosed herein are utilized to activate the immune system against various diseases, both chronic and acute. Subject infections include bacterial and viral infections, as well as infestations caused by eukaryotic pathogens and parasites.

More particularly, immunostimulatory sFRP-1-binding peptide-treatment can be used in the treatment of HIV disease.

VII. Methods of Regulating Intraocular Pressure and Treating Glaucoma

In addition to the peptide motif s impact on sFRP-1/RANKL binding, compositions containing the peptide motif (such as a composition including a peptide as set forth as SEQ ID NO: 9) also have utility in disrupting the interaction of sFRP-1 with other proteins. For instance, sFRP-1 binding to the ANP receptor A can regulate the release of sodium and fluid in the kidney and eye. It has been demonstrated that the relevant components of natriuretic peptide system are functionally expressed in the human eye where they are believed to serve as modulators of intraocular pressure (J. Ortego and M. Coca-Prados, *Biochem. Biophys. Res. Commun.* 258: 21-28, 1999). In the eye, sFRP-1 or its binding peptide can have an important impact on the release of fluid into the eye with resultant changes in the intraocular pressure. In one embodiment, a polypeptide that includes a peptide motif that binds sFRP, such as a polypeptide including SEQ ID NO:9, is administered to a subject to decrease intraocular pressure. In one specific non-limiting example, the polypeptide including the peptide motif that binds sFRP is administered to decrease intraocular pressure in a subject with glaucoma (see Johnson and R. C. Tschumper, Invest. *Ophthalmol. Vis. Sci.* 28: 945-953, 1987). The peptide can be administered intraocularly (for example in a sustained release intraocular implant). Alternatively, the polypeptide may be administered systemically, in a therapeutically effective amount sufficient to inhibit production of aqueous humor in the anterior chamber of the eye.

VIII. Screening Assays for Detecting sFRP Modulation of TNF-ligand Family Members The peptide motif that binds sFRP can be used in screening for the identification of proteins and other compounds that bind to, or otherwise directly interact with sFRP or fragments thereof, such as a mimetic. The proteins include members of the TNF family of proteins such as, RANKL, TRAIL, FasL, CD40L, CD27L, CD30L, and NGF. In one embodiment, a cell lysate or tissue homogenate can be screened for proteins or other compounds that disrupt sFRP/TNF or sFRP/peptide motif binding. Alternatively, any of a variety of exogenous compounds, both naturally occurring and/or synthetic (e.g. libraries of small molecules or peptides), can be screened for the ability to disrupt sFRP/TNF or sFRP/peptide motif binding (such as the ability to disrupt binding of a peptide having a sequence as set forth as SEQ ID NO: 9 with TNF or RANKL). Small molecules are particularly preferred in this context because they are more readily absorbed after oral administration, have fewer potential antigenic determinants, and/or are more likely to cross the blood brain barrier than larger molecules such as nucleic acids or proteins.

Furthermore, the identification of deletion mutants (i.e. the fragments of sFRP shown in the sequence listing) that are significantly smaller than full length sFRP but yet maintain the ability to bind to and regulate TNF proteins provides "lead compounds" for the design and development of new pharmaceuticals. Similarly, a polypeptide including a peptide motif that binds sFRP can serve as a "lead compound." For example, as is well known in the art, sequential modification of small molecules (e.g. amino acid residue replacement with peptides; functional group replacement with peptide or non-peptide compounds) is a standard approach in the pharmaceutical industry for the development of new pharmaceuticals. Such development generally proceeds from a "lead compound" which is shown to have at least some of the activity (e.g. modulates osteoclastogenesis) of the desired pharmaceutical. In particular, when one or more compounds having at least some activity of interest are identified, structural comparison of the molecules can greatly inform the skilled practitioner by suggesting portions of the lead compounds that should be conserved, and portions that can be varied in the design of new candidate compounds. Thus, the present disclosure also provides potential lead compounds as well as means of identifying such lead compounds that can be modified sequentially to produce new candidate compounds for use in the treatment of diseases associated with abnormal osteoclast activity, i.e. arthritis. These new compounds then can be tested both for TNF receptor binding (in the case of lead compounds developed from sFRP) or sFRP binding (in the case of lead compounds developed from the peptide motifs disclosed herein) and for biological efficacy (e.g. in the osteoclastogenesis assays described herein). This procedure can be iterated until compounds having the desired therapeutic activity and/or efficacy ar identified.

The effect of agents that disrupt sFRP/peptide motif binding can be monitored using the osteoclast differentiation assays described below. Agents that disrupt sFRP binding and enhance osteoclastogenesis are useful for treating conditions associated with increased bone mass and agents that are found to enhance sFRP/TNF binding are useful for treating diseases associated with decreased bone mass (e.g. see FIG. 17). Methods of detecting such binding include the ELISA assays described below, as well as other methods that involve monitoring changes in fluorescence, molecular weight, or the concentration of either sFRP, or proteins containing the peptide motif that binds sFRP either in a soluble phase or in a substrate-bound phase. In one embodiment, the peptide motif has a sequence as set forth as SEQ ID NO:9.

Once identified by the methods described above, the candidate compounds can then be produced in quantities sufficient for pharmaceutical administration or testing (e.g. µg or mg or greater quantities), and formulated in a pharmaceutically acceptable carrier (see, e.g. Remington's Pharmaceutical Sciences, Gennaro, A., ed., Mack Pub., 1990). These candidate compounds can then be administered to the transformed cells of the disclosure, to the transgenic animal models of the disclosure, to cell lines derived from the animal models or from human patients.

The proteins or other compounds identified by these methods can be purified and characterized by any of the standard methods known in the art. Proteins can, for example, be purified and separated using electrophoretic (e.g. SDS-PAGE, 2D PAGE) or chromatographic (e.g. HPLC) techniques and can then be microsequenced. For proteins with a blocked N-terminus, cleavage (e g. by CNBr and/or trypsin) of the particular binding protein is used to release peptide fragments. Further purification/characterization by HPLC and microsequencing and/or mass spectrometry by conventional methods provides internal sequence data on such blocked proteins. For non-protein compounds, standard organic chemical analysis techniques (e.g. IR, NMR and mass spectrometry; functional group analysis; X-ray crystallography) can be employed to determine their structure and identity.

Methods for screening cellular lysates, tissue homogenates, or small molecule libraries for candidate sFRP disrupting molecules are well known in the art and, in light of the present disclosure, can now be employed to identify compounds which disrupt sFRP binding to the peptide motif (for example SEQ ID NO:9) or TNF family members such as RANKL or TRAIL.

In light of the present disclosure, a variety of affinity binding techniques well known in the art can be employed to isolate proteins (i.e. lead compounds) or other compounds. In general, sFRP, a fragment thereof or the peptide motif (for example a fragment of about three or about five amino acids of SEQ ID NO: 9) can be immobilized on a substrate (e.g. a column or filter) and a solution containing a TNF receptor or a sFRP family member protein can be introduced to the column to allow formation of the sFRP/TNF or peptide motif/sFRP complex. Then a solution including the test compound(s) is introduced to the column under conditions that are permissive for binding. The substrate is then washed with a solution to remove unbound or weakly bound molecules. A second wash can then elute those compounds that strongly bound to the immobilized sFRP or peptide motif. Alternatively, the test compounds can be immobilized and a solution containing sFRP/RANKL or sFRP/peptide motif (for example SEQ ID NO: 9) can be contacted with the column, filter or other substrate. The ability of either the sFRP or fragment thereof, or the peptide motif to bind to the test compound can be determined as above.

IX. Incorporation of sFRP Therapeutically Effective Fragments, Fusions, and Variants of sFRP or the Peptide Motif Into Pharmaceutical Compositions and Methods of Treatment For administration to animals, purified sFRP, sFRP fragments, sFRP variants, or peptide motifs that bind sFRP are generally combined with a pharmaceutically acceptable carrier. Pharmaceutical preparations can contain only a single peptide, or can be composed of more than one variety of sFRP fragments and/or peptide motifs. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, human albumin or the like as a vehicle. For solid compositions (e.g. powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As is known in the art, protein-based pharmaceuticals can be only inefficiently delivered through ingestion. However, pill-based forms of pharmaceutical proteins can alternatively be administered subcutaneously, particularly if formulated in a slow-release composition. Slow-release formulations can be produced by combining the target protein with a biocompatible matrix, such as cholesterol. Another possible method of administering protein pharmaceuticals is through the use of mini osmotic pumps. As stated above a biocompatible carrier would also be used in conjunction with this method of delivery.

It is also contemplated that the peptide motifs disclosed herein as well as sFRP could be delivered to cells in the nucleic acid form and subsequently translated by the host cell. This could be done, for example through the use of viral vectors or liposomes. Liposomes could also be used for the delivery of the protein itself.

The pharmaceutical compositions of the present disclosure can be administered by any means that achieve their intended purpose. Amounts and regimens for the administration of sFRP fragments can be determined readily by those with ordinary skill in the clinical art of treating conditions associated with abnormal bone remodeling. For use in treating these conditions, the described proteins are administered in an amount effective to either increase osteoclastogenesis activity or decrease osteoclastogenesis. Such dosages include amounts which raise target tissue concentrations to levels at which the therapeutic activity has been observed in vitro. The proteins disclosed herein can also be used to modulate T-cell interactions and immune system functions. Doses sufficient to achieve a tissue concentration that causes an increase or a decrease in osteoclastogenesis and/or T-cell activity can be determined by using the amounts described in the examples that follow. The peptides or proteins can be administered to a host in vivo, such as for example, through systemic administration, such as intravenous or intraperitoneal administration. Also, the peptides or proteins can be administered intralesionally: i.e. the peptide or protein is injected directly into the tumor or affected area.

Effective doses of the disclosed peptides for therapeutic application will vary depending on the nature and severity of the condition to be treated, the age and condition of the subject and other clinical factors. Thus, the final determination of the appropriate treatment regimen will be made by the clinician. Typically, the dose range will be from about 0.1 µg/kg body weight to about 100 mg/kg body weight. Other suitable ranges include doses of from about 1 µg/kg to 10 mg/kg body weight The dosing schedule can vary from once a week to daily depending on a number of clinical factors, such as the subject's sensitivity to the protein. Examples of dosing schedules are 3 µg/kg administered twice a week, three times a week or daily; a dose of 7 µg/kg twice a week, three times a week or daily; a dose of 10 µg/kg twice a week, three times a week or daily; or a dose of 30 µg/kg twice a week, three times a week or daily. In the case of a more aggressive disease it can be preferable to administer doses such as those described above by alternate routes including intravenously or intrathecally. Continuous infusion can also be appropriate.

EXAMPLES

Polypeptides that bind to sFRP-1 were identified using an open-ended approach. This approach involved screening a peptide phage display cDNA library for sequences that bound to recombinant sFRP-1 (Uren et al., *J. Biol. Chem.* 275:4374-4382, 2000). Peptides that had been identified by phage display were operably linked to a sequence encoding alkaline phosphatase creating a fusion protein that, upon binding to sFRP-1, could be detected. This methodology resulted in the identification of a predominant peptide motif containing the sequence L/V-D-G-R-W-L/V (SEQ ID NO: 9). Alanine scanning was then used to further characterize the peptide motif (SEQ ID NO: 9 and SEQ ID NOs: 14-26).

The sequence of the peptide motif that binds sFRP was then used to identify proteins that potentially bind to sFRP-1. The RANKL protein was identified as a potential candidate because it contained an amino acid sequence that is similar to that of the peptide motif (SEQ ID NO: 9). ELISA analysis using RANKL and sFRP-1 indicated that sFRP-1 binds to RANKL. RANKL is known to be involved with osteoclast differentiation. Subsequently, sFRP-1 (SEQ ID NO: 3) was shown to inhibit osteoclastogenesis. Moreover, a synthetic peptide containing the peptide motif enhanced osteoclastogenesis. This finding indicates that the disruption of the interaction of sFRP-1 (SEQ ID NO: 3) and RANKL with analogs of the peptide motif (SEQ ID NO: 9) can stimulate osteoclast formation. These materials and methods disclosed herein are exemplary only, and are not meant to be limiting.

Example 1

Materials and Methods

1. Materials

Recombinant human sFRP-1 was prepared as described (Uren et al., *J. Biol. Chem.* 275:4374-4382, 2000). The coding sequence of mouse sFRP-2 was amplified by RT-PCR, using total RNA from embryonic mouse kidney as a source, subcloned into pcDNA3.1 expression vector, transfected into MDCK cells and the recombinant protein purified by heparin-affinity chromatography essentially as described for sFRP-1 in Uren et al., *J. Biol. Chem.* 275:4374-4382, 2000. Rabbit polyclonal antiserum was raised against recombinant human sFRP-1 by injecting ~10 µg of purified protein with complete Freund's adjuvant into the inguinal lymph nodes, and subsequently injecting intramuscularly at 2-3 week intervals similar quantities of antigen dissolved in the incomplete Freund's adjuvant. After several boosts, an immunoglobulin fraction was obtained from serum by chromatography with protein G-bound Sepharose (Pharmacia Biotech, Uppsala, Sweden).

Peptides were synthesized using standard solid phase chemistry, purified by reverse-phase HPLC and their identity verified by mass spectroscopic analysis (Research Genetics, Inc., Huntsville, Ala.).

For ELISA assays, recombinant soluble RANKL and TRAIL, and antibodies directed against these proteins were obtained from PeproTech (Rocky Hill, N.J.). Mouse monoclonal antibody (designated anti-FLAG M2) directed against the FLAG epitope was purchased from Upstate Biotechnology, Lake Placid, N.Y. Goat anti-rabbit IgG-alkaline phosphatase and rabbit anti-mouse IgG-alkaline phosphatase conjugates and paranitrophenolphosphate (pNPP) were purchased from Sigma (St. Louis, Mo.).

For bioassays, recombinant soluble RANKL was purchased from Peprotech, Rocky Hill, N.J., or residues 158-317 of murine RANKL were prepared as a GST-expressed protein. M-CSF was obtained from Research Genetics Institute (Boston, Mass., USA).

The M13 phage-displayed random peptide library was constructed as described (Adey et al. *Methods in Molecular and Cellular Biology* 6:3-14, 1995/1996).

Newborn (0-1-day-old) C57BL/6J mice and 6- to 9-week-old male C57BL/6J mice were purchased from Monash University Animal Services Centre (Clayton, Australia). The murine stromal cell lines, tsJ2, tsJ10 and tsJ14, were generated by transfection with a retroviral vector expressing a temperature-sensitive variant of the immortalizing gene of SV40 (ts A58; Chambers et al., *Proc Natl. Acad. Sci. USA* 90:5578-5582, 1993; Owens et al., *Biochem. Biophys. Res. Commun.* 222:225-229, 1996). RAW264.7 cells were purchased from the ATCC, and the cell lines KUSA/O and mc-3T3-e1 are described in Horwood et al. *Endocrinology* 139:4743-4746, 1998. Osteotropic agents regulate the expression of osteoclast differentiation factor and osteoprotegerin in osteoblastic stromal cells. $1\alpha,25(OH_2)$ vitamin $D_3$ was purchased from Wako Pure Chemicals Co. (Osaka, Japan). PGE2 was obtained from Sigma (St. Louis, Mo.). Other chemicals and reagents were of analytical grade.

2. Cell Culture

MDCK cells (American Type Culture Collection) were grown in Dulbecco's modified Eagle's medium (Life Technologies, Inc., Rockville, Md.) containing 10% fetal calf serum (Colorado Serum Company, Denver, Colo.) in 5% $CO_2$ at 37° C.

3. Screening of Peptide Phage Display Library

Isolation of phage containing sFRP-1-binding peptide segments on their surface was performed essentially as previously described (Sparks et al. Screening phage-displayed random peptide libraries, in *Phage Display Peptides and Proteins Eds*. B K Kay et al. Academic Press, New York, 227-253, 1996). In brief, a single well in a 96-well ELISA plate (Costar #3590, polystyrene surface) was incubated for 1 hour with purified recombinant sFRP-1 (1 µg/50 µl). This and all other manipulations with ELISA plates were conducted at room temperature. Subsequently, 150 µl of 1% BSA was added to the well and incubated for 2 hours. Following 3 washes with PBS/0.1% Tween 20, $2.5 \times 10^{10}$ phage from the M13 random 12-mer phage display library were added to the pre-coated well and incubated for 3.5 hours. After 1 wash with PBS/0.1% Tween 20, the well was incubated for 10 minutes with 50 µl of 0.05 M glycine pH 2 to release phage from the surface. The phage suspension was aspirated from the well, neutralized with 50 µl of 0.2 M sodium phosphate, pH 7.4, and amplified for 6-8 hours in DH5aF'IQ bacterial broth.

Amplified phage recovered from bacterial broth after this first enrichment step were subjected to two more rounds of panning in wells coated with sFRP-1 as described in the previous paragraph, except that the phage were incubated for only 2 hours and 1 hour in the second and third panning steps, respectively. After the third round of panning, phage obtained from the sFRP-1-coated well were titered and seeded on a lawn of bacteria to permit isolation of phage from 200 separate colonies. Bacteria from each of these colonies were grown in broth, pelleted by centrifugation and phage retrieved in the supernatant. Each of these phage supernatants was tested for binding to sFRP-1-coated ELISA wells versus wells only coated with the BSA blocking solution. Phage were detected in this assay with primary antibody directed against phage coat protein (Pharmacia Biotech, Uppsala, Sweden, #27-9411-01) and standard detection reagents. Approximately 100 phage isolates were selected for sequence analysis, based on exhibiting at least 5-fold higher binding to sFRP-1 versus BSA coated wells.

4. Sequence Analysis of Peptide Segments Present on the Surface of Isolated Phage The sequence of the DNA insert encoding the peptide segment linked to the M13 gene III coat protein from each phage isolate was determined by using sequencing primers corresponding to adjacent vector sequence. An advanced BLAST search analysis of GenBank databases was performed to identify proteins that contained sequences matching portions of the peptide sequences identified by screening of the peptide phage display library.

5. Generation of Peptide/Alkaline Phosphatase Chimeric Molecules

Synthetic oligonucleotides encoding peptides of interest were ligated into the bacterial alkaline phosphatase fusion vector, pMY101, which had been digested with SalI and XhoI (Yamabhai and Kay, *Anal Biochem*. 247:143-151, 1997). All recombinants were confined by DNA sequence analysis. Bacteria (*E. coli*, strain DH5αF') transformed with the peptide/AP constructs were grown in Luria broth containing ampicillin (50 µg/mL) to an optical density of 0.5 (at 600 nm), treated with 1 mM isopropyl-β-D-thiogalactopyranoside and then incubated overnight at 37° C. Conditioned medium containing peptide/AP chimera was recovered by centrifugation at 7000 g for 15 minutes. Chimeric proteins in conditioned medium were stable when stored for a few weeks at 4° C. or for several months when stored at −80° C.

6. ELISA Analysis of Peptide and Protein Binding to sFRP

ELISA experiments were generally performed as previously described (Uren et al., *J. Biol. Chem*. 275:4374-4382, 2000), with modifications depending on the sFRP binding partner to be tested. Typically, wells were coated with 0.5 or 1 µg of sFRP-1, blocked with BSA (0.2%, 1%, or 4%) and then incubated with putative binding partner overnight at room temperature. When investigating the binding of peptide/AP chimeras, after aspiration of bacterial broths, wells were washed and incubated with p-nitrophenolphosphate (pNPP). Color development was determined at 405 nm with an ELISA reader. For competition experiments, soluble peptides were preincubated with peptide/AP chimeras in bacterial broth for 30 min at room temperature prior to transfer into ELISA wells coated with sFRP-1 or BSA. When testing RANKL binding to sFRP-1, serial dilutions of soluble RANKL were assayed in replicate. Following overnight incubation at room temperature, RANKL solutions were aspirated and bound RANKL was detected by sequential incubations with primary antibody to RANKL, secondary antibody coupled with AP and pNPP. Similar experimental designs were employed when other TNFα family members were examined for binding to sFRPs, and when sFRP-1 derivatives or sFRP-2 were the binding targets for RANKL.

7. Isothermal Titration Calorimetry (ITC)

ITC experiments were performed with a VP-ITC Micro-Calorimeter MicroCal, LLC, Northhampton, Mass.) according to the manufacturer's User Manual. In brief, 6 µl aliquots of A-C2 (200 µM, dissolved in PBS) were injected at regular intervals into a chamber containing sFRP-1 (10 µM, also in PBS). Increases in temperature of the chamber resulting from the binding of A-C2 and sFRP-1 were determined as a measure of the heat produced by the binding reaction. Several parameters, included enthalpy and dissociation constant, were calculated from these measurements. This technique is commonly used to quantify the thermodynamic properties of binding interactions between proteins and peptides. For instance, see article by McNemar et al., Biochemistry 36:10006-10014, 1997.

8. Differential Display PCR

Total cellular RNA was extracted from cell lines or mouse tissues using guanidine thiocyanate-phenol chloroform and used for reverse transcriptase PCR (RT-PCR) essentially as described (Southby et al., *Endocrinology* 137:1349-1357, 1996 and Traianedes et al., *J. Biol. Chem*. 270:20891-20894, 1995). ddPCR was performed essentially as described (Liang et al., *Science* 257:967-971, 1992 and Traianedes et al., *J. Biol. Chem*. 270:20891-20894, 1995), except 1 µg of total RNA was reverse transcribed. PCR products were cloned into pCRScriptII (Stratagene, LaJolla, Calif.) or pGEM-T (Promega, Madison, Wis.). DNA sequence analysis was performed using a T7 sequencing kit (Pharmacia Biotech, Uppsala, Sweden). Oligonucleotides were synthesized on an Oligo 1000M DNA Synthesizer (Beckman Instruments Inc., Fullerton Calif., USA). The oligonucleotides were: for ddPCR, DDMR-2 (5'-CTTGATTGCC-3'; SEQ ID NO: 37) and T12VA (5-TTTTTTTTTTTT[A,C,G]A; SEQ ID NO: 32-3').

For ddPCR, the 3' oligonucleotide is T12VC, where V=A, C, or G. This oligonucleotide would anneal to mRNA transcripts having G and B (B=C, G, or T) as the ultimate and penultimate nucleotides prior to the poly A tail. Partial cDNA fragments were amplified using 5'-10 mers resulting in the synthesis of varying length cDNAs due to random annealing to different reverse transcribed mRNA species. This PCR reaction is performed at an annealing temperature of 40° C. and in the presence of $[\alpha^{35}S]$-dATP to allow the visualization of resulting products. The PCR products were resolved on 6% polyacrylamide sequencing gels and exposed to X-ray film for 1-3 days. Differentially regulated cDNA fragments were excised from the gel by overlaying the film and cutting out the region of interest Using the same oligonucleotides, the cDNA fragment was reamplified by two rounds of PCR (a total of 80 cycles of PCR). The reamplified product was then molecularly cloned into pGEM-T (Promega Inc., Madison, Wis.), and the nucleic acid sequence of the amplified insert was determined.

9. sFRP-1 Expression Analysis by RT-PCR

Total RNA isolated from cell lines or tissues was reverse transcribed with oligo-dT and PCR performed with the primers sfrp-1a (5'-TTAAAATTGCTGCCTGCCTGAG-3'; SEQ ID NO: 38) and sfrp-1b (5'-TCCGAACTACAGGGACAA-CAGG-3'; SEQ ID NO: 39) for 22 cycles, which was found to be in the log-linear phase of amplification for sFRP-1 transcripts from osteoblastic sources. Amplifications were performed according to manufacturer's instructions. Resultant PCR products were electrophoresed, transferred to nylon membrane, and hybridized with α-$^{32}$P-labeled internal detection oligonucleotide, sfrp-1c (5'-GCCCAGAGGTATTTCT-CAAAGTTG-3'; SEQ ID NO: 39). gapdh-2 (5'-ATGAG-GTCCACCACCCTGTT-3'; SEQ ID NO: 33, nucleotides 640-659; Tso et al., *Nucl. Acids Res.* 13:2485-2502, 1985) and gapdh-4 were used to amplify the normalizing gene, glyceraldehyde-3-phosphate dehydrogenase, by 20 cycles of PCR and products were detected with α-$^{32}$P-labeled gapdh-1 as described (Suda et al., *J. Cell. Physiol.* 166:94-104, 1996).

10. SFRP-1 In Situ Hybridization Analysis of Tissue Specimens

A murine sFRP-1 riboprobe was generated by PCR using RNA derived from tsJ2 cells. The resultant fragment of 750 bp was cloned into pGEM-T (Promega, Madison, Wis., USA). The plasmid was linearized and transcribed with T7 or SP6 RNA polymerase to generate antisense or sense riboprobes. The riboprobes were labeled with digoxigenin (DIG) during RNA transcription using a RNA labeling kit (Boehringer Mannheim, Mannheim GmbH, Germany) according to the manufacturer's instructions. In situ hybridization was performed as previously described (Kartsogiannis et al., *Bone* 21:385-392, 1997).

11. Osteoclastogenesis Bioassays

A. Co-culture Systems

Osteoblastic cells were prepared from the calvaria of newborn mice by digestion with 0.1% collagenase (Worthington Biochemical Co., Freefold, Australia) and 0.2% dispase (Godo Shusei, Tokyo, Japan). Bone marrow and spleen cells were obtained from adult and from newborn mice, respectively (Udagawa et al., *J. Exp. Med.* 182: 1461-1468, 1995). Osteoblastic cells were co-cultured with bone marrow or spleen cells as described previously (Udagawa et al., *J. Exp. Med.* 182: 1461-1468, 1995,). In short, primary osteoblastic cells (2×10$^4$/well) and nucleated spleen cells (1×10$^6$/well) or marrow cells (5×10$^5$/well) were co-cultured in 48-well plates (Corning Glass Inc., Corning, N.Y.) with 0.4 mL of α-MEM (GIBCO/BRL, Grand Island, N.Y.) containing 10% fetal bovine serum (Cytosystems, Castle Hill, NSW, Australia) in the presence of test chemicals. Cultures were incubated in quadruplicate and cells were replenished on day 3 with fresh medium. Osteoclast formation was evaluated after culturing for 6-7 days. Adherent cells were fixed and stained for tartrate-resistant acid phosphatase (TRAP), and the number of TRAP-positive osteoclasts was scored as described (Udagawa et al., *J. Exp. Med.* 182: 1461-1468, 1995). For TRAP staining, adherent cells were fixed with 4% formaldehyde in PBS for 3 minutes. After treatment with ethanol-acetone (50/50, vol/vol) for 1 minute, the well surface was air dried and incubated for 10 minutes at room temperature in an acetate buffer (0.1 M sodium acetate, pH 5.0) containing 0.01% naphthol AS-MX phosphate (Sigma) as a substrate and 0.03% red violet LB salt (Sigma) as a stain for the reaction product in the presence of 50 mM sodium tartrate. TRAP-positive cells appeared dark red, and those with three or more nuclei were scored as multinucleated and considered as osteoclasts. Validation of osteoclast formation was achieved using the specific marker of calcitonin receptor (CTR) expression and bone resorption. CTR expression was determined either by autoradiography with $^{125}$I-salmon calcitonin or by immuno-histochemical localization using an array of antibodies we have developed as described by Quinn et al., *Bone* 25: 1-8, 1999.

B. RANKL-induced osteoclast formation from hematopoietic cells

In some instances, experiments were performed either with adult mouse spleen cells or with RAW264.7 cells treated with M-CSF and RANKL as described in Quinn et al., *Endocrinology* 139:4424-4427, 1998. Where indicated, these assays were conducted in the presence or absence of splenic T cells. T cell fractions were prepared as described in Horwood et al., *Journal of Clinical Investigation* 101:595-603, 1998.

Example 2

Identification of Peptides that Bind sFRP-1

To identify peptide sequences that bind sFRP-1, ~25×10$^9$ phages from a library containing a diverse repertoire of twelve-amino acid residue segments linked to the gene III coat protein of M13 phage were screened. After three successive rounds of panning for phage that bound to ELISA wells preincubated with sFRP-1, the phage preparation selected for its ability to bind sFRP-1 was titered and then plated on a lawn of bacteria. Phage from 200 separate colonies of lysed bacteria were picked, grown in bacterial broth overnight, recovered in supernatant, and tested for their ability to bind preferentially to sFRP-1 versus BSA in an ELISA. Phage that bound at least five times more avidly to sFRP-1 than BSA-coated wells were subjected to nucleotide sequence analysis to determine the identity of the peptide sequence responsible for this binding specificity.

From the approximately 100 phage isolates that were sequenced, eleven unique peptide sequences were deduced. Of note, three of these eleven sequences contained a conserved motif consisting of the following seven amino acid residues: L/V-V-D-G-R-W-L/V (SEQ ID NO: 9). The significance of this heptapeptide motif was emphasized by the fact that two thirds of the phage exhibiting a high specificity for sFRP-1 in the ELISA displayed on their surface one of the three sequences with this motif (Table 1).

TABLE 1

| SEQ ID NO: | Reference Code | Amino Acid Sequence | Frequency | Specificity (sFRP-1/BS |
|---|---|---|---|---|
| 10 | A-C2 | QGT<u>LVDGRWL</u>QL SEQ ID NO: 14 | 54 | 10:1 |
| 11 | A-E4 | <u>VVDGRWV</u>QGLED SEQ ID NO: 11 | 9 | 10:1 |
| 27 | B-B9 | <u>LVDGRWL</u>YNPHH SEQ ID NO: 12 | 4 | 5:1 |

Because of the predominance of this pattern, the binding properties of these three peptides, designated A-C2 (SEQ ID NO: 14), A-E4 (SEQ ID NO: 11), and B-B9 (SEQ ID NO: 27), and the overall significance of the peptide motif was further examined. Subsequently, a similar analysis was performed with the second mostly frequently observed sequence identified by peptide phage display analysis, which was designated A-D9: WECAMYDGRCLT (SEQ ID NO: 40).

Example 3

Confirmation of sFRP-1 Peptide Motif Binding Activity

Figure 1:
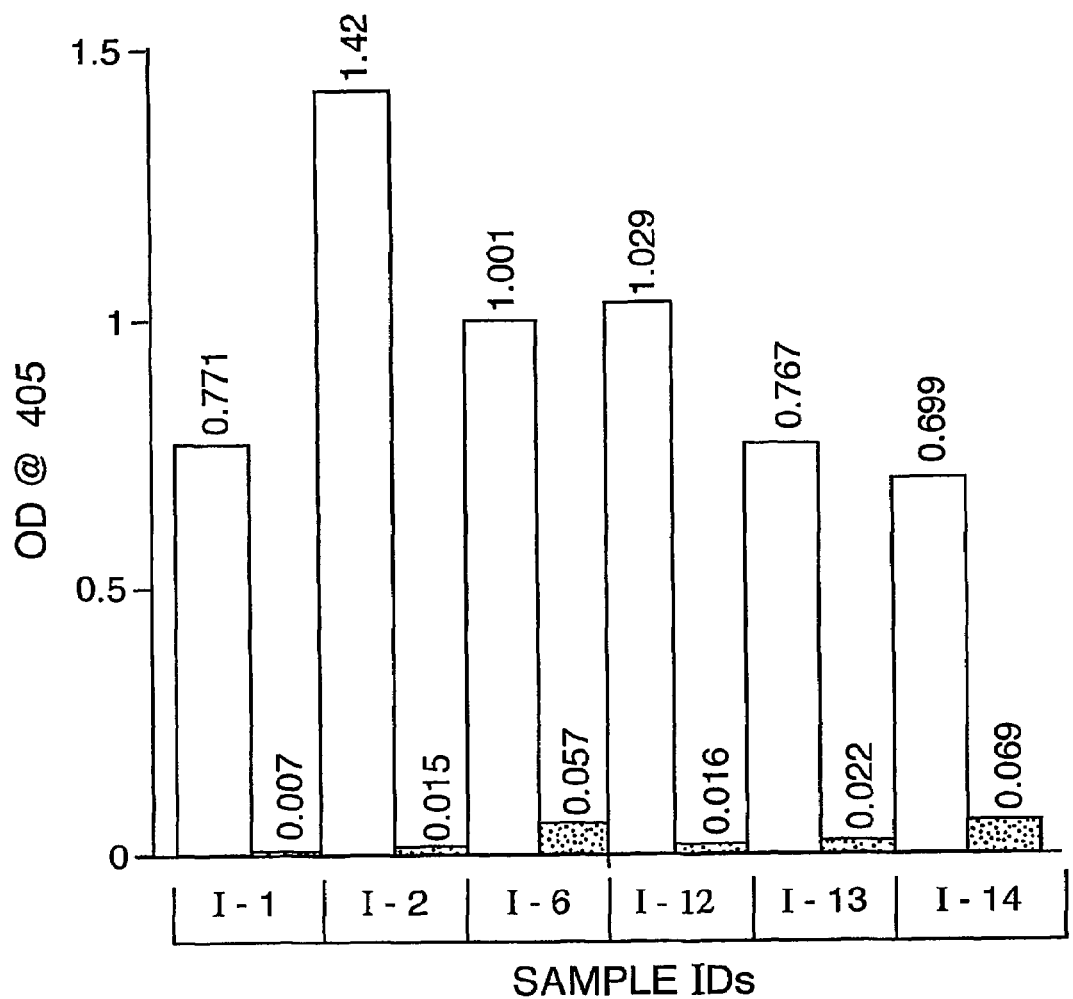
FIG. 1 is a graph showing the results from A-C2 (SEQ ID NO: 14)/AP (alkaine phosphatase) fusion protein binding t sFRP-1 (SEQ ID NO: 3). Broths from separate bacterial colonies infected with phage expressing the A-C2/AP chimera were incubated in ELISA wells coated with sFRP-1 (and subsequently blocked with BSA) or BSA alone. Each of the broths (identified as I-1, I-2, I-6, I-12, I-13 and I-14) contained AP activity, as measured by reaction with pNPP and color development at 405 nm, that bound specifically to the sFRP-1 (SEQ ID NO: 3)-coated wells (gray bars) as compared to the wells coated only with BSA (black bars). Each sample was tested singly; this is representative of several experiments.

A set of peptide-alkaline phosphatase fusion proteins containing the peptide motifs (SEQ ID NOS: 10, 11, and 27) were generated. These fusion proteins were tested for specific binding to sFRP-1 (SEQ ID NO: 3) in an ELISA format. As illustrated in FIG. 1, broths from multiple isolates of the A-C2 (SEQ IN NO: 14)/alkaline phosphatase fusion protein all showed strong, highly specific binding to wells preincubated with sFRP-1. Similar results were obtained with the A-E4 (SEQ ID NO: 11)/alkaline phosphatase fusion protein. However, the B-B9 (SEQ ID NO: 27)/alkaline phosphatase fusion protein did not exhibit specific binding to sFRP-1. This qualitative difference between A-C2 (SEQ ID NO: 14), A-E4 (SEQ ID NO: 11), and B-B9 (SEQ ID NO: 27) derivatives was consistent with a quantitative difference noted during the ELISA screening of the respective phage. The A-C2- (SEQ ID NO: 14) and A-E4- (SEQ ID NO: 11) expressing phage were more abundant in the phage preparation selected for sFRP-1 binding (Table 1) and showed a higher ratio of sFRP-1:BSA binding than B-B9 (SEQ ID NO: 27) phage. The more dramatic contrast observed with the fusion proteins is attributable to the difference in valency of the binding entities: each phage particle has five copies of the peptide displayed on its surface, whereas the peptide-alkaline phosphatase fusion proteins exist as dimers in solution. Thus, the relatively weaker binding avidity of the B-B9 sequence as originally perceived with the pentavalent phage particle became more obvious when dimeric reagents were tested. These results indicate that binding associated with the peptide motif could be influenced by the composition of nearby amino acid residues.

Figure 2:
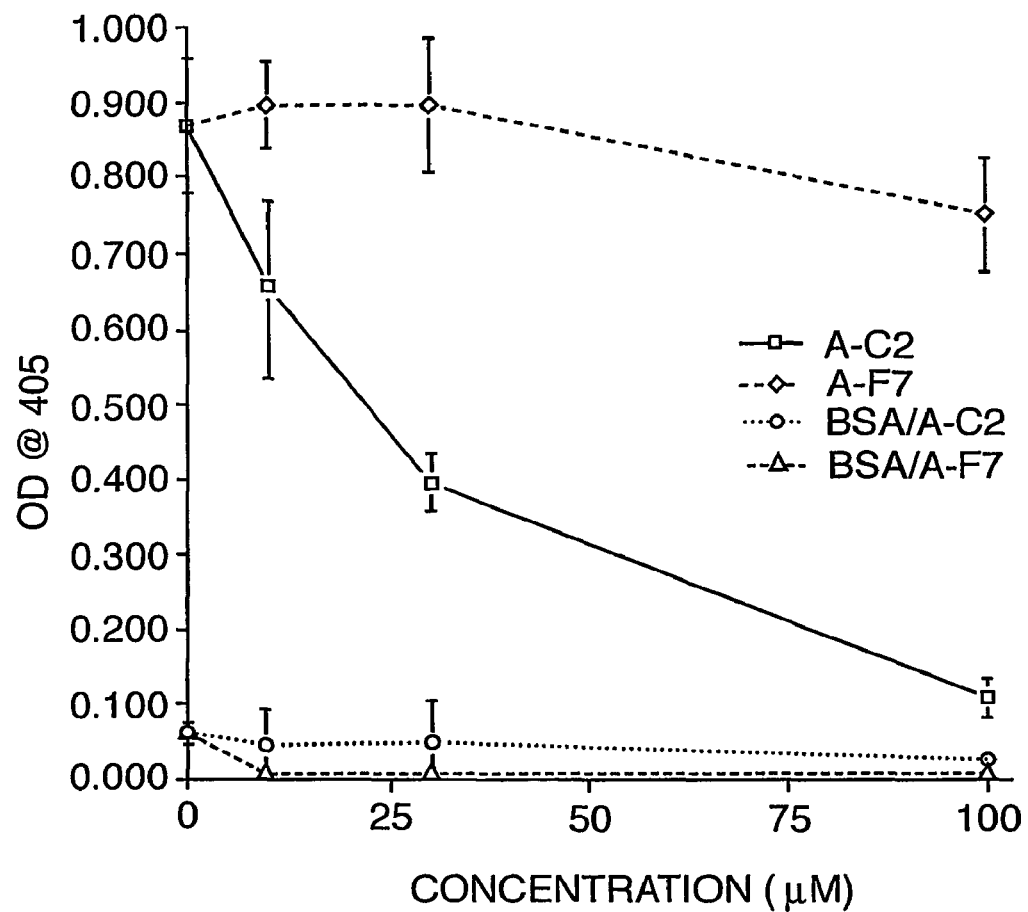
FIG. 2 is a graph showing the results from a competitive binding assay of A-C2/AP (SEQ ID NO: 14) and the 12-mer peptides A-C2 (SEQ ID NO: 14) and A-F7 (SEQ ID NO: 12) to either BSA or sFRP-1 (SEQ ID NO: 3). Soluble 12-mer peptides, A-C2 (SEQ ID NO: 14) and A-F7(SEQ ID NO: 12), were preincubated for 30 minutes at the indicated concentrations with bacterial broth containing A-C2/AP chimera prior to addition to ELISA wells coated with sFRP-1 (A-C2 open squares and A-F7 open diamonds) or BSA (A-C2 open circles and A-F7 open triangles). Samples were tested in triplicate, and results are shown as the mean +/−S.D. This is representative of three experiments.

Subsequent experiments demonstrated that the peptide motif (SEQ ID NO: 9) was a factor in the binding of the A-C2 (SEQ ID NO: 14)/alkaline phosphatase fusion protein to sFRP-1. For instance, dose-dependent inhibition of A-C2 (SEQ ID NO: 14)/alkaline phosphatase fusion protein binding to sFRP-1 was observed with A-C2 (SEQ ID NO: 14) but not with a control synthetic peptide (FIG. 2). Alkaline phosphatase itself showed no preferential binding to sFRP-1-coated wells. Individual substitutions of an alanine residue at each of the twelve sites in the A-C2 sequence (SEQ ID NO: 14) of the A-C2 (SEQ ID NO: 14)/alkaline phosphatase fusion protein established that all five core residues (V-D-G-R-W) of the native peptide motif enhanced sFRP-1 binding, as did the residues immediately flanking this core sequence (FIG. 3). Alanine substitutions at other sites also had an impact on binding, in some cases increasing the binding avidity for sFRP-1 (SEQ ID NO: 3).

Taken together, peptide phage display analysis followed by ELISA experiments with peptide/alkaline phosphatase fusion proteins established the existence of a peptide motif (SEQ ID NO: 9) that binds to sFRP-1. Moreover, binding of proteins containing this peptide motif, L/V-V-D-G-R-W-L/V (SEQ ID NO: 9), could be either enhanced or diminished by changes in the composition of residues in close proximity to the peptide motif (SEQ ID NO: 9).

Figures 4A, 4B:
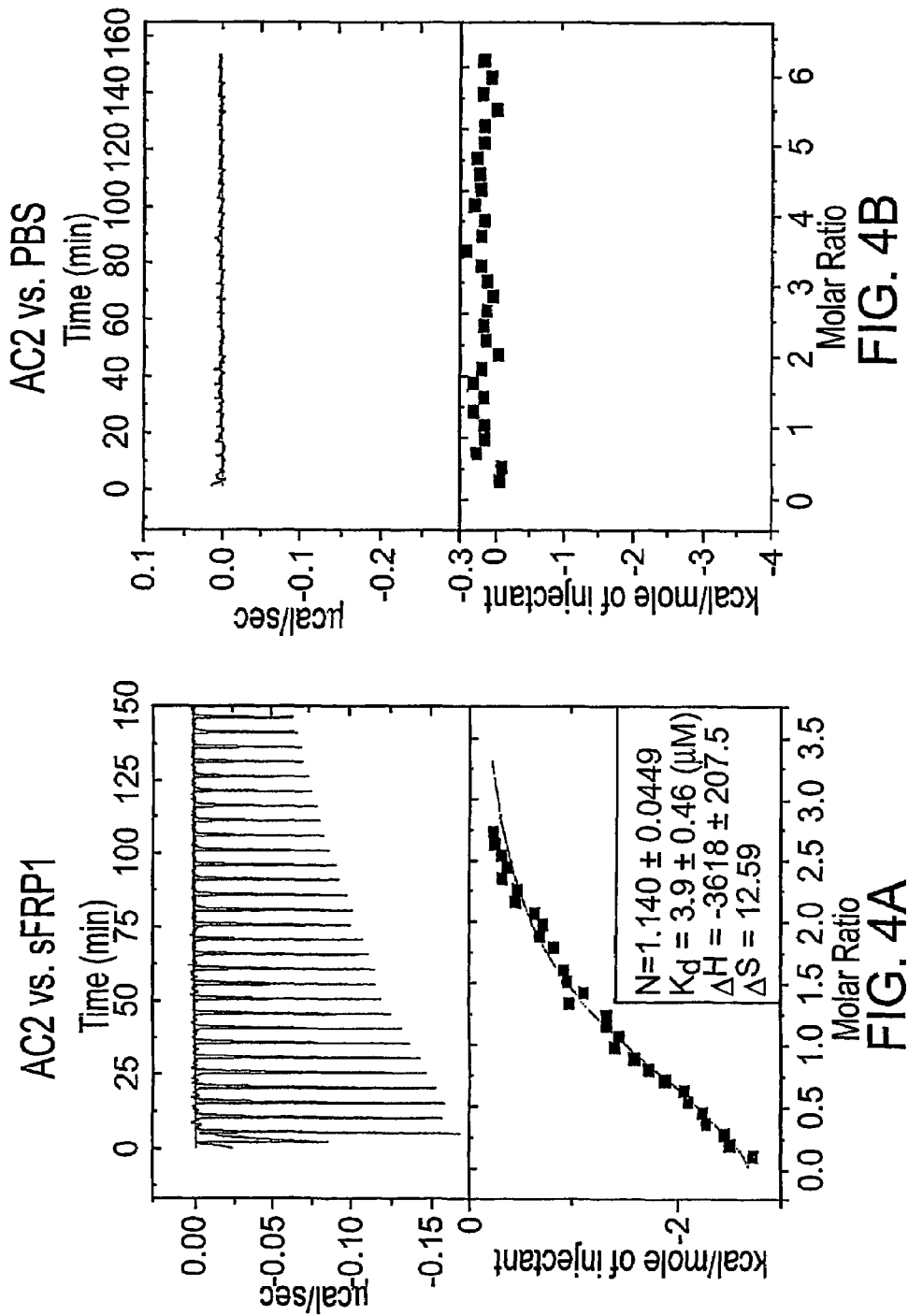
FIG. 4A is a tracing and plot showing the heat generated when aliquots of AC2 solution were added to a chamber containing sFRP-1 dissolved in PBS.
FIG. 4B is a tracing and plot of the heat generated in the corresponding PBS control. Based on the amount of heat released, various parameters of the binding reaction were calculated, including the enthalpy ($\Delta H$) and dissociation constant, Kd.

Isothermal titration calorimetry (ITC) was used to demonstrate binding of AC2 peptide and sFRP-1 in solution, and estimate affinity of the interaction. Binding was evident, as heat was generated when aliquots of AC2 solution were added to a chamber containing sFRP-1 dissolved in PBS. By contrast, no heat was produced when AC2 was added to a chamber containing only PBS. The calculated Kd was 3.9+/−0.46 micromolar (FIGS. 4A and 4B).

ELISA experiments were performed essentially as described above with a series of sFRP-1 deletion mutants (in Uren et al., *J. Biol. Chem.*, 275: 4374-4382, 2000) to determine what region(s) of the protein were required for binding to the AC2/alkaline phosphatase chimera. Optimal binding was observed with the Δ3 derivative, which contains all of the Fz CRD and a portion of the C-terminal region. Little binding was detected with derivatives that contained the CRD alone or the C-terminal region alone.

Thus, a combination of elements from the CRD and the C-terminal domain were required for AC2 binding. As derivatives that did not bind well to the AC2 chimera bound other reagents, and in some instances showed biological activity, they are unlikely to be simply misfolded.

Another peptide, A-D9, was analyzed in a manner similar to the routine followed for A-C2. In particular, ELISA experiments performed with an A-D9/AP chimera showed that this chimera bound specifically to wells coated with sFRP-1 rather than BSA. This binding was blocked in a dose-dependent manner with soluble synthetic peptide containing the A-D9 sequence. Binding of the A-D9/AP chimera to sFRP-1 in ELISA wells was disrupted by alanine substitutions in the A-D9 sequence. Interestingly, A-C2 peptide also could inhibit binding of the A-D9/AP chimera to sFRP-1 and the A-D9 peptide inhibited binding of the A-C2/AP chimera to sFRP-1. This implied that A-C2 and A-D9 recognized overlapping binding sites on sFRP-1, consistent with the presence of a common element (DGR) in the two peptides.

Example 4

Identification of Proteins with Sequences Resembling the Peptide Motif

BLAST analysis of sequences in GenBank indicated that the newly discovered peptide motif (SEQ ID NO: 9) was not present in any Wnt proteins. However, similar sequences were observed in a handful of other proteins, as illustrated in Table 2.

TABLE 2

| SEQ ID NO: | Identified Protein with Homology to Peptide Motif | Amino Acid Sequence |
| --- | --- | --- |
| 29 | Netrin receptor (UNC5H3) | TLCPVDGRW |
| 28 | RANKL | MVDGSWLDL |
| 10 | ANP receptor A (human) | VVDGRFVLKITD |

The V-D-G-R-W segment in UNC5H3 was noteworthy because this protein is a netrin receptor. Thus, it is possible that sFRP-1 (SEQ ID NO: 3) interacts with UNC5H3 in a ligand/receptor relationship. The presence of the sequence M-V-D-G-S-W-L (SEQ ID NO: 28) in RANKL/TRANCE/OPGL also is notable because of additional evidence that sFRP-1 (SEQ ID NO: 3) and RANKL are co-expressed in many tissues, including bone where RANKL has a critical role in osteoclast formation (see below). The sequence V-V-D-G-R-F-V (SEQ ID NO: 10) in the human atrial natriuretic peptide (ANP) receptor A is also of significance because of the co-expression of this gene product and sFRP-1 in tissues within the kidney and eye. As described herein, sFRP-1 (SEQ ID NO: 3) and RANKL interact with each other in a manner that has significant biological consequences, and their interaction can be modulated to affect osteoclastogenesis.

Example 5 sFRP-1 and Expression in Bone

In situ hybridization analyses of sFRP-1 transcripts (SEQ ID NO: 1) in skeletal structures of mouse embryos (Day 19), newborn mice (Day 1) and adult mice (five weeks) were performed to examine the role of sFRP-1 in bone development. Hypertrophic chondrocytes were strongly positive in murine embryos (E19). In the spinal cord of Day 1 mice, there was very strong expression in the ossification center within the cartilage primordium of the lumbar vertebral body and the nucleus pulposus in the central part of the lumbar invertebral disc. In the adult, bone lining cells were positive as well as a number of isolated marrow cells, and osteocytes were weakly positive. sFRP-1 mRNA was also observed in the epidermis. RANKL is expressed in a similar pattern (Kartsogiannis et al., *Bone* 25:525-534, 1999). Expression of sFRP-1 in skeletal sites was also detected. Hence, it is likely that sFRP-1 is involved in skeletal morphogenesis and sFRP-1 expression continues in a number of sites through to adulthood.

sFRP-1 expression in osteoblasts (tsJJ2 cells) was studied (for a description of the tsJJ2 cell line and the tsJ14 cell line see Chambers et al., *Proc. Natl. Acad. Sci. USA* 90:5578-5582, 1993). The results showed that sFRP-1 is preferentially expressed in osteoblasts (tsJ2 cells) that promote osteoclast formation. Murine sFRP-1 transcripts were amplified using the oligonucleotides sfrp-1a and sfrp-1b. Amplified products were verified by Southern analysis using [α-$^{32}$P]dATP end-labeled oligonucleotide sfrp-1b as a probe. Differential display PCR (ddPCR) also showed that sFRP-1 is upregulated in osteoblast lines that stimulate osteoclastogenesis, but not in the products from two other lines that do not support osteoclast differentiation: Semi-quantitative RT-PCR analysis of sFRP-1 expression confirmed that transcript level was much higher in lines that were capable of promoting osteoclast formation in co-cultures with hematopoietic progenitor cells. This pattern was observed when additional osteoblast lines were compared, reinforcing the finding that sFRP-1 expression was associated with osteoclastogenesis.

However, in general, osteotropic factors such as 1α,25 (OH$_2$) vitamin D$_3$ caused limited stimulation of sFRP-1 expression by osteoblastic lines. Total RNA was isolated from either untreated or cells treated with 1α,25(OH$_2$) vitamin D$_3$ for 24 hours, reverse transcribed with oligo (dT), and subjected to PCR for murine sFRP1 and GAPDH. A co-culture of osteoblasts and bone marrow treated for 24 hours with 1α,25(OH$_2$) vitamin D$_3$ was included as a positive control. The primer combination of sfrp-1a (5'-AGC CTT GGC AGT CAA CGA CG-3' SEQ ID NO: 30) and sfrp-1b (5'-GTT GTG GCT TTT GCA TTG CAC-3' SEQ ID NO: 31) was used for sFRP-1 amplification and the primer combination of gapdh-2 (5'-ATG AGG TCC ACC ACC CTG TT-3' SEQ ID NO: 33) and gapdh-4 (5'-CAT GGA GAA GGC TGG GGC TC-3' SEQ ID NO: 34) was used for GAPDH amplification. The resultant PCR products were electrophoresed, transferred to nylon membrane and hybridized with [α-$^{32}$P]-labeled internal detection oligonucleotide, sfrp-1c (5'-TGT TGA AAA CTA GTA GCT G-3' SEQ ID NO: 35) and gapdh-1 (5'-GCT GTG GGC AAG GTC ATC CC-3' SEQ ID NO: 36), respectively, as described (Southby et al., *Endocrinology* 137:1349-1357, 1996). RT-PCR analysis was repeated in triplicate. Semiquantitative RT-PCR analysis was performed three times on each RT reaction and two independent RT reactions were examined.

These results indicate that sFRP-1 may be a mediator of hormonally dependent osteoclast formation. On the other hand, sFRP-1 expression increased markedly when osteoblasts and osteoclast progenitors were co-cultured. The time course of this increase matched the rise in appearance of TRAP+ cells, a marker of osteoclast differentiation. These results indicate that upregulation of sFRP-1 expression is dependent on cell-cell communication between the osteoblast and osteoclast lineages. In particular, the correlation between sFRP-1 expression and osteoclast formation suggested that sFRP-1 induction might be a consequence of osteoclastogenesis.

Example 6 sFRP-1 Blocks Osteoclastogenesis in Cell Culture Bioassays

Figure 5:
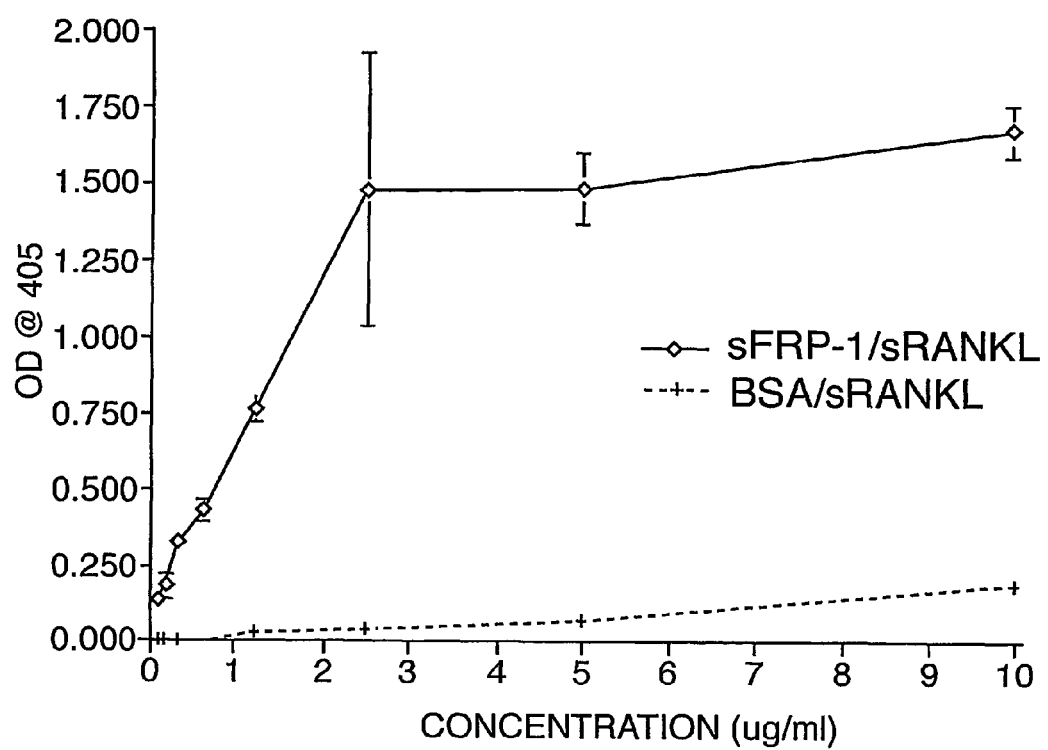
FIG. 5 is a graph showing the results from ELISA binding assays using soluble RANKL (sRANKL) and sFRP-1 (SEQ ID NO: 3). The open diamond represents sRANKL binding to sFRP-1, and the plus symbol "+" represents sRANKL binding to bovine serum albumin (BSA).

The possibility that sFRP-1 (SEQ ID NO: 3) and RANKL interact directly with each other was tested using an ELISA assay. The ELISA assay involved the use of wells that were coated with recombinant sFRP-1 (SEQ ID NO: 3) and subsequently blocked with BSA. RANKL was then incubated in these wells and in adjacent wells that had only been treated with BSA. Subsequent detection with RANKL antiserum and secondary reagents revealed that RANKL bound specifically to sFRP-1 (FIG. 5). This result was confirmed in several separate experiments. The use of recombinant reagents indicates that sFRP-1 (SEQ ID NO: 3) and RANKL bind directly to each other.

The effect of sFRP-1 was assessed upon a RANKL-independent method of osteoclast formation using the monocyte/macrophage cell line RAW264.7 (Quinn et al., *Journal of Bone and Mineral Research*. 16, 1787-1794, 2001) and was compared with that of osteoprotegerin (FIG. 14). In the absence of TGFα, only limited numbers of osteoclasts are produced form TNFα-treated RAW264.7 cells (Quinn et al., *Journal of Bone and Mineral Research*. 16, 1787-1794, 2001), so TGFβ was added during the first three days of culture to increase osteoclast numbers (FIG. 14). sFRP-1 inhibited TNFα-dependent osteoclast formation when present during the first three days of culture, whilst OPG had no effect suggesting that sFRP-1 was acting indirectly of RANKL, through binding to TNFα or through WNT signaling.

The effect of bacterially expressed CRD was assessed in three different cell culture models of osteoclast formation. These were: (1) bone marrow cells+RANKL+M-CSF, (2) the macrophage/monocyte cell line RAW264.7+RANKL, and (3) RAW264.7+TNFα+TGFβ (Horwood et al., *Journal of Immunology* 166:4915-4921, 2001; Quinn et al., *Journal of Bone and Mineral Research*. 16, 1787-1794, 2001). In each system, both RANKL-dependent (cultures 1 and 2) and RANKL-independent (culture 3, TNFα-dependent osteoclast formation), the bacterially expressed CRD mimicked the action of full-length sFRP-1 and with similar potency (FIG. 15).

As shown above, ELISA experiments with sFRP-1 deletion mutants indicated that the Δ1 derivative (Uren et al. *J. Biol. Chem.*, 275: 4374-4382,2000), which consists essentially of the Fz CRD, retained good binding to RANKL (see FIG. 12). In addition, RANKL binding to a preparation of bacterially expressed CRD was strong.

Scatchard analysis of the ELISA data indicates that there are two different binding sites: a high affinity site and a low-affinity site with affinities of 5-10 nM and 80-120 nM, respectively (see FIG. 13) (see Meshul et al., *J. Neurochem.* 67:1965, 1996).

Figure 6A:
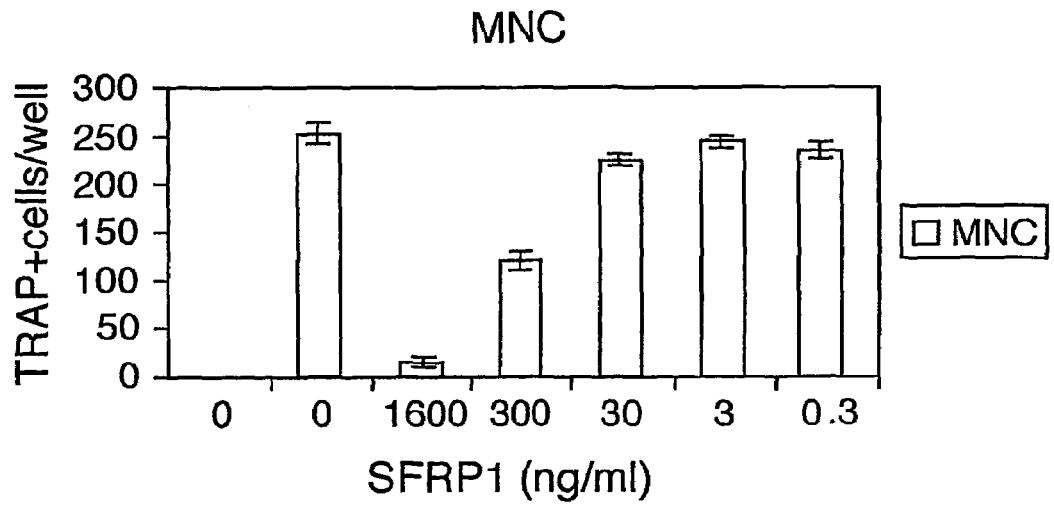
FIG. 6A is a graph showing results from co-culture experiments in which primary osteoblasts and bone marrow were incubated with varying concentrations of sFRP-1. Subsequently, wells were stained to determine the number of TRAP+ multinucleated cells (MNC). Results show that as the concentration of sFRP-1 increases, osteoclast maturation decreases (as is evident by decrease in TRAP+). The results shown are the mean +/−S.D. of quadruplicate measurements.
Figure 6B:
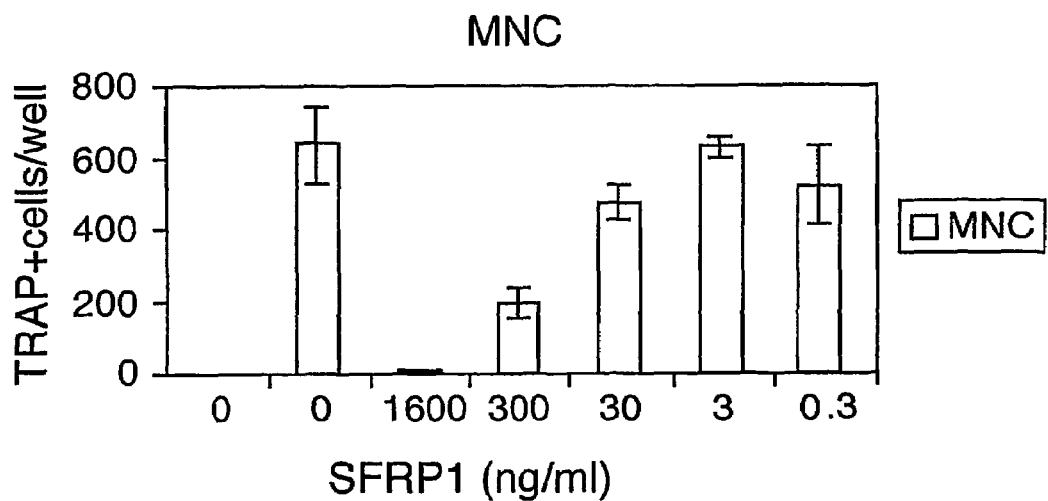
FIG. 6B is a graph showing the results from experiments in which adult spleen cells wer treated with RANKL, macrophage colony stimulating factor (M-CSF), and various concentrations of sFRP-1 (SEQ ID NO: 3). Subsequently, wells were stained to determine the number of TRAP+ multinucleated cells (MNC). The data presented is the mean +/−S.D. of quadruplicate measurements. Results show that as the concentration of sFRP-1 increases osteoclast maturation decreases.

Assays measuring the effect of sFRP-1 on osteoclastogenesis showed that sFRP-1 has a dose-dependent inhibitory activity on osteoclast formation (FIG. 6A). These results were observed in co-cultures of primary osteoblasts and bone marrow cells treated with vitamin D3 ($10^{-8}$ M) and PGE2 ($10^{-7}$ M). sFRP-1 reduced the number of multinucleated TRAP+ cells by 50% when used at a concentration 300 ng/mL, while a dose of 1.6 ug/mL decreased the number of cells by 95% (FIG. 6A). A similar dose-response pattern was observed when adult mouse spleen cells were treated with RANKL and M-CSF (FIG. 6B). These results indicate that a direct interaction between sFRP-1 and RANKL blocked osteoclast differentiation.

Figure 7A:
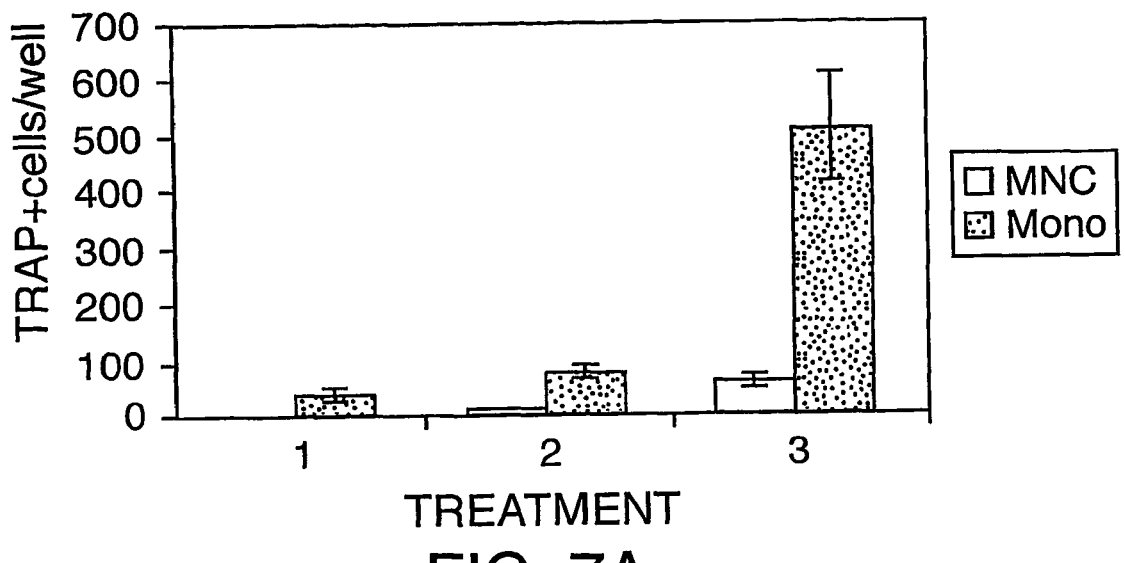
FIG. 7A is a graph showing that sFRP-1 specific antibody binding to sFRP-1 causes an increase in osteoclast formation Osteoclast formation, as measured by TRAP+ staining, was assessed in co-cultures of primary osteoblasts and adult spleen cells without hormonal supplements or with suboptimal doses of $1\alpha,25(OH_2)$ vitamin $D_3$ ($10^{-10}M$) and dexamethasone ($10^{-9}M$) in the presence or absence of purified immunoglobulin (~2 μg/mL) from a rabbit immunized with recombinant sFRP-1. The results are the mean +/−S.D. of mononucleated and multinucleated TRAP+ cells detected in quadruplicate samples after 7 days in culture.
Figure 7B:
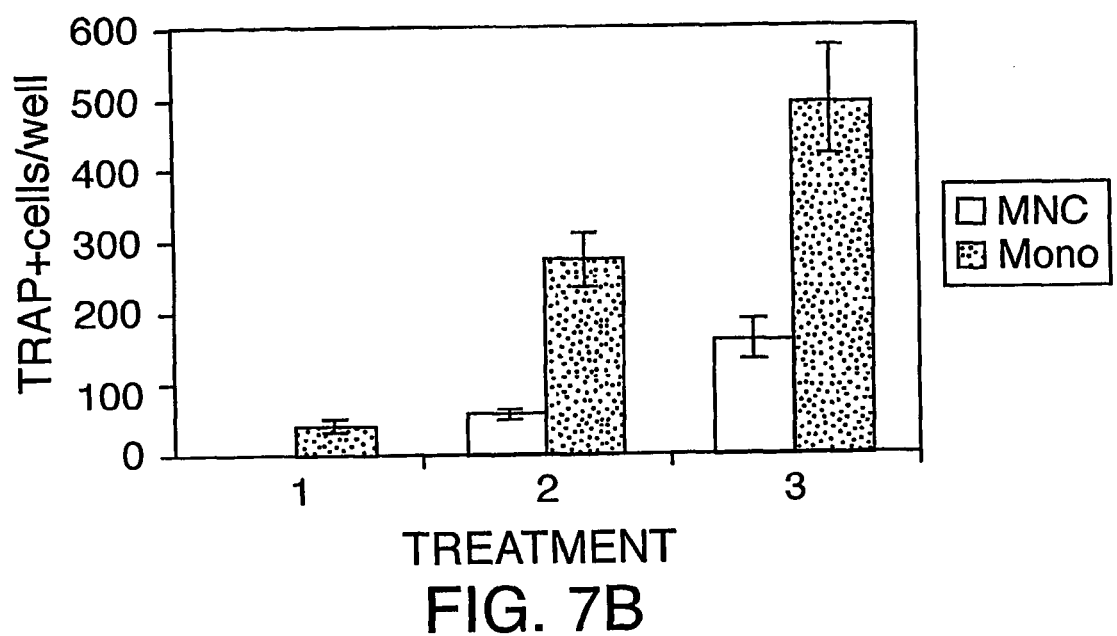
FIG. 7B is a graph showing that sFRP-1 specific antibodies bind to sFRP-1 and cause an increase in osteoclast formation in the presence of optimal doses of $1\alpha,25(OH_2)$ vitamin $D_3$ ($10^{-8}$ M) and prostaglandin E2 (PGE2) $10^{-7}$ M. Osteoclast formation, as measured by TRAP+ staining, was assessed in co-cultures of primary osteoblasts and adult spleen cells without hormonal supplements or with optimal doses of $1\alpha,25(OH_2)$ vitamin $D_3$ ($10^{-8}M$) and prostaglandin E2 (PGE2, $10^{-7}M$) in the presence or absence of purified immunoglobulin (~1 μg/mL) from a rabbit immunized with recombinant sFRP-1. The results are the mean +/−S.D. of mononucleated and multinucleated TRAP+ cells detected in quadruplicate samples after 7 days in culture.

The significance of data obtained with recombinant sFRP-1 was strengthened by the results of experiments performed with protein G-purified rabbit polyclonal antibodies raised against recombinant sFRP-1. This antibody preparation caused a seven- to ten-fold increase in mononucleated and multinucleated TRAP+ cells in co-cultures of primary osteoblasts and adult spleen cells that had been treated with submaximal does of D3 ($10^{-10}$ M) and Dex ($10^{-9}$ M) (FIG. 7A). Approximately a two to three-fold increase in these cells was observed in co-cultures receiving optimal doses of D3 ($10^{-8}$ M) and PGE2 ($10^{-7}$ M) (FIG. 1). These results indicated that naturally occurring sFRP-1 was present in the cultures and inhibited osteoclast formation. By neutralizing this endogenous activity, sFRP-1 antibodies boosted the number of TRAP+ cells produced in the co-cultures.

Bacterially expressed CRD blocked osteoclast formation in three different cell culture models, mimicking action of full-length sFRP-1 and with similar potency (FIG. 14) The three conditions used in these assays were: (1) bone marrow cells+RANKL+M-CSF, (2) RAW264.7+RANKL, and (3) RAW264.7+TNFα+TGFβ. Without being bound by theory, as activity was seen in group (3) (in the absence of RANKL), it is possible that that CRD binds to TNFα, which is structurally-related to RANKL.

Example 7

A-C2 Synthetic Peptide Promotes Osteoclast Formation

Figure 8:
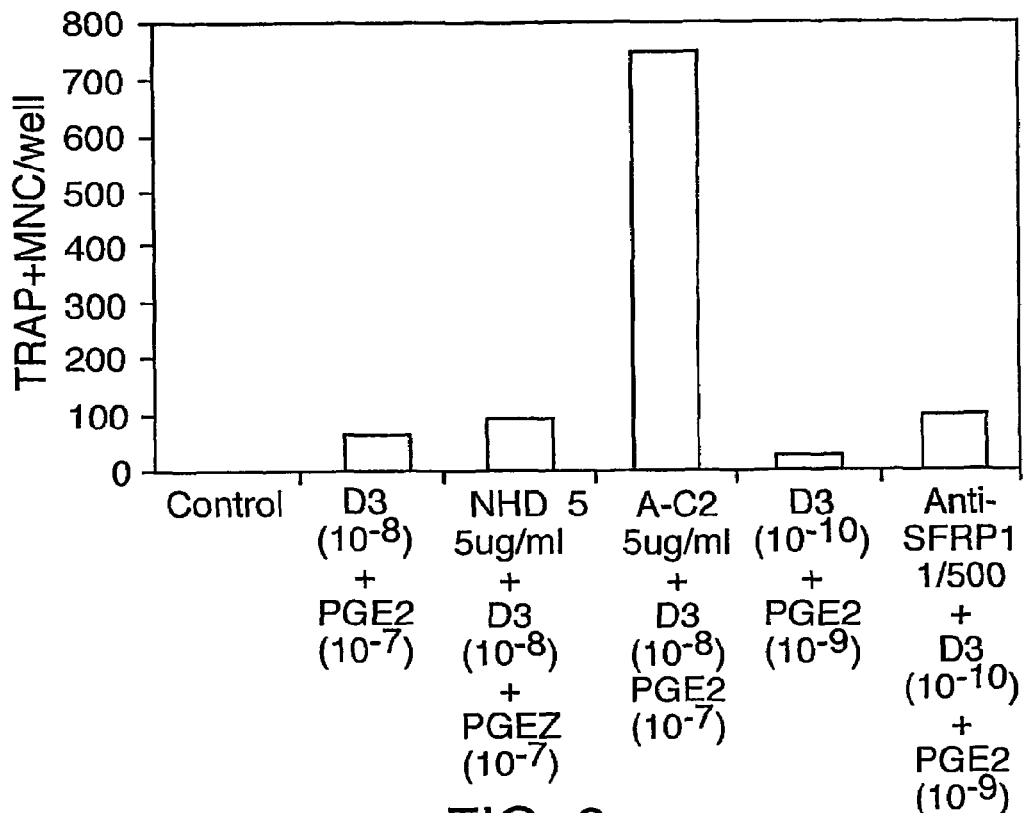
FIG. 8 is a graph showing that A-C2 peptide stimulates osteoclast formation in co-cultures of osteoblasts and adult spleen cells. Osteoclast formation in response to optimal doses of $1\alpha,25(OH_2)$ vitamin $D_3$ ($10^{-8}M$) and PGE2 ($10^{-7}M$) was not further enhanced by the concomitant addition of the netrin homology domain (NHD) domain of sFRP-1 (SEQ ID NO: 13; 5 μg/mL), but it was markedly stimulated by simultaneous incubation with the A-C2 peptide (SEQ ID NO: 14; 5 μg/mL). As a positive control for enhanced osteoclastogenesis, cells were treated with suboptimal doses of $1\alpha,25(OH_2)$ vitamin $D_3$ ($10^{-10}M$) and PGE2 ($10^{-9}M$) in the absence or presence of sFRP-1 specific antibody ⅕₀₀. The bar graph shows the mean +/−S.D. of TRAP+ multinucleated cells tested in quadruplicate.
Figure 9:
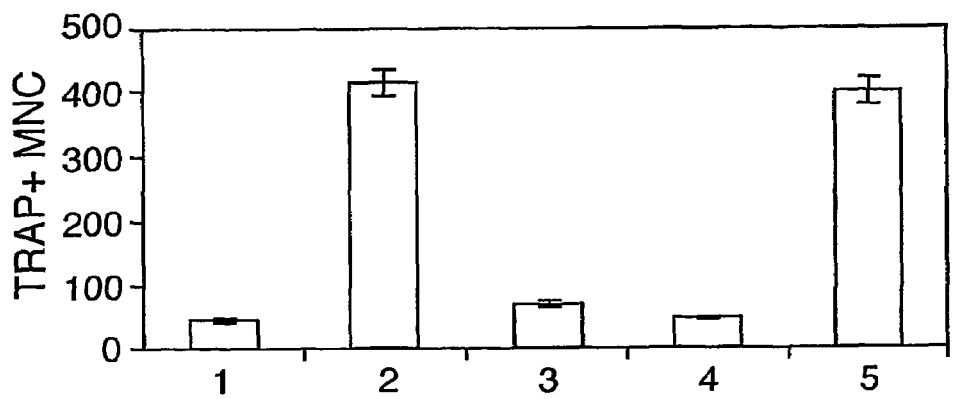
FIG. 9 is a graph showing the results from an experiment in which A-C2 (SEQ ID NO: 14) was incubated for various time periods with adult spleen cells. Group 1 was the control that did not contain A-C2 (SEQ ID NO: 14) peptide. Group 2 was treated with A-C2 (SEQ ID NO: 14) from day 0-3, group 4 was treated with A-C2 (SEQ ID NO: 14) from day 4-7, group 4 was treated with A-C2 (SEQ ID NO: 14) from day 7-10, and group 5 was treated with A-C2 (SEQ ID NO: 14) from day 0-10. All treatment groups received RANKL at 50 ng/mL and M-CSF at 25 ng/mL. A-C2 (SEQ ID NO: 14) presence during days 0-3 caused an increase in osteoclast production.

Because the A-C2 (SEQ ID NO: 14) polypeptide has sequence homology to RANKL and because A-C2 (SEQ ID NO: 14) binds to sFRP-1, assays were performed to determine if A-C2 (SEQ ID NO: 14) would block sFRP-1 binding to RANKL and thus increase osteoclastogenesis. Consistent with this hypothesis, treatment of osteoblast and adult spleen cell co-cultures with A-C2 (SEQ ID NO: 14) resulted in a ten-fold increase in TRAP+ multinucleated cells (FIG. 8). A-C2 (SEQ ID NO: 14) only had an effect on osteoclast formation when it was present during day 0 to day 3 of the co-culture experiment. RANKL presence is also required for osteoclastogenesis during day 0 to day 3 (Suda et al., *Endocrine Reviews* 20:345-357, 1999). Thus, these results are consistent with the notion that A-C2 (SEQ ID NO: 14) most likely has an impact on RANKL activity.

Figure 10A:
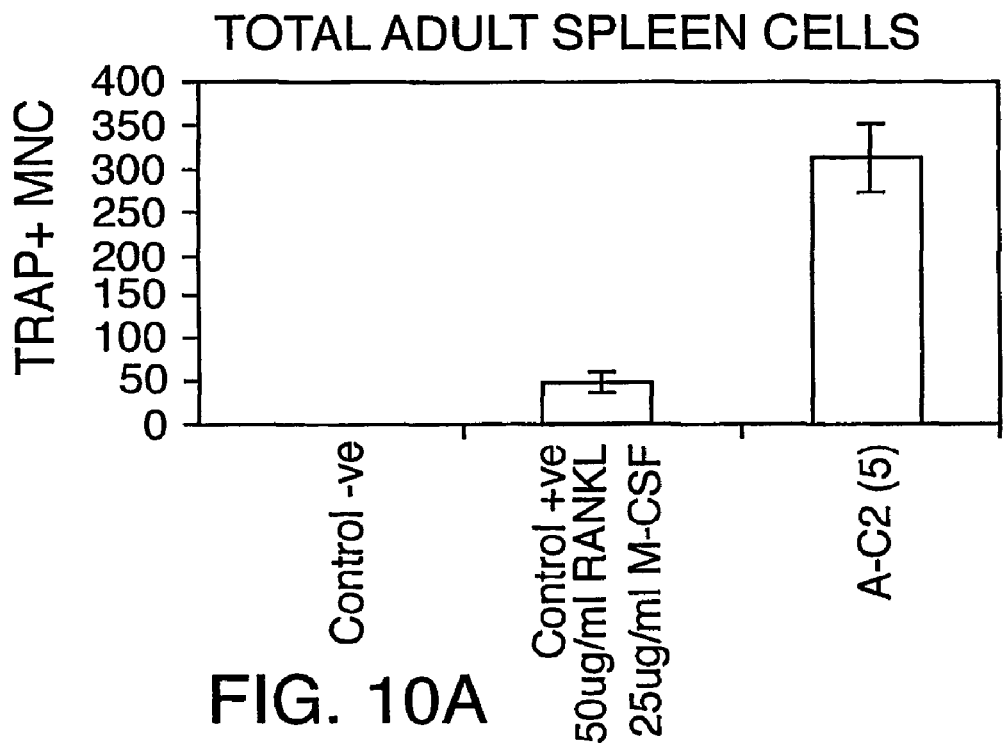
FIGS. 10A and 10B are graphs depicting the results from A-C2 (SEQ ID NO: 14) incubation with adult spleen cells containing T cells (FIG. 10A) and spleen cells without T cells (FIG. 14B): T cells were immunomagnetically separated frm the spleen cells. Osteoclast formation was induced by RANKL (50 ng/mL) and M-CSF (25 ng/mL) and assessed by counting TRAP+ multinucleated cells after nine days of culture. Osteoclast formation was measured in adult spleen cell cultures (FIG. 14A) or in culture lacking T cells (FIG. 10B) in the absence (Control +ve) or presence of A-C2 (5 mg/mL). These cultures do not contain any osteoblasts, thus effects of A-C2 were restricted to lymphocytic or hematopoietic cells. The bar graphs show the mean +/−S.D. of TRAP+ multinucleated cells from quadruplicate samples. Controls for this experiment included spleen cells [complete (FIG. 10A) or T cell depleted (FIG. 10B)] in the absence of RANKL and M-CSF (control −ve) and no osteoclasts were produced under these conditions. As a positive control for the assay system (Control +ve), cultures were treated with RANKL (50 ng/mL) and M-CSF (25 ng/mL), and the effects A-C2 addition is compared to this culture.
Figure 10B:
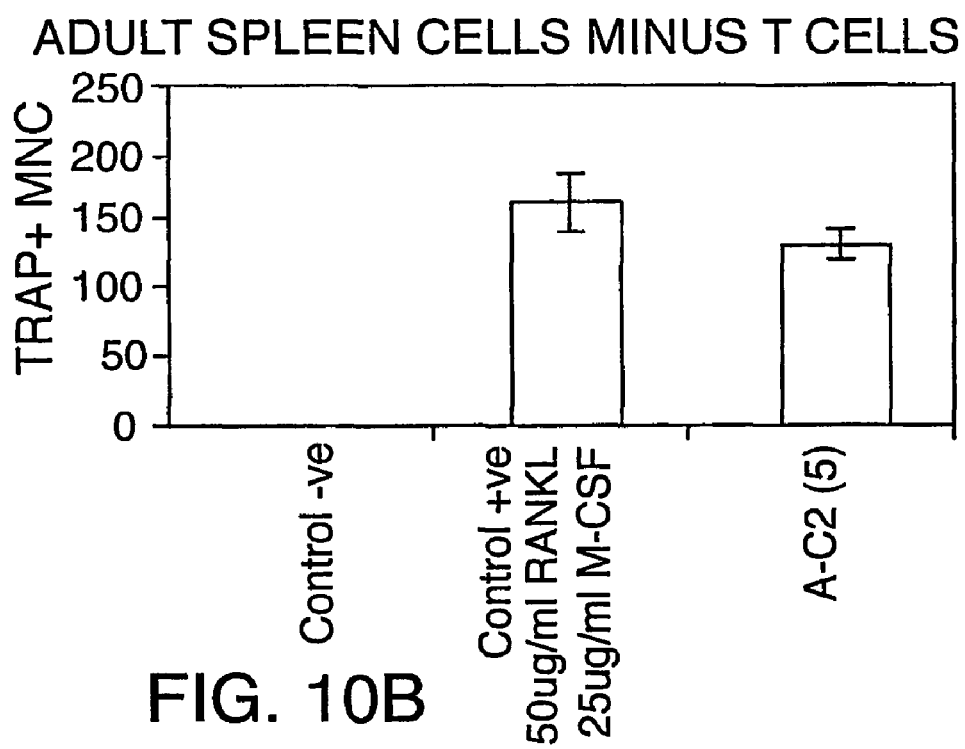
Figure 11A:
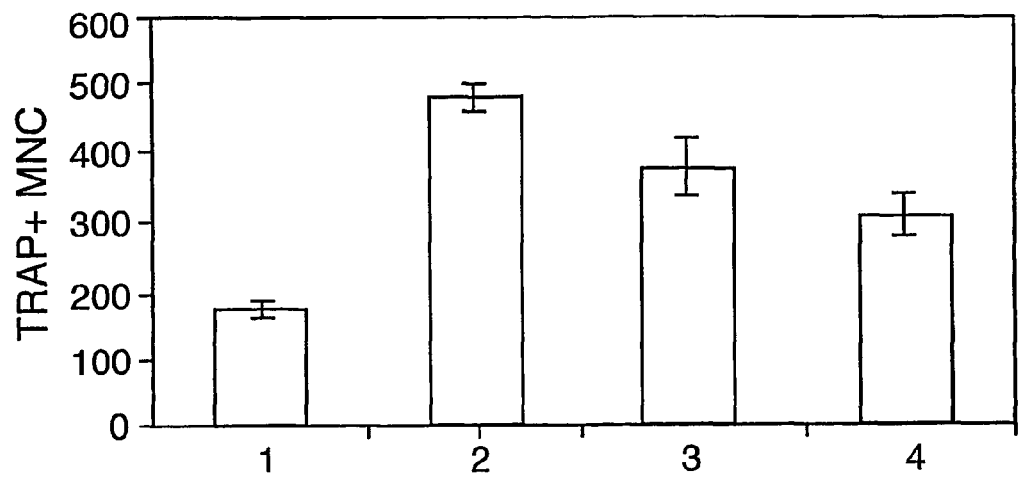
FIGS. 11A and 11B are graphs depicting the A-C2 (SEQ ID NO: 14) stimulation of TRAP+, multinucleated cell differentiation in RAW264.7 (TIB-71) cell cultures. Group 1 was the positive control that contained 50 ng/mL RANKL. Groups 2, 3, and 4, contained 50 ng/mL RANKL and either 5
Figure 11B:
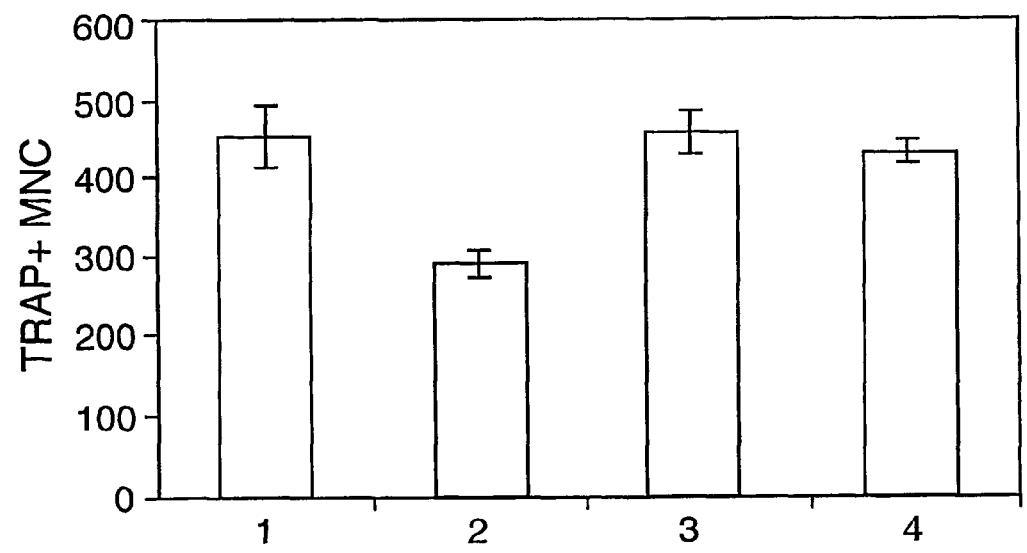
Figure 13A:
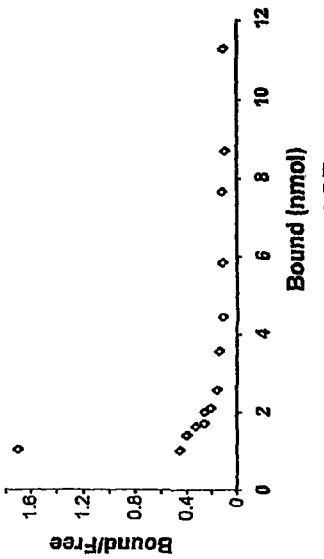
Figure 13B:
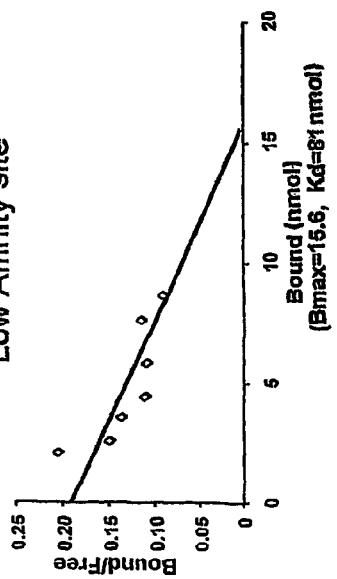
Figure 13C:
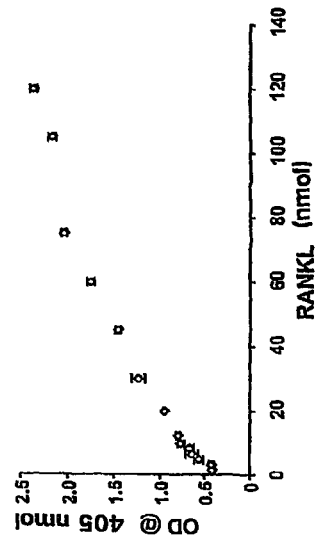
Figure 13D:
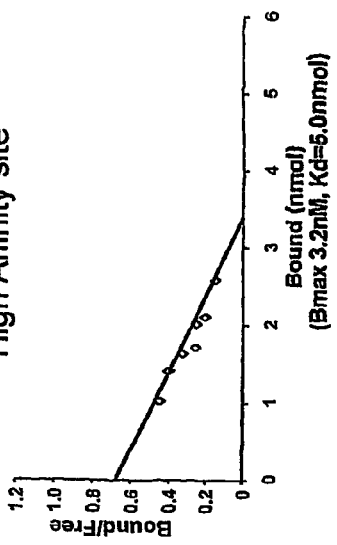

Additionally, the positive effect of A-C2 (SEQ ID NO: 14) in the co-culture assays was correlated with the presence of T cells. When T cells were removed from the adult spleen cell preparations with antibody-coupled magnetic beads, osteoclast formation increased and there was no additional response to A-C2 (SEQ ID NO: 14; FIG. 10). Similarly, A-C2 (SEQ ID NO: 14) dose-dependent stimulation of TRAP+, multinucleated cell differentiation in RAW264.7 cultures was only observed when T cells were added to the cultures (FIG. 11). These results indicate that T cells express an inhibitory factor (most likely sFRP-1) that is blocked by A-C2 (SEQ ID NO: 14).

Example 8

Structural Analysis Shows that sFRP-1/RANKL Binding Extends Beyond the Peptide Motif Structure-function analysis of sFRP-1/RANKL interaction was performed by testing RANKL's ability to bind to a set of sFRP-1 deletion mutants (FIG. 12). The strongest binding was observed with a derivative that contained the CRD, and strong binding was subsequently seen with a similar variant comprising the CRD that was expressed in bacteria. Of note, we also observed binding of sFRP-1 to a derivative of RANKL that lacked the sequence corresponding to the A-C2 motif (this RANKL variant had an amino-terminal sequence beginning with residue 158). This implied that the binding of RANKL and sFRP-1 did not rely entirely on the presence of the A-C2 sequence. Moreover, it implied that other proteins structurally related to RANKL but lacking the AC2-like sequence might also bind sFRP-1. We have tested this hypothesis and now have evidence that TNFa also can bind sFRP-1 in an ELISA format, using conditions comparable to those described above for RANKL binding studies. Moreover, similar experiments performed with sFRP-2 indicate that it can bind to RANKL and another TNFα family member, the TNF-related apoptosis-inducing ligand (TRAIL). Thus, we now believe that additional interactions occur between members of the sFRP and TNF families, besides the one involving sFRP-1 and RANKL.

Example 9

Identification of a Biologically Relevant Peptide Motif

The peptide motif, L/V-V-D-G-R-W-U/V (SEQ ID NO: 9), has not been previously identified as being capable of binding to sFRP-1. This binding activity has been characterized through the use of a series of ELISA experiments using peptide/alkaline phosphatase fusion proteins, alanine scanning mutagenesis and synthetic peptides. These experiments also demonstrated that substitutions in nearby residues could enhance or reduce the peptide motif/sFRP-1 binding, implying that systematic substitutions in adjacent residues and conservative changes within the peptide motif, are able to strengthen the interaction with sFRP-1.

Conservative substitutions replace one amino acid with another amino acid that is similar in size, hydrophobicity, etc. Such substitutions generally are conservative when it is desired to finely modulate the characteristics of the protein. Examples of amino acids which can be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. The binding affect of peptides in which such substitutions have been made can readily be confirmed by the peptide motif-binding assay disclosed herein.

More substantial changes in function or other features can be obtained by selecting substitutions that are less conservative than those described above, i.e. selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions which in general are expected to produce the greatest changes in protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histadyl, is substituted for (or by) an electronegative residue, e.g. glutamyl or aspartyl; or (d) a residue having a bulky side chain, e.g. phenylalanine, is substituted for (or by) one not having a side chain, e.g. glycine. The effects of these amino acid substitutions or deletions or additions can be assessed through the use of the ELISA binding assay provided herein.

Additionally, one of skill in the art will appreciate that nucleic acid sequences encoding the peptide motif can be designed by either synthetically synthesizing the appropriate nucleic acid sequence, or by using PCR to amplify the appropriate sequence. Once obtained the nucleic acid sequence can be placed in an appropriate expression vector and transformed into an organism such that the organism then produces the peptide.

The significance of the peptide motif (SEQ ID NO: 9) was demonstrated in experiments that revealed a dramatic stimulatory effect of a synthetic peptide bearing the peptide motif in osteoclastogenesis bioassays. The ability of the A-C2 peptide (SEQ ID NO: 14) to promote osteoclast formation was consistent with the idea that the peptide increased RANKL activity by blocking the inhibitory effect of endogenous sFRP-1 (FIG. 17).

The requirement of T cells for the A-C2 peptide (SEQ ID NO: 14) to stimulate osteoclast formation implied that splenic T cells express an osteoclastogenesis inhibitor sensitive to A-C2 (SEQ ID NO: 14). This inhibitor is believed to be sFRP-1, as sFRP-1 is expressed in spleen (Finch et al, *Proc. Natl. Acad. Sci. USA* 94:6770-6775, 1997). Hence, reagents possessing a sFRP-1 binding motif are believed to have utility in regulating RANKL signaling involved in T cell-dendritic communication that is modulated by endogenous sFRP-1. Such regulation can be exploited to optimize vaccine therapies in a variety of settings where T cell-dendritic cell interactions have an important role in the immune response.

Dendritic cells have been shown to promote vaccine responses, which can be determined by measuring titers to known antigens developed in inoculated animals (M. Di Nicola et al., *Cytokines Cell. Mol. Ther.* 4: 265-273, 1998; C. Reis e Sousa et al., Curr. Opin. Immunol. 11: 392-399, 1999; K. Tarte and B. Klein, *Leukemia* 13: 653-663, 1999). Efforts are underway to optimize the expansion of immunologically responsive dendritic cells in order to improve the efficacy of vaccine therapy (R. Hajek and A. W. Butch, *Med. Oncol.* 17: 2-15, 2000). Using methods cited in the above references, reagents corresponding to the sFRP-1 binding motif and sFRP-1 can be useful to enhance the immune response in vaccine therapies.

The association of sFRP-1 and T cells indicates that sFRP-1 can be useful for modulating endogenous proteolytic cleavage of RANKL. A large fraction of the RANKL expressed by T cells is proteolytically processed to release a soluble, biologically active form. This process, which can be mediated by the TNFα converting enzyme (TACE), involves cleavage at one or two sites in the RANKL sequence just upstream of the putative peptide-binding motif (SEQ ID NO: 9). Therefore, it is believed that sFRP-1 regulates the proteolytic processing of RANKL in a manner that could be reversed by reagents containing the peptide motif (SEQ ID NO: 9).

The ability of sFRP-1 to regulate RANKL processing is tested by culturing T-cells expressing RANKL and treating the cultures with various concentrations of sFRP-1. The resulting soluble RANKL proteins are then identified using a RANKL specific western blot The degree of RANKL processing is then correlated to the sFRP concentration in the sample.

In addition to the peptide motif's (SEQ ID NO: 9) impact on sFRP-1/RANKL binding, reagents containing the peptide motif (SEQ ID NO: 9) also have utility in disrupting the interaction of sFRP-1 with other proteins. As mentioned above, other known proteins like the netrin receptor, and UNC5H3 and the ANP receptor A, have sequences similar to the binding motif, and newly identified gene sequences can be routinely screened for such sequences. Proteins with this motif are likely to be additional potential binding partners for sFRP-1 and targets for reagents containing the sFRP-1 binding motif For instance, sFRP-1 binding to the ANP receptor A could regulate the release of sodium and fluid in the kidney and eye. Others have demonstrated that the relevant components of natriuretic peptide system are functionally expressed in the human eye where they could serve as modulators of intraocular pressure (J. Ortego and M. Coca-Prados, *Biochem. Biophys. Res. Commun.* 258: 21-28, 1999). In the eye, sFRP-1 or its binding peptide could have an important impact on the release of fluid into the eye with resultant changes in the intraocular pressure. These effects are tested using models of perfused eyes in organ culture, such as the one originally described by D. H. Johnson and R. C. Tschumper, *Invest. Ophthalmol. Vis. Sci.* 28: 945-953, 1987. Regulation of intraocular pressure has therapeutic benefit in the treatment of glaucoma.

Example 10 sFRP-1 Blocks Osteoclast Formation

As demonstrated herein, sFRP-1 has an inhibitory effect on osteoclastogenesis, which is likely due to its interaction with RANKL. The elevated expression of sFRP-1 transcript specifically in osteoblast lines capable of stimulating osteoclast formation initially suggested that sFRP-1 promotes osteoclastogenesis. However, the increase in sFRP-1 transcript observed in co-cultures of osteoblasts and hematopoietic progenitors as osteoclast formation proceeded implied that sFRP-1 was instead part of a tonic mechanism to limit the extent of osteoclast formation (FIG. 17). It is believed that this is important for homeostasis to ensure that an appropriate balance of osteoblast and osteoclast populations is maintained, along with a reserve of osteoclast progenitors that would be available when needed in the future. In addition, it is possible that low concentrations of sFRP-1 might have a permissive effect on osteoclast formation.

In view of sFRP-1's ability to inhibit osteoclastogenesis, sFRP-1 can have clinical utility in conditions where excessive osteoclast activity has pathological consequences. Osteoporosis and hypercalcemic osteopaenia are examples of such conditions; rheumatoid arthritis is another, which could be a particularly good target for sFRP-1 therapy because soluble RANKL from T cells is thought to have an important role in the bone loss associated with this disease.

Example 11

Other Interactions Between Members of the sFRP and TNFα Families

The results described above (Example 8) indicate that additional contact points within RANKL, besides the newly identified peptide-binding motif, are involved in the interaction of sFRP-1 (SEQ ID NO: 3) and RANKL. These results further indicate that sFRP family members interact with TNF-ligand family members.

TNF-ligand family members are known to be among the most pleiotropic cytokines, inducing a large number of cellular responses, including cytotoxicity, anti-viral activity, immunoregulatory activities, and the transcriptional regulation of several genes. Cellular responses to TNF-family ligands include not only normal physiological responses, but also diseases associated with increased apoptosis or the inhibition of apoptosis. Apoptosis-programmed cell death is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft v. host disease, acute graft rejection, and chronic graft rejection. Diseases associated with increased apoptosis include AIDS, neurodegenerative disorders, myelodysplastic syndromes, ischemic injury, toxin-induced liver disease, septic shock cachexia and anorexia.

Thus, the disclosure further provides methods for modulating the TNF ligand/TNF receptor interactions. These methods involve contacting sFRP, a fragment or variant of sFRP, or the peptide motif (SEQ ID NO: 9) with a member of the TNF-ligand family of proteins, and detecting a change in TNF-ligand biological activity.

Whether the sFRP, fragment or variant of sFRP, or the peptide motif acts as an "agonist" or antagonist" can readily be determined using any one of the well known TNF-family ligand/receptor cellular response assays, such as ones described in the references cited in the following reviews: D. Wallach et al., *Annu. Rev. Immunol.* 17: 331-367, 1999; S. J. Baker and E. P. Reddy, *Oncogene* 17: 3261-3270, 1998

Thus, the disclosure provides screening methods for determining whether a candidate agonist or antagonist is capable of enhancing or inhibiting a cellular response to a TNF-family ligand.

Example 12 sFRP-1/Peptide Binding

ELISA experiments were performed essentially as described above with a series of sFRP-1 deletion mutants (in Uren et al., *J. Biol. Chem.*, 275: 4374-4382, 2000) to determine what region(s) of the protein were required for binding to the AC2/alkaline phosphatase chimera. Optimal binding was observed with the Δ3 derivative, which contains all of the Fz CRD and a portion of the C-terminal region. Little binding was detected with derivatives that contained the CRD alone or the C-terminal region alone.

Thus, a combination of elements from the CRD and the C-terminal domain were required for AC2 binding. As derivatives that did not bind well to the AC2 chimera bound other reagents, and in some instances showed biological activity; therefore, they are unlikely to be simply misfolded.

Having illustrated and described the principles of the disclosure in multiple embodiments and examples, it should be apparent to those skilled in the art that the disclosure can be modified in arrangement and detail without departing from such principles. We claim all modifications coming within the spirit and scope of the following claims.

We claim:

1. A method of inhibiting osteoclast formation comprising:
   selecting a subject in need of inhibition of osteoclast formation; and
   contacting an osteoclast progenitor cell with (a) a polypeptide comprising an amino acid sequence comprising at least 90% sequence identity to the amino acid sequence set forth as SEQ ID NO: 3 or (b) a polypeptide comprising a fragment of SEQ ID NO: 3, wherein the polypeptide and the fragment inhibit differentiation of osteoclast progenitor cells, thereby inhibiting osteoclast formation.

2. The method of claim 1, wherein the method comprises contacting the osteoclast progenitor cell with the polypeptide comprising the fragment of SEQ ID NO: 3 and wherein the fragment comprises the amino acid sequence set forth as SEQ ID NO: 5, SEQ ID NO: 6, or SEQ ID NO: 7.

3. The method of claim 2, wherein the osteoclast progenitor cell is in vitro.

4. The method of claim 2, wherein the osteoclast progenitor cell is in vivo.

5. The method of claim 2, wherein the fragment comprises the amino acid sequence set forth as SEQ ID NO: 5.

6. The method of claim 2, wherein the fragment comprises the amino acid sequence set forth as SEQ ID NO: 6.

7. The method of claim 2, wherein the fragment comprises the amino acid sequence set forth as SEQ ID NO: 7.

8. The method of claim 1, wherein the osteoclast progenitor cell is a bone marrow cell.

9. The method of claim 1, wherein the osteoclast progenitor cell is a spleen cell.

10. The method of claim 1, wherein the osteoclast progenitor cell is a hematopoietic stem cell.

11. The method of claim 1, wherein the polypeptide comprises an amino acid sequence comprising at least 95% sequence identity to the amino acid sequence set forth as SEQ ID NO: 3.

12. The method of claim 11, wherein the polypeptide comprises an amino acid sequence comprising at least 98% sequence identity to the amino acid sequence set forth as SEQ ID NO: 3.

13. The method of claim 12, wherein the polypeptide comprises the amino acid sequence as set forth as SEQ ID NO: 3.

14. The method of claim 13, wherein the polypeptide consists of the amino acid sequence set forth as SEQ ID NO: 3.

15. The method of claim 1, wherein the polypeptide comprises a cysteine rich domain.

16. The method of claim 1, further comprising measuring osteoclast formation.

17. The method of claim 1, wherein the subject has postmenopausal osteoporosis, Paget's disease, lytic bone metastases, multiple myeloma, hyperparathyroidism, rheumatoid arthritis, periodontitis, or hypercalcemia of malignancy.

18. The method of claim 17, wherein the subject has postmenopausal osteoporosis.

19. A method of inhibiting osteoclast formation comprising:
    contacting an osteoclast progenitor cell with (a) a polypeptide comprising an amino acid sequence comprising at least 90% sequence identity to the amino acid sequence set forth as SEQ ID NO: 3 or (b) a polypeptide comprising a fragment of SEQ ID NO: 3, wherein the polypeptide and the fragment inhibit differentiation of osteoclast progenitor cells; and
    measuring osteoclast formation to determine if osteoclast formation has been inhibited.

20. The method of claim 19, wherein the polypeptide comprises an amino acid sequence comprising at least 95% sequence identity to the amino acid sequence set forth as SEQ ID NO: 3.

21. The method of claim 20, wherein the polypeptide comprises an amino acid sequence comprising at least 98% sequence identity to the amino acid sequence set forth as SEQ ID NO: 3.

22. The method of claim 21, wherein the polypeptide comprises the amino acid sequence set forth as SEQ ID NO: 3.

23. The method of claim 22, wherein the polypeptide consists of the amino acid sequence set forth as SEQ ID NO: 3.

24. The method of claim 19, wherein the osteoclast progenitor cell is a bone marrow cell.

25. The method of claim 19, wherein the osteoclast progenitor cell is a spleen cell.

26. The method of claim 19, wherein the osteoclast progenitor cell is a hematopoietic stem cell.

27. The method of claim 19, wherein the method comprises contacting the osteoclast progenitor cell with the polypeptide comprising the fragment of SEQ ID NO: 3 and wherein the fragment comprises the amino acid sequence set forth as SEQ ID NO: 5, SEQ ID NO: 6, or SEQ ID NO:7.

28. The method of claim 27, wherein the osteoclast progenitor cell is in vitro.

29. The method of claim 27, wherein the osteoclast progenitor cell is in vivo.

30. The method of claim 27, wherein the fragment comprises the amino acid sequence set forth as SEQ ID NO: 5.

31. The method of claim 27, wherein the fragment comprises the amino acid sequence set forth as SEQ ID NO: 6.

32. The method of claim 27, wherein the fragment comprises the amino acid sequence set forth as SEQ ID NO: 7.

33. The method of claim 19, wherein the polypeptide comprises a cysteine rich domain.

* * * * *

UNITED STATES PATENT AND TRADEMARK OFFICE
CERTIFICATE OF CORRECTION

PATENT NO. : 7,488,710 B2
APPLICATION NO. : 10/466136
DATED : February 10, 2009
INVENTOR(S) : Rubin et al.

It is certified that error appears in the above-identified patent and that said Letters Patent is hereby corrected as shown below:

Column 2, line 60, "binding t" should read --binding to--.

Column 3, line 50, "wer treated" should read --were treated--.

Column 4, line 45, "fr m the" should read --from the--.

Column 7, line 16, "terns" should read --terms--.

Column 9, line 30, "thereof Other" should read --thereof. Other--.

Column 10, line 22, "thereof" should read --thereof.--.

Column 11, line 62, "motifs" should read --motif's--.

Column 14, line 44, "parameters, (gap)" should read --parameters (gap)--.

Column 15, line 30, "the, term" should read --the term--.

Column 18, line 23, "differentiation" should read --differentiation.--.

Column 21, line 55, "motif s" should read --motif's--.

Column 28, line 58, "interest Using" should read --interest. Using--.

Column 35, line 34, "(FIG. 14) The" should read --(FIG. 14). The--.

Column 36, line 42, "L/V-V-D-G-R-W-U/V" should read --L/V-V-D-G-R-W-L/V--.

Column 38, line 26, "motif For" should read --motif. For--.

UNITED STATES PATENT AND TRADEMARK OFFICE
CERTIFICATE OF CORRECTION

PATENT NO. : 7,488,710 B2
APPLICATION NO. : 10/466136
DATED : February 10, 2009
INVENTOR(S) : Rubin et al.

It is certified that error appears in the above-identified patent and that said Letters Patent is hereby corrected as shown below:

Column 40, line 9, "1998" should read --1998.--.

Signed and Sealed this

Fifteenth Day of December, 2009

David J. Kappos
*Director of the United States Patent and Trademark Office*